(12) United States Patent
Qu et al.

(10) Patent No.: US 11,959,143 B2
(45) Date of Patent: Apr. 16, 2024

(54) MICRORNA PROFILING FOR DIAGNOSIS OF DYSPLASTIC NEVI AND MELANOMA

(71) Applicant: Quest Diagnostics Investments LLC, Secaucus, NJ (US)

(72) Inventors: Kevin Qu, Lake Forest, CA (US); Anthony Sferruzza, San Clemente, CA (US); Ke Zhang, San Clemente, CA (US); Yan Liu, San Juan Capistrano, CA (US); Renius Owen, San Juan Capistrano, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 707 days.

(21) Appl. No.: 17/103,544

(22) Filed: Nov. 24, 2020

(65) Prior Publication Data
US 2021/0147947 A1    May 20, 2021

Related U.S. Application Data

(60) Continuation of application No. 15/999,033, filed on Aug. 20, 2018, now Pat. No. 10,851,424, which is a division of application No. 15/240,207, filed on Aug. 18, 2016, now Pat. No. 10,053,738, which is a continuation of application No. 13/728,053, filed on Dec. 27, 2012, now Pat. No. 9,447,471.

(60) Provisional application No. 61/581,571, filed on Dec. 29, 2011.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC ............ C12Q 1/6886; C12Q 2600/112; C12Q 2600/118; C12Q 2600/178
USPC ..................... 436/6.1, 91.1, 91.31
See application file for complete search history.

(56) References Cited

U.S. PATENT DOCUMENTS

| | | |
|---|---|---|
| 2007/0072204 A1 | 3/2007 | Hannon |
| 2008/0200416 A1 | 8/2008 | Li et al. |
| 2009/0010908 A1 | 1/2009 | Gow |
| 2009/0239818 A1 | 9/2009 | Cheng |
| 2010/0179213 A1* | 7/2010 | Patrawala ............... A61P 35/00 435/6.1 |
| 2010/0298151 A1 | 11/2010 | Taylor et al. |
| 2012/0190730 A1 | 7/2012 | Michael |
| 2014/0220580 A1 | 8/2014 | Brown |
| 2016/0076103 A1 | 3/2016 | Keller et al. |
| 2017/0081725 A1 | 3/2017 | Qu et al. |
| 2017/0088899 A1 | 3/2017 | Qu et al. |
| 2019/0071672 A1 | 3/2019 | Elmen et al. |
| 2019/0085410 A1 | 3/2019 | Taylor et al. |

FOREIGN PATENT DOCUMENTS

| | | | | |
|---|---|---|---|---|
| CA | 2799163 A1 * | 6/2013 | ....... | G01N 33/57484 |
| CA | 2859021 A1 * | 6/2013 | ........... | C12Q 1/6886 |

OTHER PUBLICATIONS

Mueller et al (J. Invest. Dermatol., vol. 129, pp. 1740-1751 (2009)) (Year: 2009).*
Chan et al., MicroRNA signatures differentiate melanoma subtypes, Cell Cycle, vol. 10, No. 11, pp. 1845-1852, Jun. 2011.
Mueller et al., "miRNA Expression Profiling in Melanocytes and Melanoma Cell Lines Reveals miRNAs Associated with Formation and Progression of Malignant Melanoma," Journal of Investigative Dermatology, vol. 129, pp. 1740-1751, Feb. 2009.
Office Action dated Jun. 25, 2013 in U.S. Appl. No. 13/728,053.
Office Action dated Feb. 18, 2014 in U.S. Appl. No. 13/728,053.
Office Action dated Sep. 17, 2014 in U.S. Appl. No. 13/728,053.
Office Action dated Mar. 11, 2015 in U.S. Appl. No. 13/728,053.
Office Action dated Oct. 26, 2015 in U.S. Appl. No. 13/728,053.
Office Action dated Jan. 26, 2016 in U.S. Appl. No. 13/728,053.
Notice of Allowance dated May 6, 2016 in U.S. Appl. No. 13/728,053.
Office Action dated Aug. 24, 2017 in U.S. Appl. No. 15/229,568.
Notice of Allowance dated Jan. 17, 2018 in U.S. Appl. No. 15/229,568.
Office Action dated Mar. 2, 2020 in U.S. Appl. No. 15/999,033.
Notice of Allowance dated Jul. 29, 2020 in U.S. Appl. No. 15/999,033.

* cited by examiner

*Primary Examiner* — Jane J Zara
(74) *Attorney, Agent, or Firm* — Foley & Lardner LLP

(57) ABSTRACT

Provided herein are methods for miRNA profiling for the diagnosis, prognosis, and management of melanoma and differentiation of melanoma from nevi.

12 Claims, 25 Drawing Sheets

MICRORNA PROFILING FOR DIAGNOSIS OF DYSPLASTIC NEVI AND MELANOMA

FIELD OF THE INVENTION

The invention generally relates to miRNA profiling for the diagnosis, prognosis, and management of melanoma and differentiation of melanoma from nevi.

BACKGROUND OF THE INVENTION

The following discussion of the background of the invention is merely provided to aid the reader in understanding the invention and is not admitted to describe or constitute prior art to the present invention.

Skin cancer is the most common of all cancers, afflicting more than a million Americans each year, a number that is rising rapidly. It is also the easiest to cure, if diagnosed and treated early. If allowed to progress to the point where it spreads to other sites (metastasizes), the prognosis (forecast) is very poor. More than 8,000 melanoma deaths now occur per year.

Melanoma most often appears as an asymmetrical, irregularly bordered, multicolored or tan/brown spot or growth that continues to increase in size over time. It may begin as a flat spot and become more elevated. In rare instances, it may not be pigmented.

Dysplastic nevi (atypical moles) are unusual or benign moles that may resemble melanoma. People who have them are at increased risk of developing single or multiple melanomas. The higher the number of these moles someone has, the higher the risk; those who have 10 or more have 12 times the risk of developing melanoma compared to the general population. Dysplastic nevi are found significantly more often in melanoma patients than in the general population.

Melanoma is distinguished from nevi, other forms of cancer, and normal skin on the basis of clinical presentation and histopathological examination of a skin biopsy, usually a formalin fixed, paraffin embedded (FFPE) sample. Considerable expertise is required to reliably distinguish between nevi and melanoma.

This application describes novel microRNA biomarkers with microRNA array and RT-PCR to better characterize dysplastic nevi, malignant melanoma and metastatic melanoma. miRNA can therefore serve as an adjunct to histopathology for correct classification of melanoma, nevi and other conditions, especially where there is doubt as to the diagnosis.

SUMMARY OF THE INVENTION

The present invention is based on the discovery that melanoma can be distinguished from nevi by measuring changes in the levels of as little as two miRNAs.

In one aspect, the invention provides a method for differentially diagnosing melanoma from nevi, by (a) measuring the level of two or more miRNAs selected from the group consisting of: miR-132, miR-150, miR-339-5p, miR-15b, miR-342-3p, miR-572, miR-155, miR-425, miR-1202, miR-1268, HBII-382_s, miR-1225-5p, miR-30c, miR-106b-star, miR-125a-5p, mgU6-53B, miR-25, miR-149-star, miR-939, miR-92b-star, miR-500-star, miR-22, HBII-142_x, miR-181b, HBII-142, U38B, miR-663, miR-1224-5p, miR-23a, HBII-85-6_x, miR-1207-5p, miR-1301, miR-1228-star, miR-345, miR-30a-star, ENSG00000199411, ENSG00000202327, miR-92a, miR-127-3p, HBII-85-26, miR-1308, miR-31, miR-921, miR-146b-5p, miR-768-3p, miR-708, miR-139-5p, ACA24_x, miR-501-3p, miR-502-3p, miR-923, and miR-191; and (h) diagnosing the skin sample as containing melanoma when a difference in the level of the two or more miRNAs compared to a reference level indicates melanoma in the sample. The level of two, three, four, five, six, seven, eight, nine, ten, eleven, twelve, thirteen, fourteen, or more, miRNAs are measured.

In specific embodiments, the miRNAs to be measured include the following combinations (i) miR-150 and miR-149-star; (ii) miR-150, miR-149-star and miR-1308; (iii) miR-150, miR-149-star, miR-1308, and miR-191; (iv) miR-150, miR-149-star, miR-1308, miR-191, and miR-1228-star; (v) miR-150, miR-149-star, miR-1308, miR-191, miR-1228-star, and ENSG00000199411; (vi) miR-150, miR-149-star, miR-1308, miR-191, miR-1228-star, ENSG00000199411, and miR-1268; (vii) miR-150, miR-149-star, miR-1308, miR-191, miR-1228-star, FNSG00000199411, miR-1268, and miR-923; (viii) miR-150, miR-149-star, miR-1308, miR-191, miR-1228-star, ENSG00000199411, miR-1268, miR-923, and miR-23a; (ix) miR-150, miR-149-star, miR-1308, miR-191, miR-1228-star, ENSG00000199411, miR-1268, miR-923, miR-23a, and miR-132; (x) miR-150, miR-149-star, miR-1308, miR-191, miR-1228-star, ENSG00000199411, miR-1268, miR-923, miR-23a, miR-132, and miR-1207.5p; (xi) miR-150, miR-149-star, miR-1308, miR-191, miR-1228-star, ENSG00000199411, miR-1268, miR-923, miR-23a, miR-132, miR-1207.5p, and miR-342.3p; (xii) miR-150, miR-149-star, miR-1308, miR-191, miR-1228-star, ENSG00000199411, miR-1268, miR-923, miR-23a, miR-132, miR-1207.5p, miR-342.3p, and U38B; (xiii) miR-150, miR-149-star, miR-1308, miR-191, miR-1228-star. ENSG00000199411, miR-1268, miR-923, miR-23a, miR-132, miR-1207.5p, miR-342.3p, U38B, and miR-155.

In specific embodiments, melanoma is diagnosed in the skin sample by alterations in the level of an miRNA compared to a reference level, with the following alterations observed in at least two miRNA selected from the group consisting of: (i) miR-150 increase; (ii) miR-149-star decrease; (iii) miR-1308 decrease; (iv) miR-191 increase: (v) miR-1228-star decrease; (vi) ENSG00000199411_s decrease; (vii) miR-1268 decrease; (viii) miR-923 decrease; (ix) miR-23a increase; (x) miR-132 increase; (xi) miR-1207.5p decrease; (xii) miR-342.3p increase; (xiii) J38B decrease; and (xiv) miR-155 increase.

In one aspect, the invention provides a method for differentially diagnosing melanoma from nevi, by (a) measuring the level of two or more miRNAs selected from the group consisting of: miR-1268, miR-1228-star, miR-92b-star, miR-155, miR-345, miR-425, miR-132, miR-1207-5p, miR-1301, miR-663, miR-339-5p, miR-149-star, miR-150, miR-18a, miR-103, miR-191, miR-296-3p, miR-31, miR-107*, miR-93*, miR-1275*, miR-181B*, miR-921*, miR-1225-5p, miR-1202, and miR-342-3p and (b) diagnosing the skin sample as containing melanoma when a difference in the level of the two or more miRNAs compared to a reference level indicates melanoma in the sample.

In specific embodiments, melanoma is diagnosed in the skin sample by alterations in the level of an miRNA compared to a reference level, with the following alterations observed in at least two miRNA selected from the group consisting of: miR-1268 decrease, miR-1228-star decrease, miR-92b-star decrease, miR-155 increase, miR-345 increase, miR-425 increase, miR-132 increase, miR-1207-5p decrease, miR-1301 increase, miR-663 decrease, miR-339-5p increase, miR-149-star decrease, miR-150 increase, miR-18a increase, miR-103 increase, miR-191 increase, miR-296-3p decrease, miR-31 increase, miR-107* increase, miR-93* increase, miR-1275* decrease, miR-181B* increase, miR-921* decrease, miR-1225-5p increase, miR-1202 decrease, and miR-342-3p increase.

The method of the invention may further include internal controls, such as measuring the level of an miRNA selected from miR-27b, miR-195, miR-199b-3p, and miR-199a-3p.

In yet further embodiments, the level of two or more miRNAs are used to distinguish melanoma from normal skin, and nevi from normal skin. Additional miRNA levels may be assayed for this purpose.

The level of miRNA in the sample can be determined by microarray and/or quantitative real-time PCR. The method of the invention may be performed on a fresh skin sample, on a fixed and/or paraffin-embedded sample. In one embodiment the skin sample is formalin-fixed and paraffin-embedded.

The method of the invention may further comprise other steps in the diagnosis of melanoma, and the differentiation between nevi and melanoma, including histopathological assessment, and clinical assessment. In related embodiments, the clinical and/or histopathological evaluations may be converted into a score that can be combined with a score derived from miRNA levels, resulting in a diagnostic score that reflects the likelihood of melanoma.

The method of the invention may further include a step of isolating nucleic acids from the sample. An additional step may include amplification of the nucleic acid.

In further embodiments, the invention comprise a kit. In one embodiment, a kit for differentially diagnosing between melanoma and nevus in a skin sample comprises primers for the amplification of at least two miRNA selected from the group consisting of: miR-150, miR-149-star, miR-1308; miR-191; miR-1228-star; ENSG00000199411_s; miR-1268; miR-923; miR-23a; miR-132; miR-1207.5p; miR-342.3p; U38B; and miR-155.

In another embodiment, the kit comprises primers for the amplification of at least two miRNAs selected from the group consisting of: miR-1268, miR-1228-star, miR-92b-star, miR-155, miR-345, miR-425, MiR-132, miR-1207-5p, miR-1301, miR-663, miR-339-5p, miR-149-star, miR-150, miR-18a, miR-103, miR-191, miR-296-3p, miR-31, miR-107*, miR-93*, miR-1275*, miR-181B*, miR-921*, miR-1225-5p, miR-1202, and miR-342-3p.

The kit may also primers for amplification of controls, such as miR-27b, miR-195, miR-199b-3p, and miR-199a-3p.

The kit may also include suitable buffers, reagents for isolating nucleic acid, and instructions for use Kits may also include a microarray for measuring miRNA levels.

DETAILED DESCRIPTION OF THE INVENTION

Figure 1:
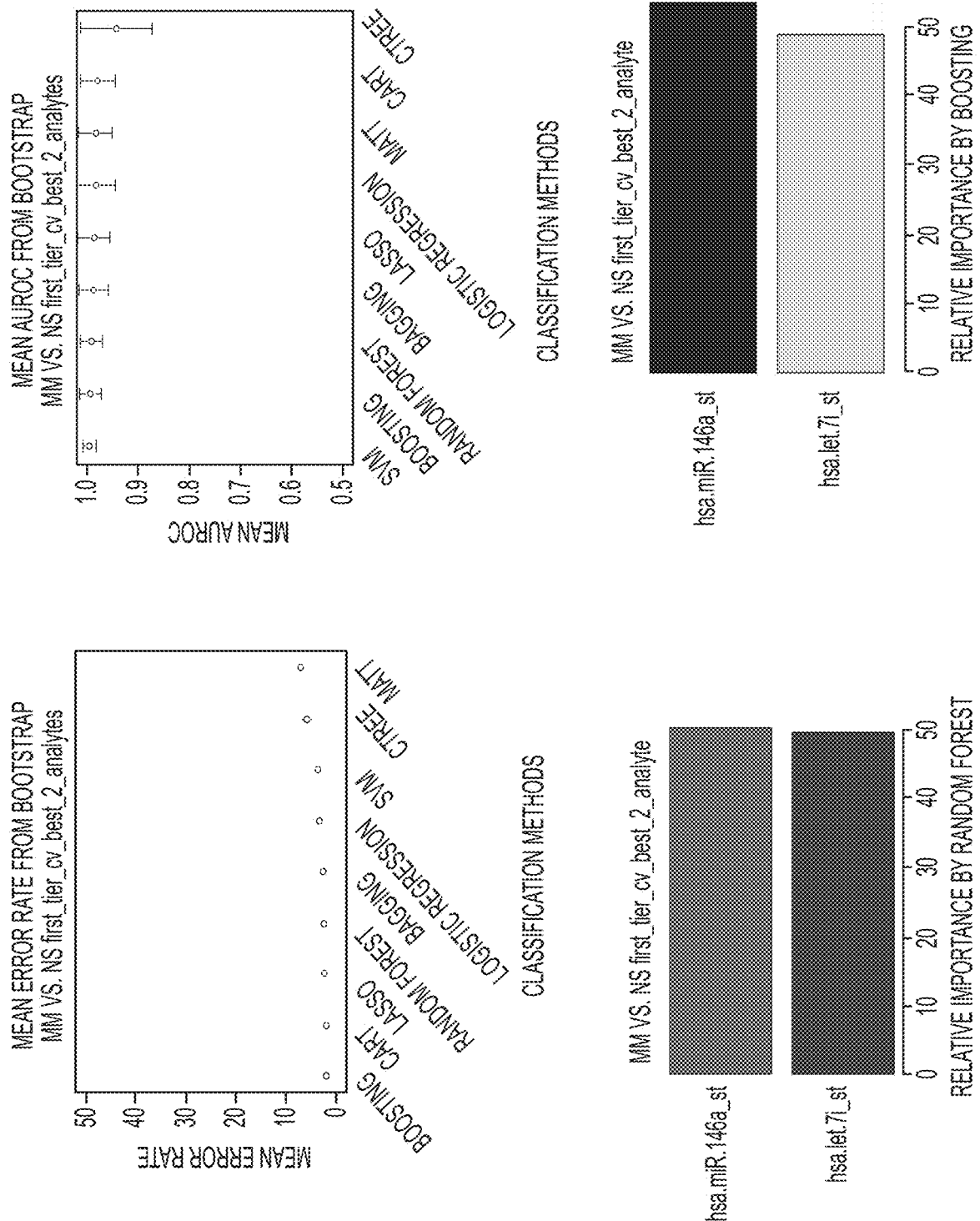
FIGS. 1-10 show, respectively, the best 2-10 miRNA combinations for differentiating melanoma (MM) from normal skin (NS), and the relevant error rates and AUC, as determined by different statistical algorithms.
Figure 2:
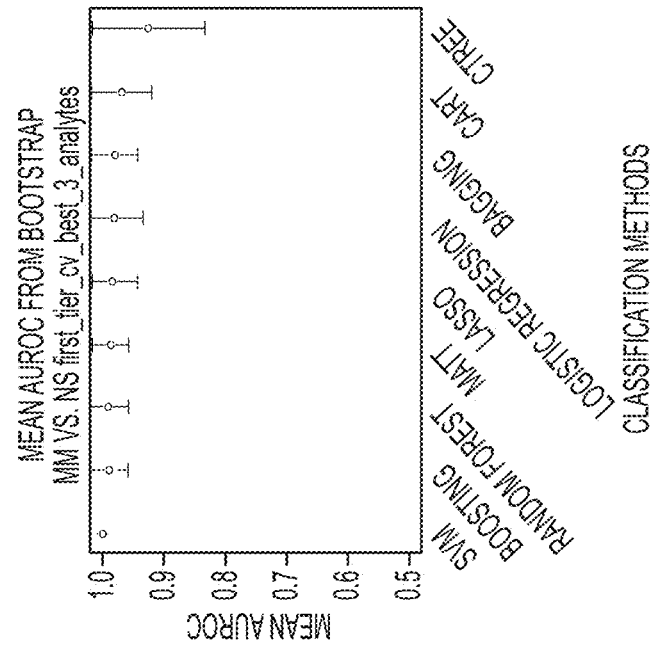
Figure 2:
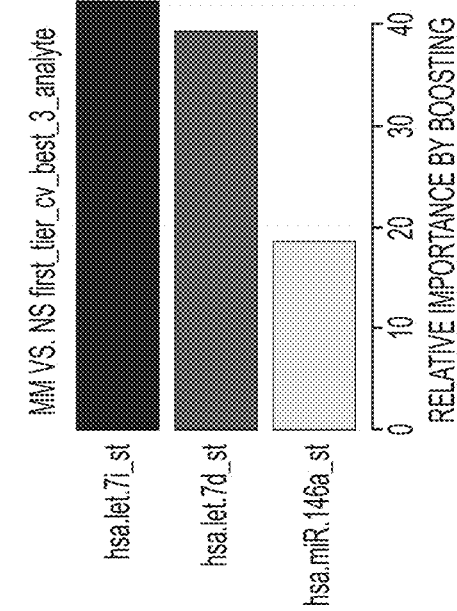
Figure 2:
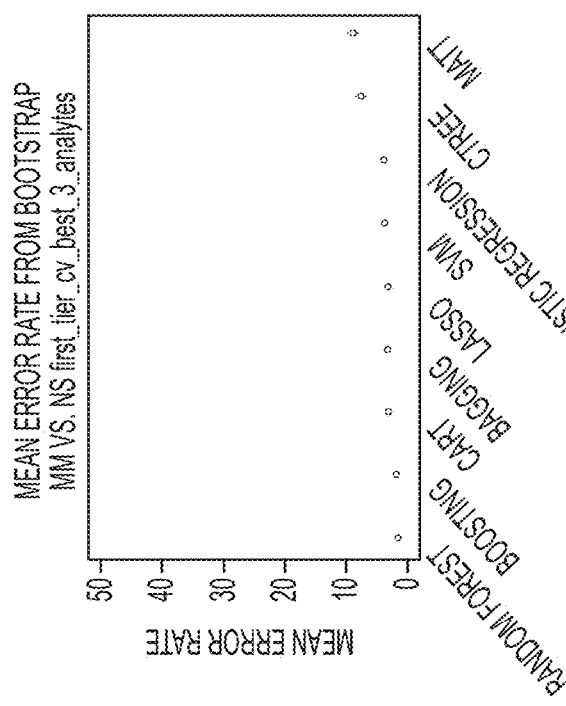
Figure 2:
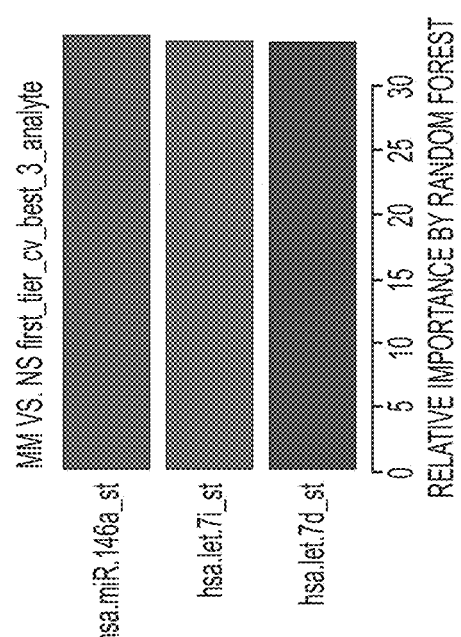
Figure 3:
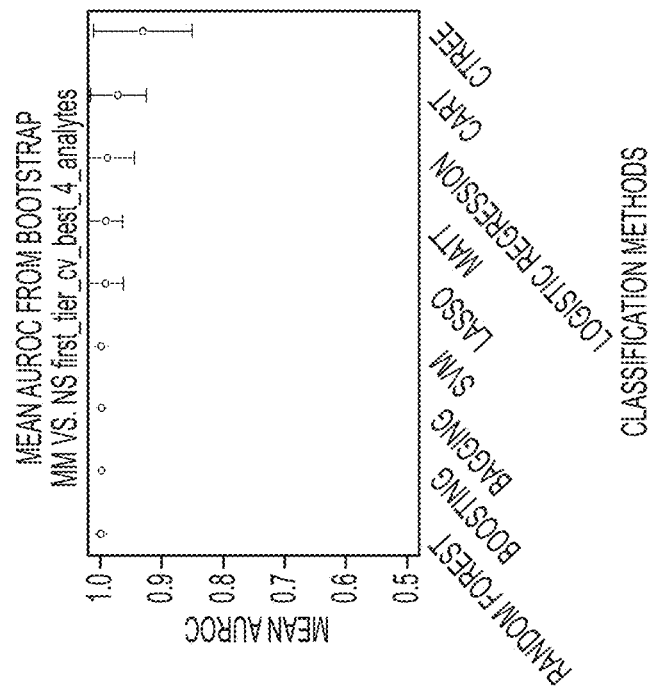
Figure 3:
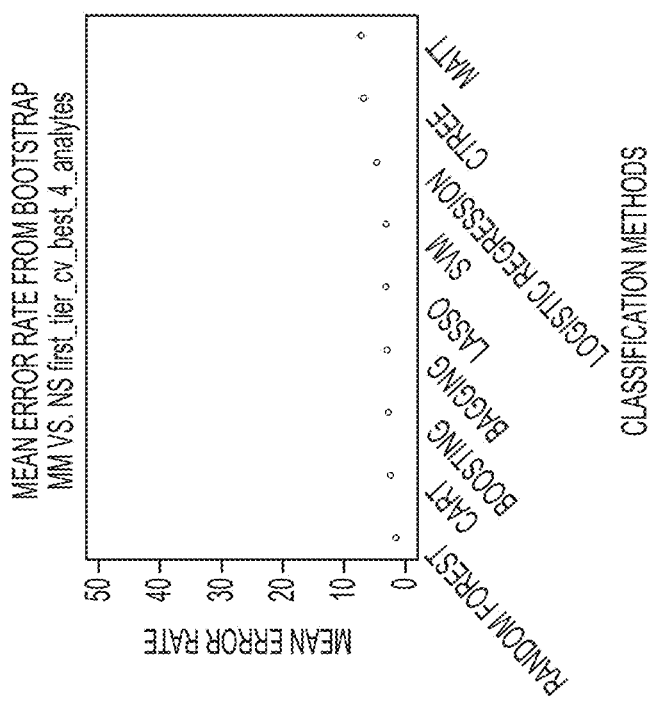
Figure 3:
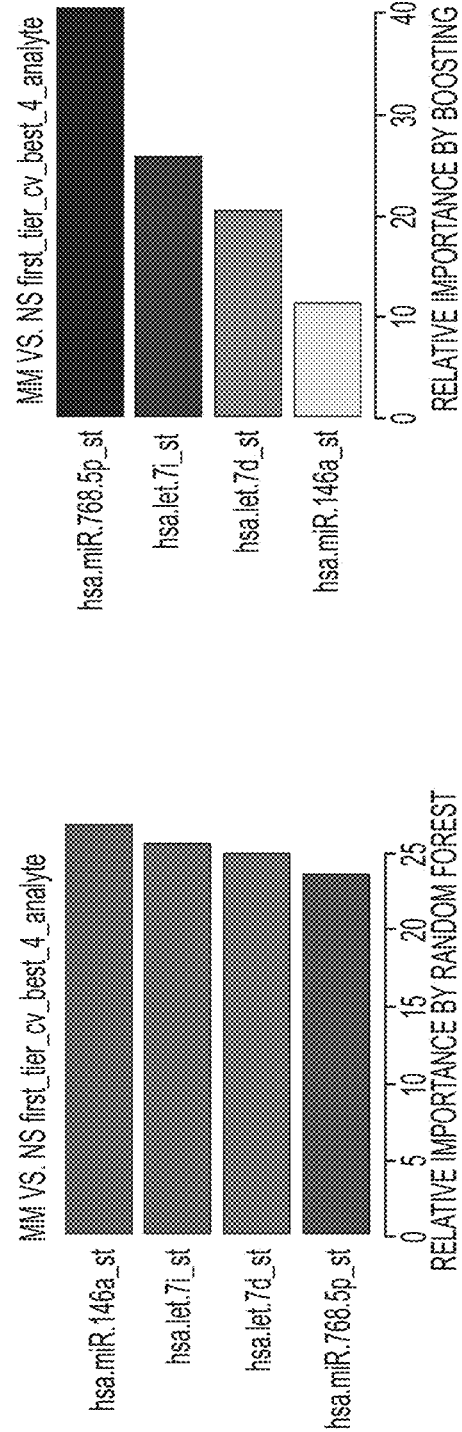
Figure 4:
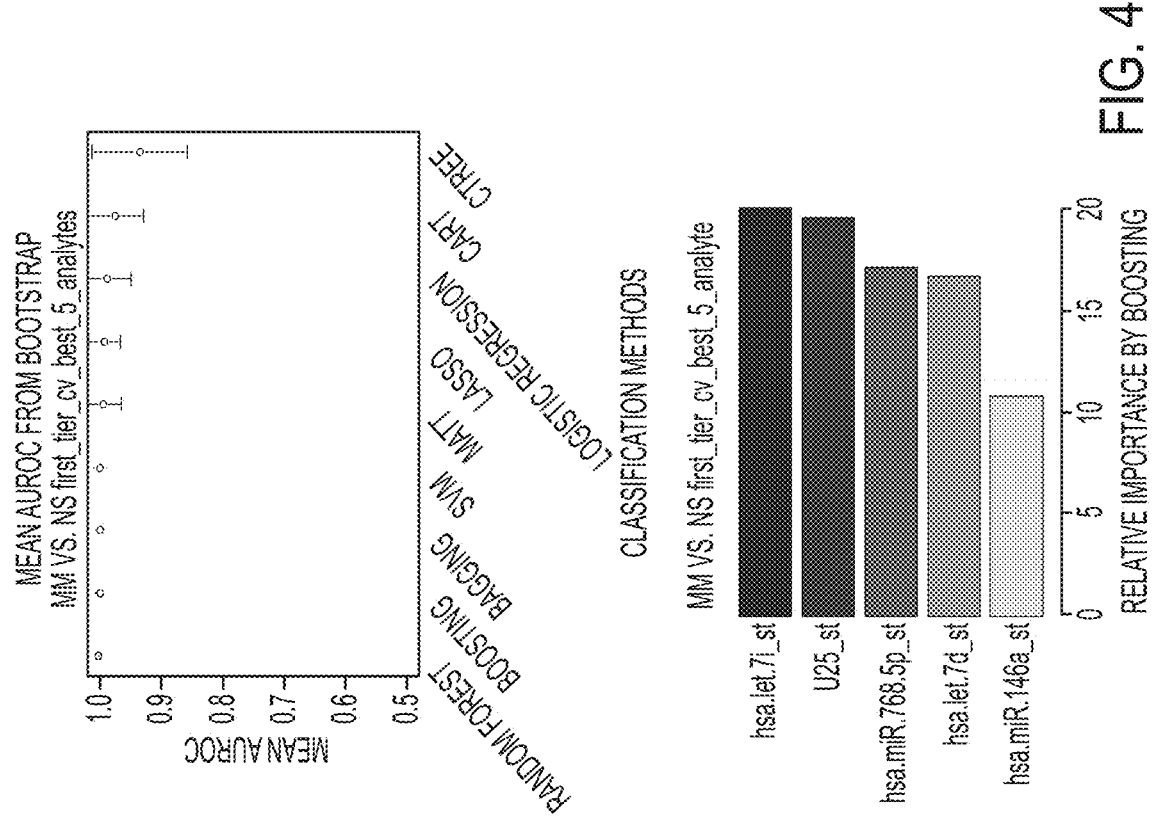
Figure 4:
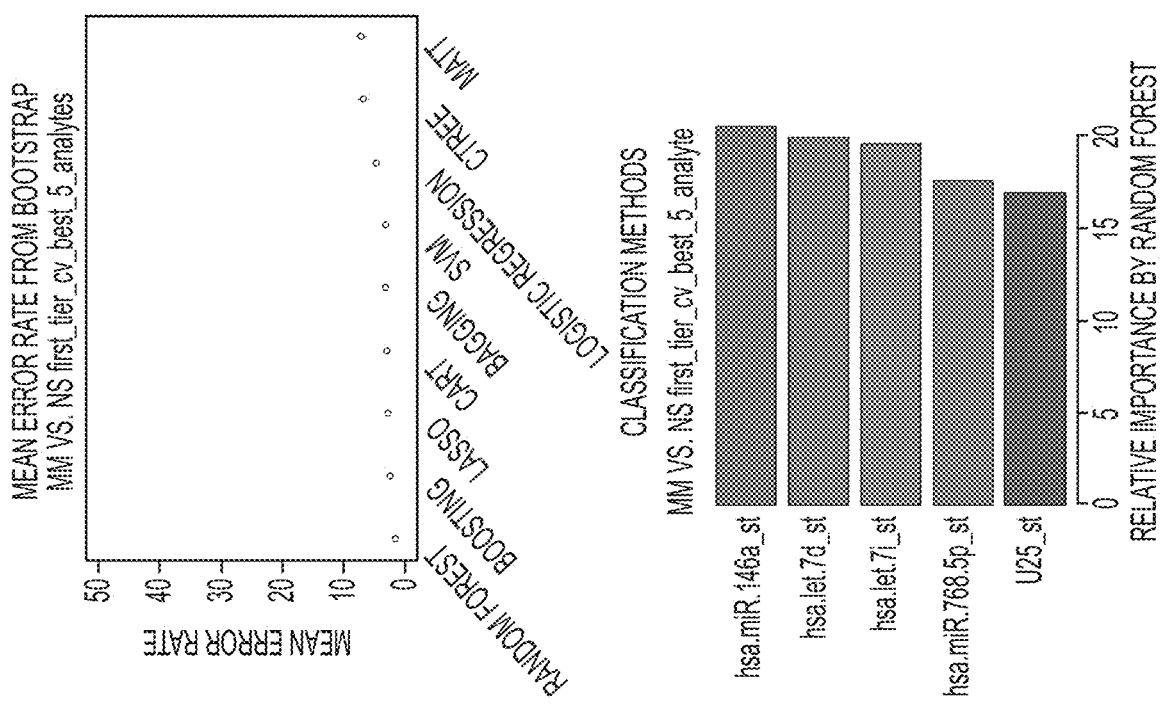
Figure 5:
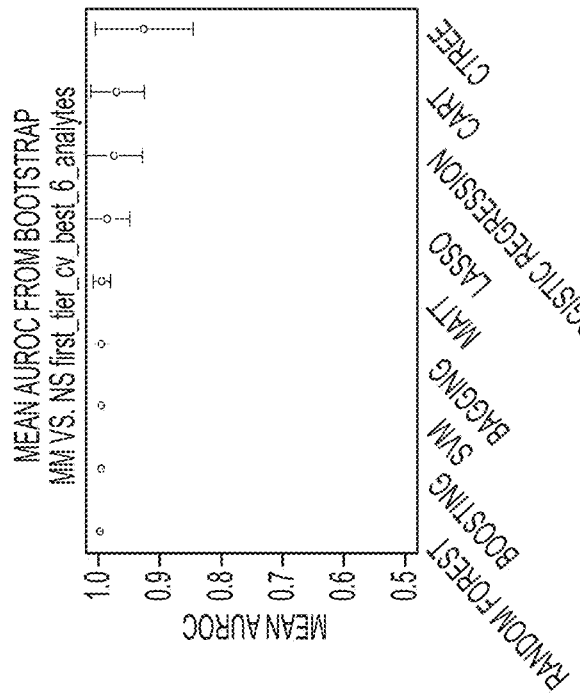
Figure 5:
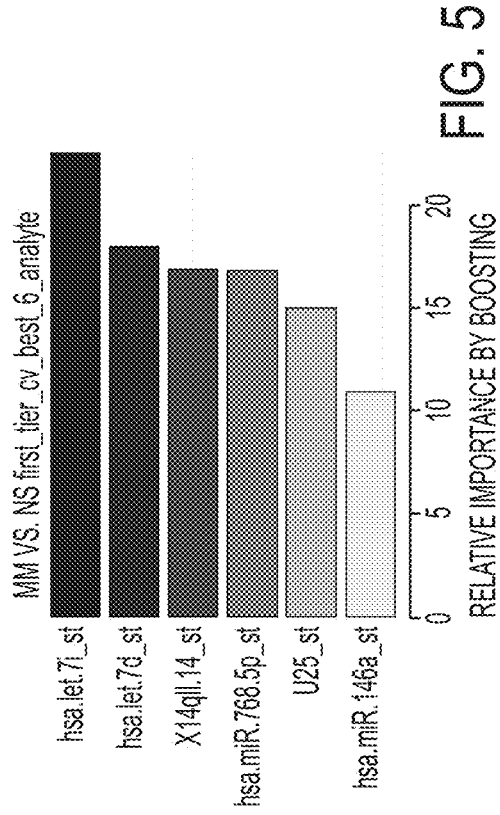
Figure 5:
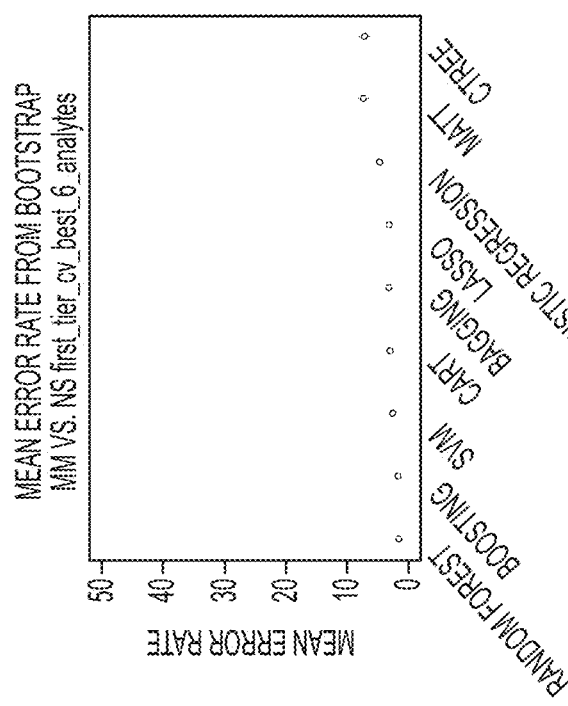
Figure 5:
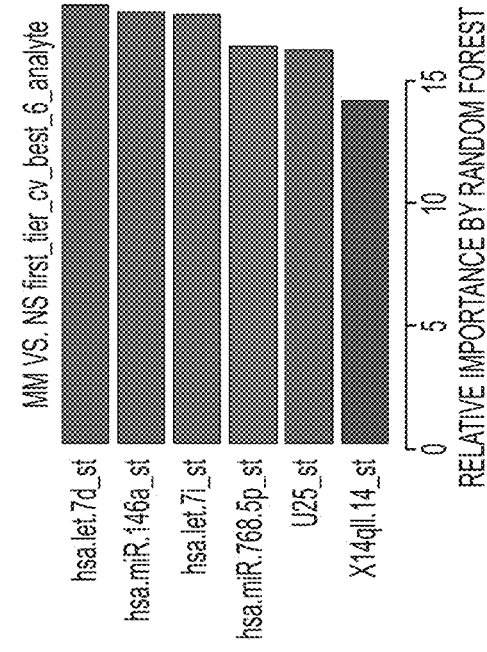
Figure 6:
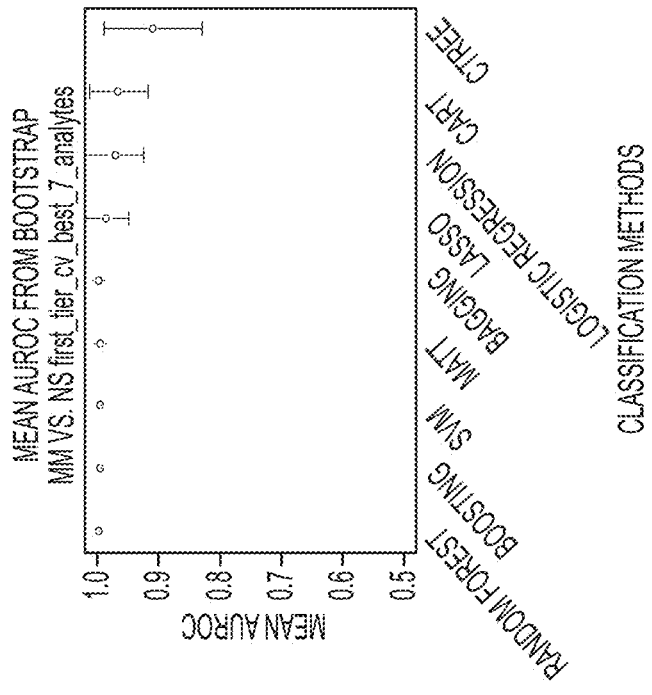
Figure 6:
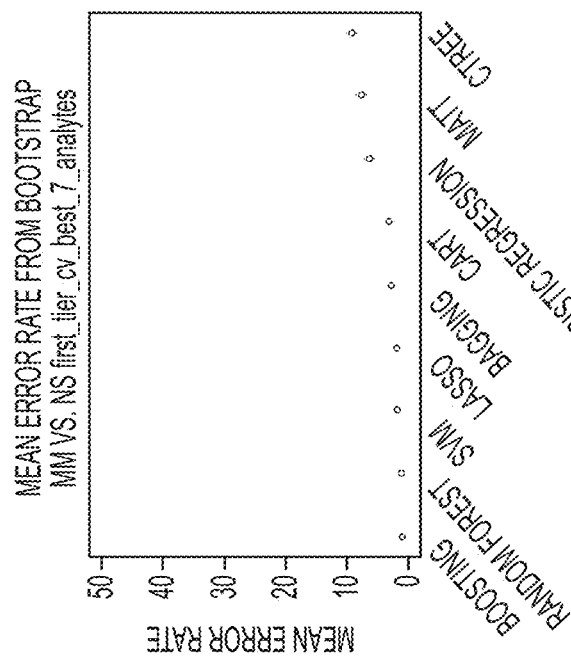
Figure 6:
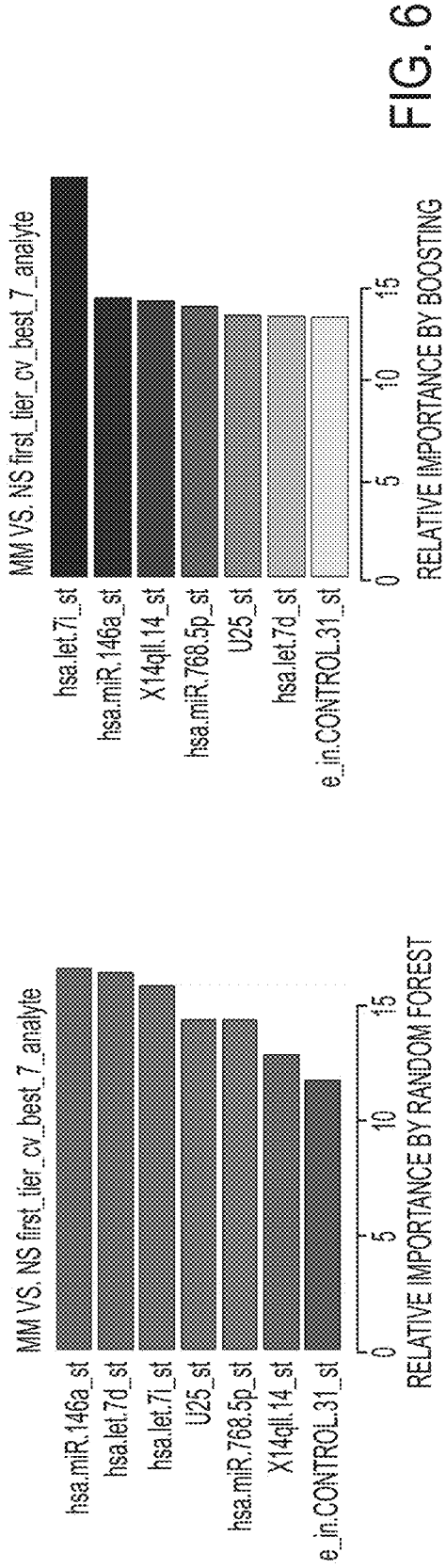
Figure 7:
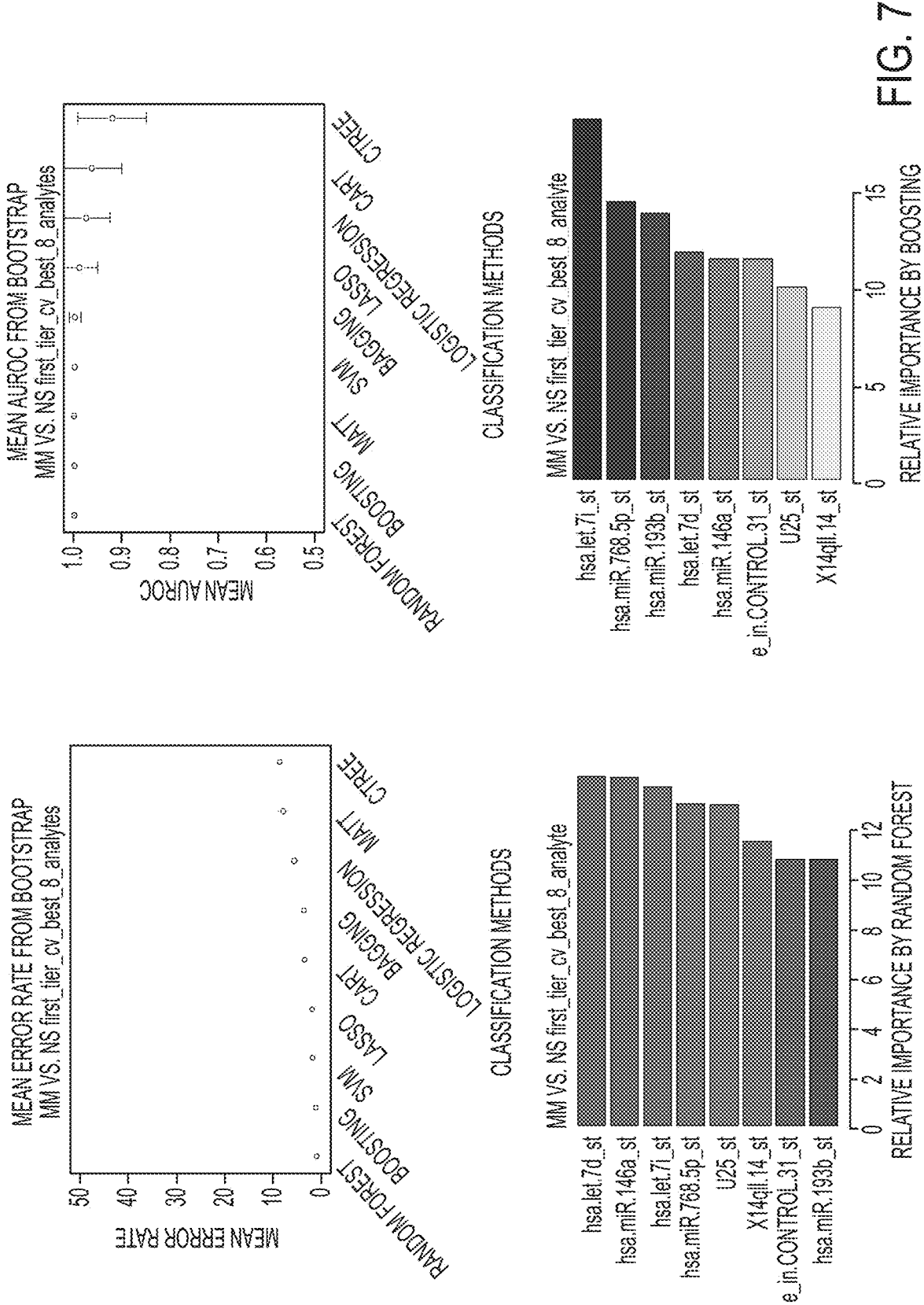
Figure 8:
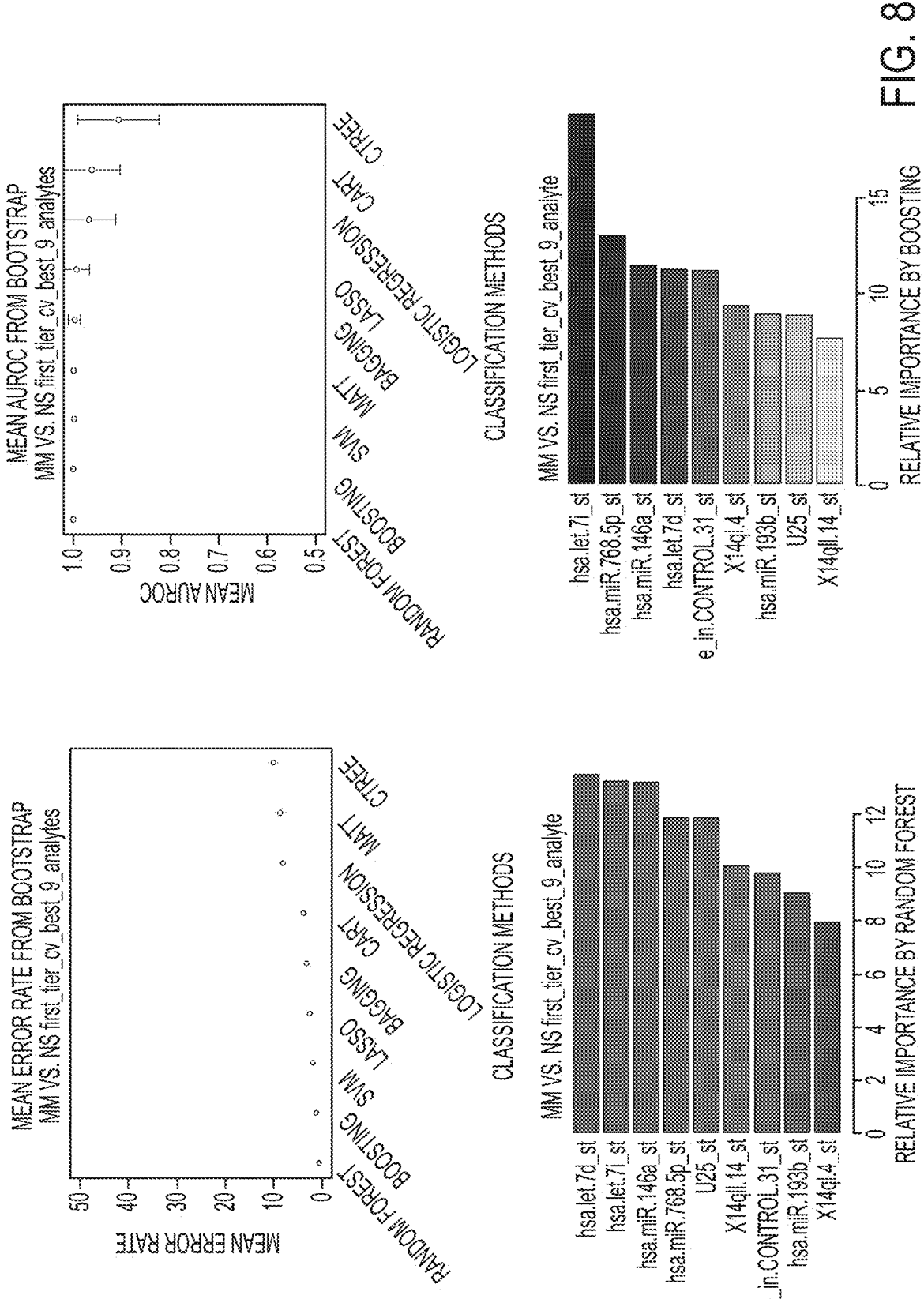
Figure 9:
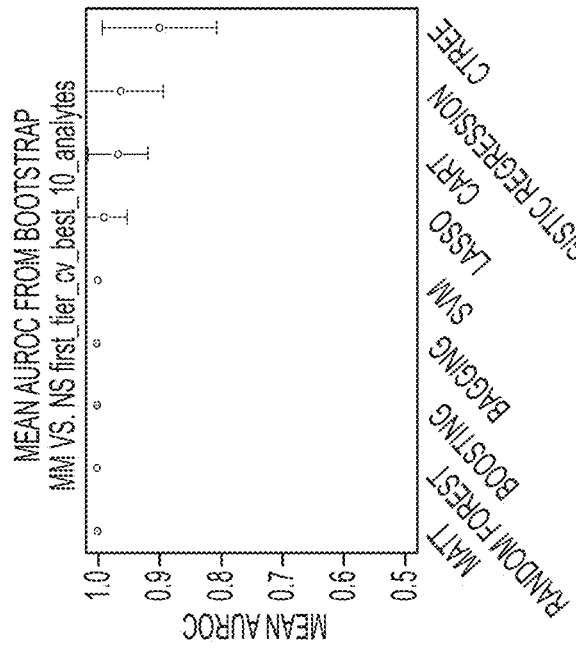
Figure 9:
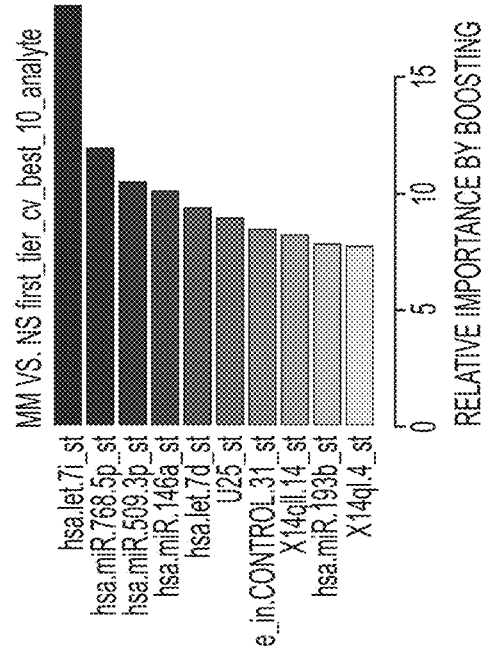
Figure 9:
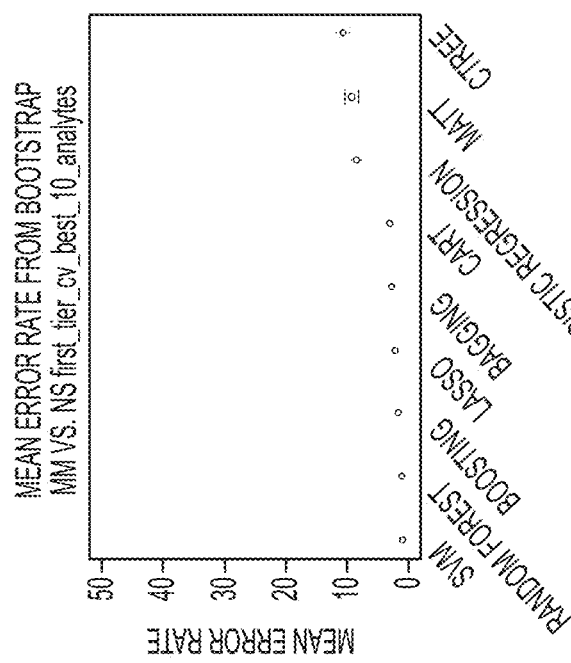
Figure 9:
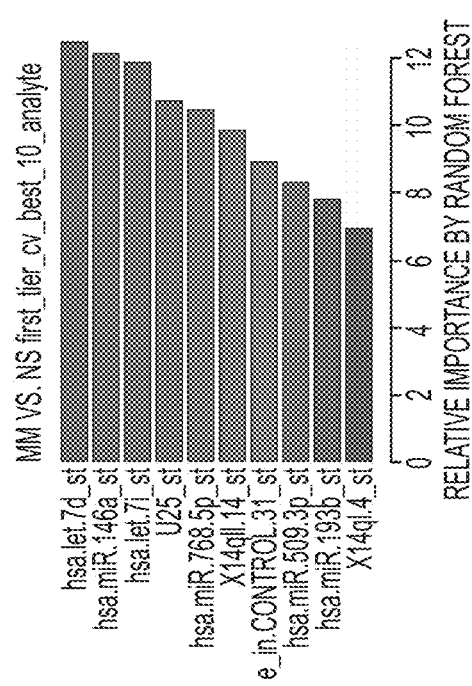
Figure 10:
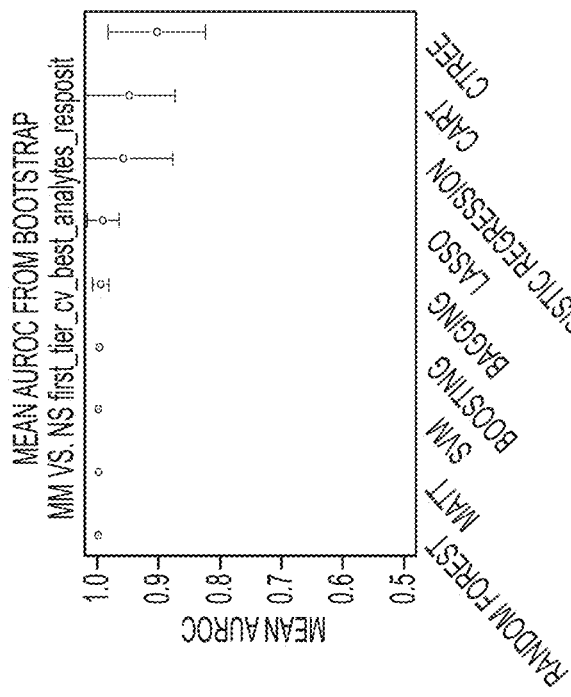
Figure 10:
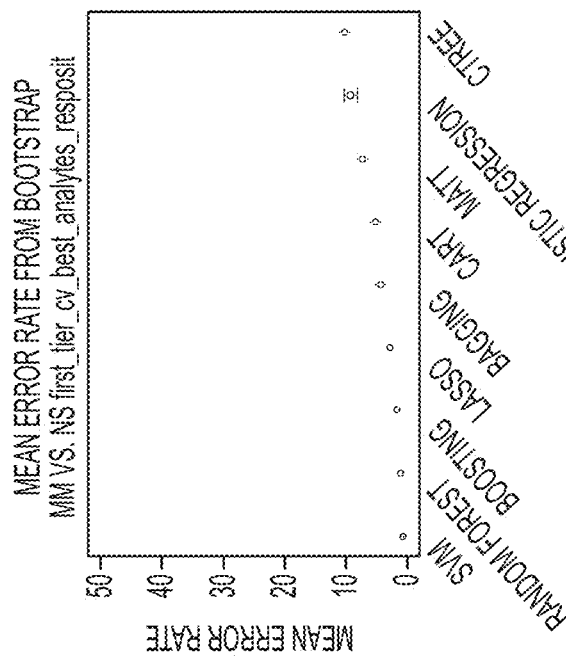
Figure 10:
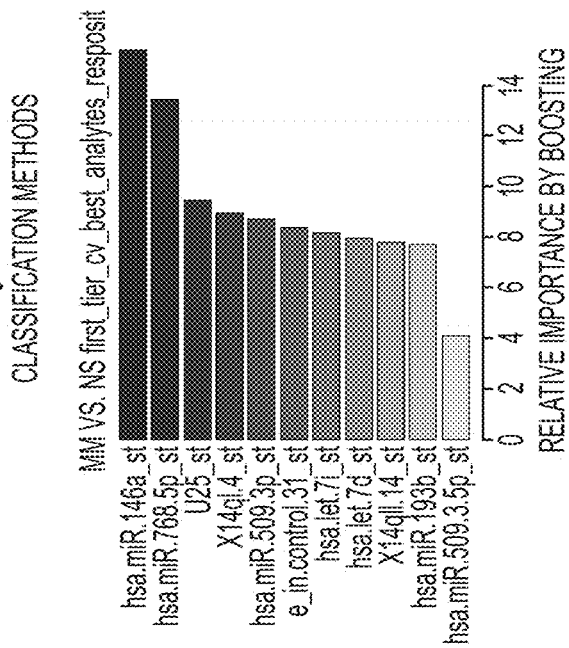
Figure 10:
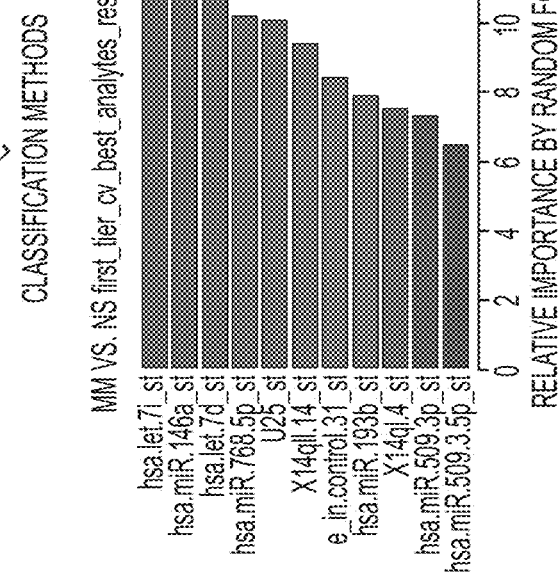
Figure 11:
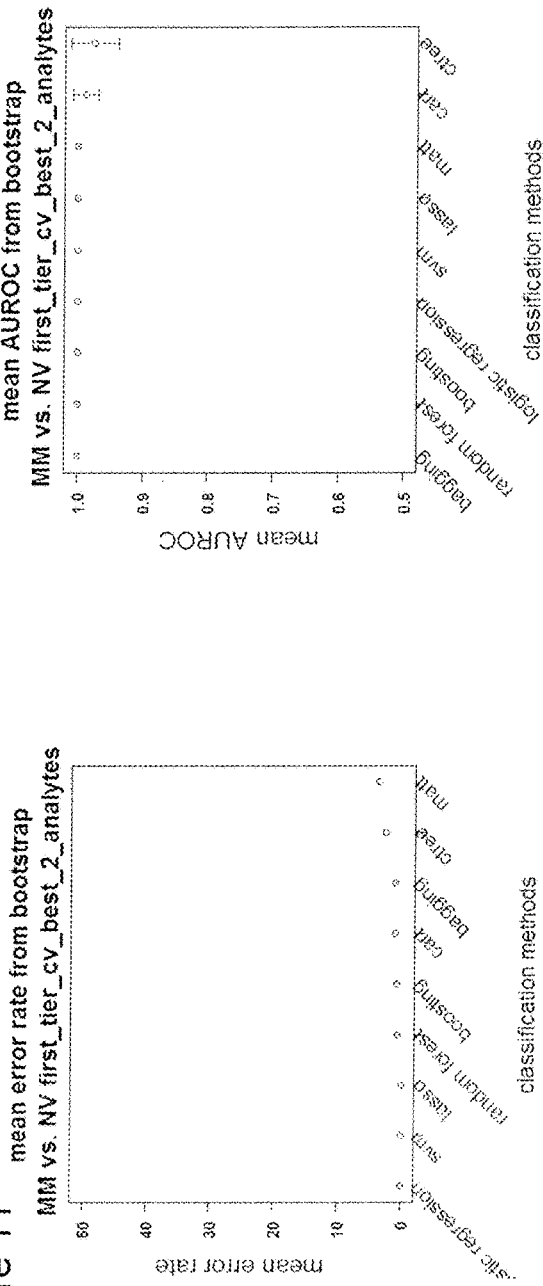
FIGS. 11-23 show, respectively, the best 2-14 miRNA combinations for differentiating melanoma (MM) from nevi (NV), and the relevant error rates and AUC, as determined by different statistical algorithms.
Figure 11:
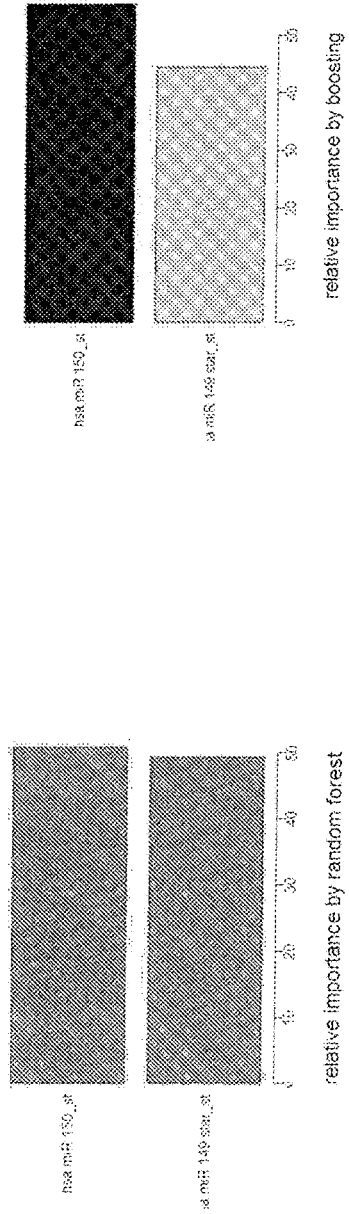
Figure 12:
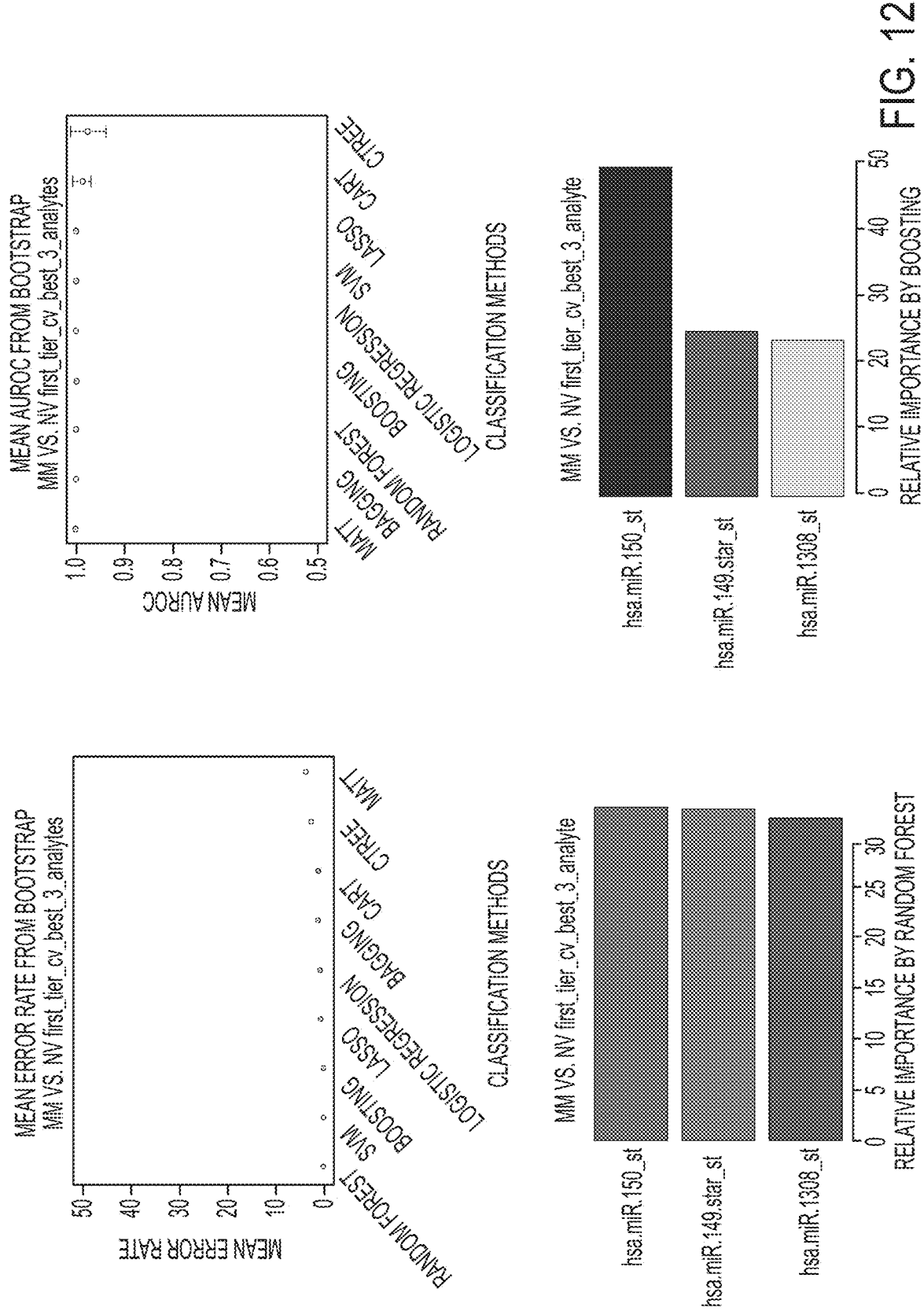
Figure 13:
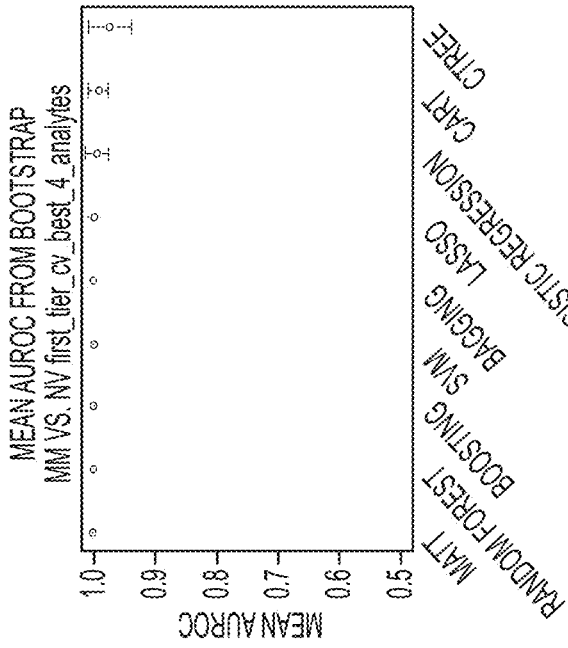
Figure 13:
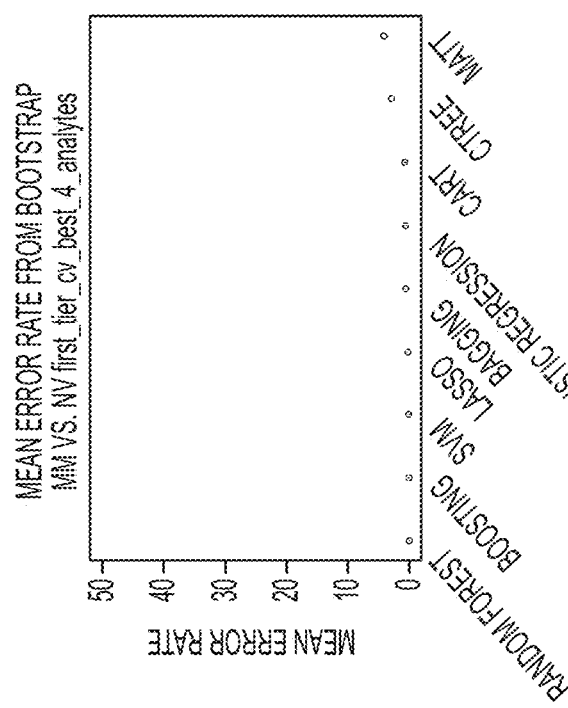
Figure 13:
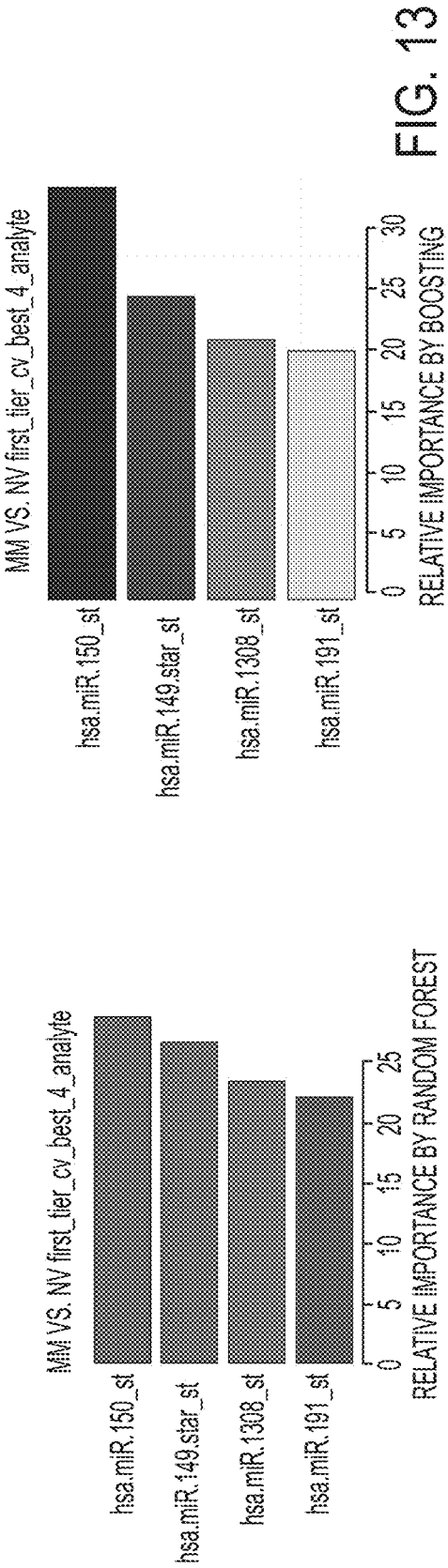
Figure 14:
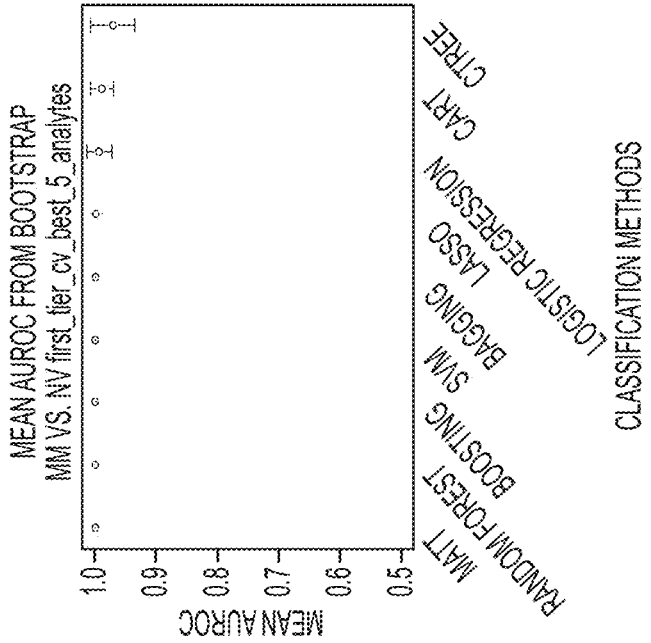
Figure 14:
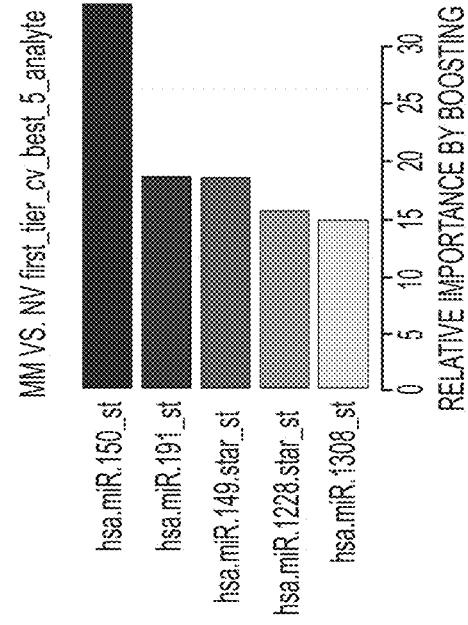
Figure 14:
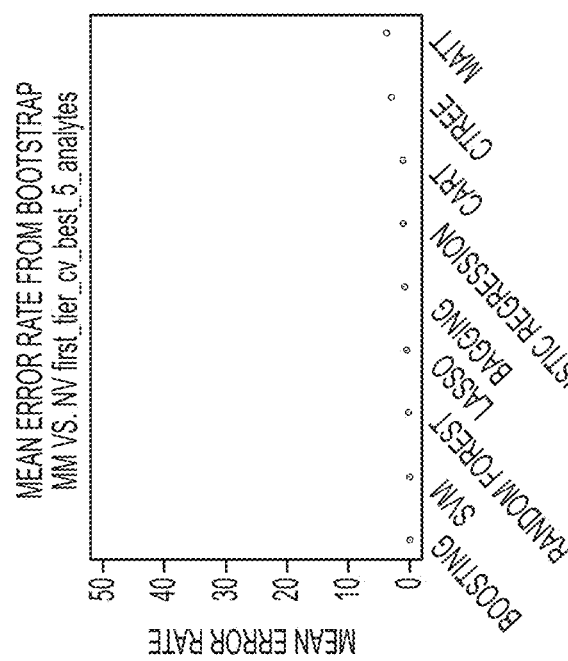
Figure 14:
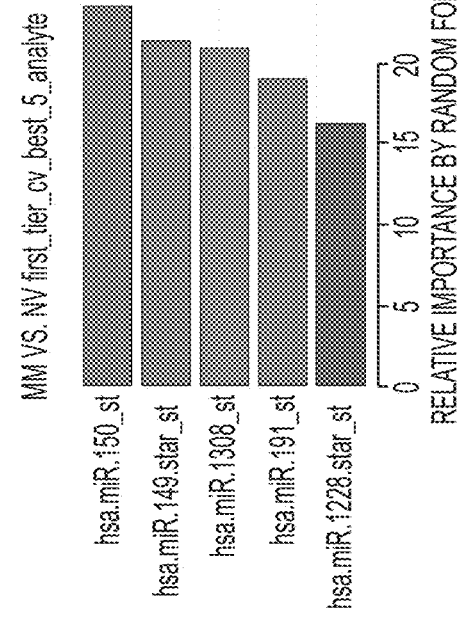
Figure 15:
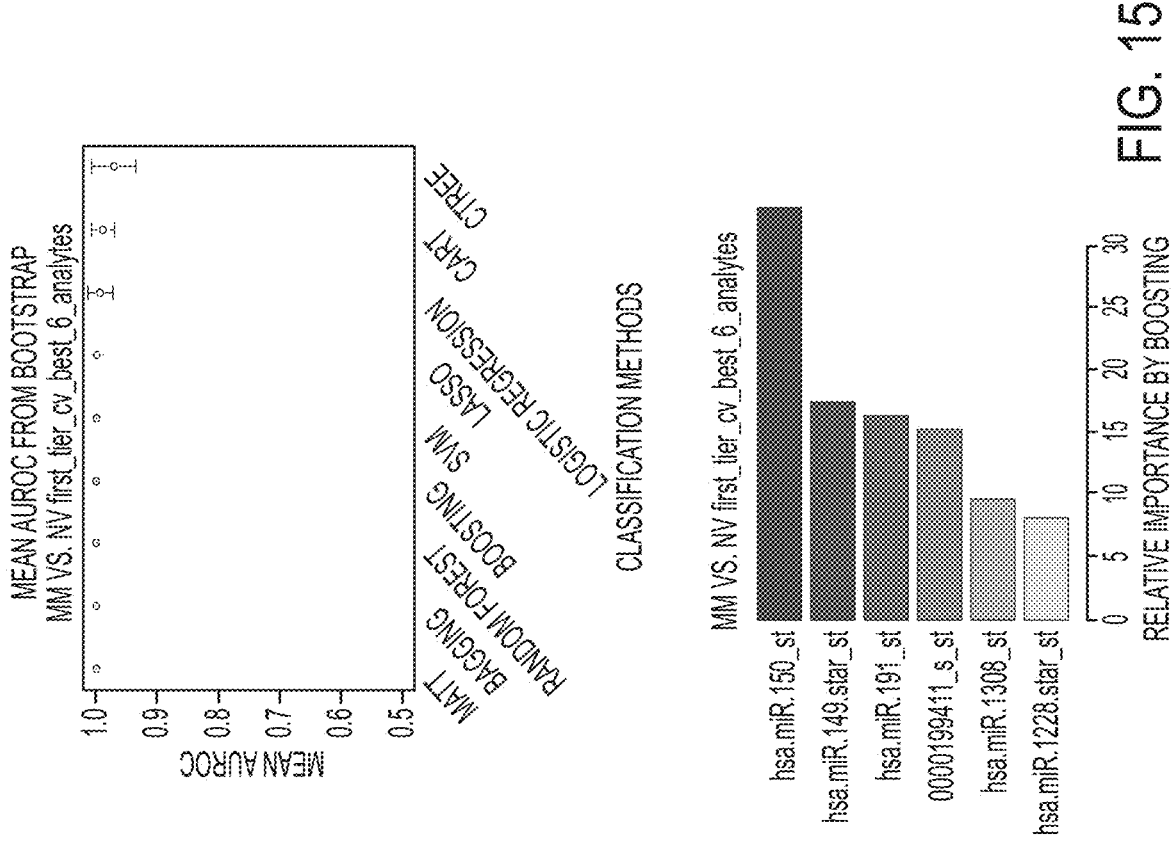
Figure 15:
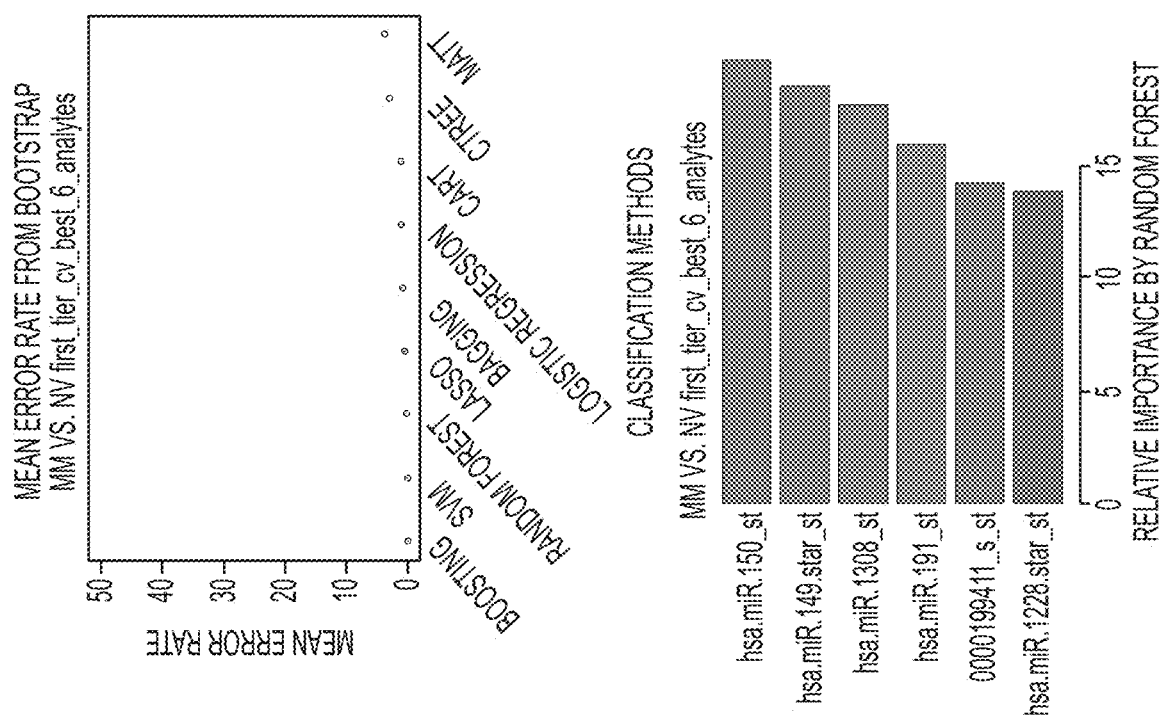
Figure 16:
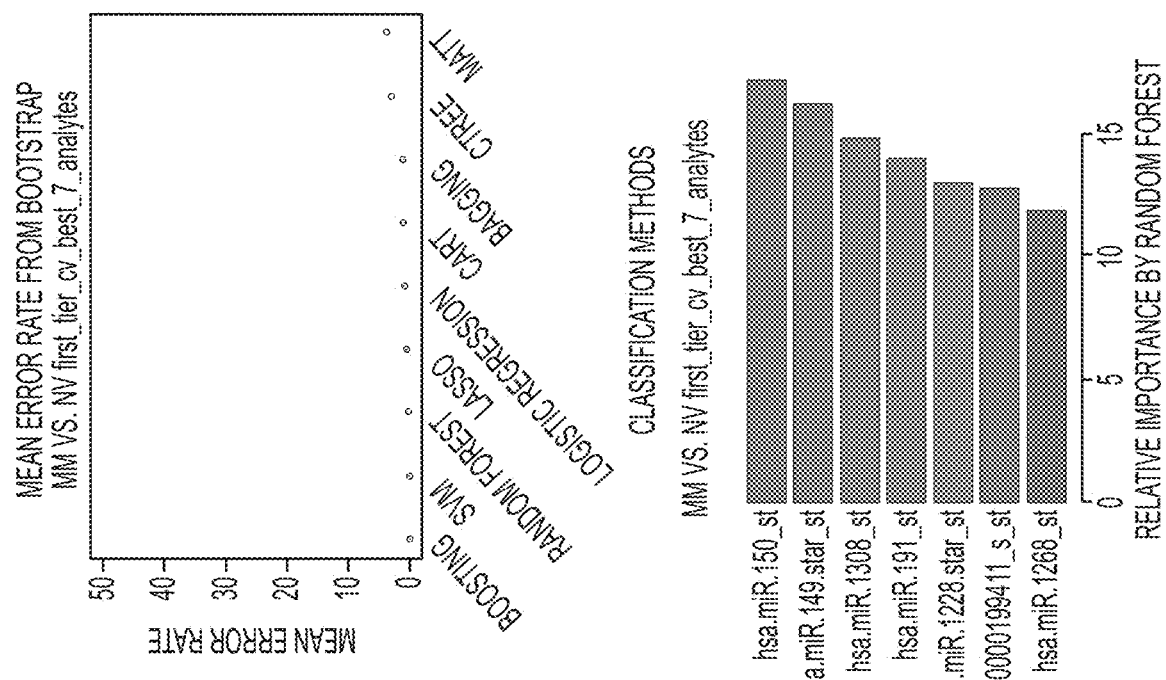
Figure 16:
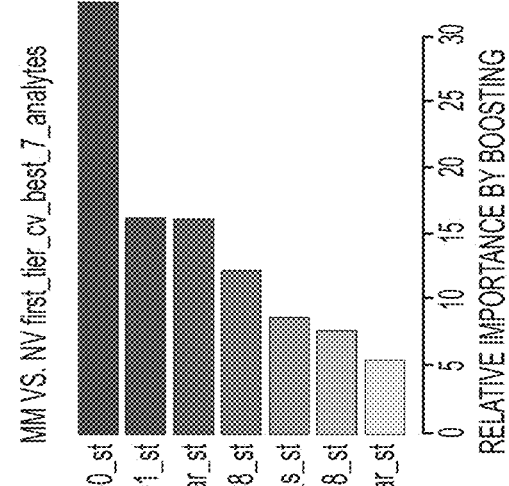
Figure 17:
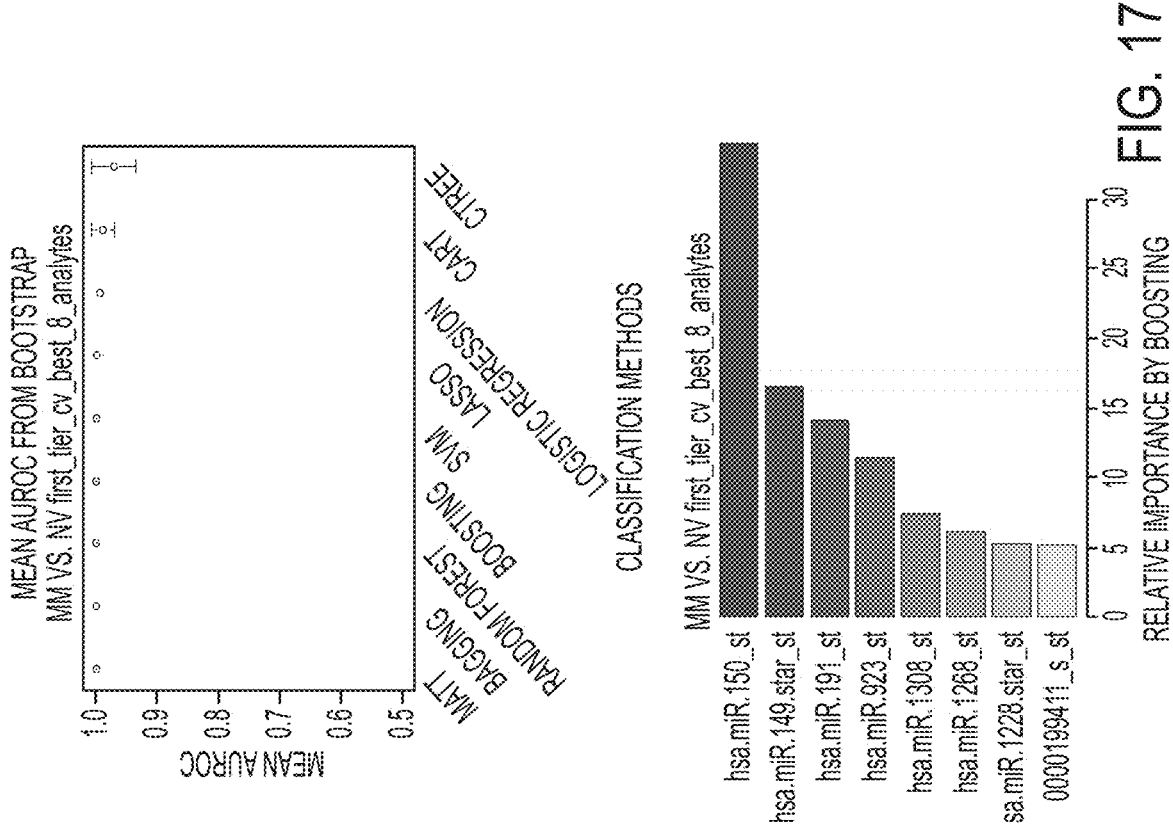
Figure 17:
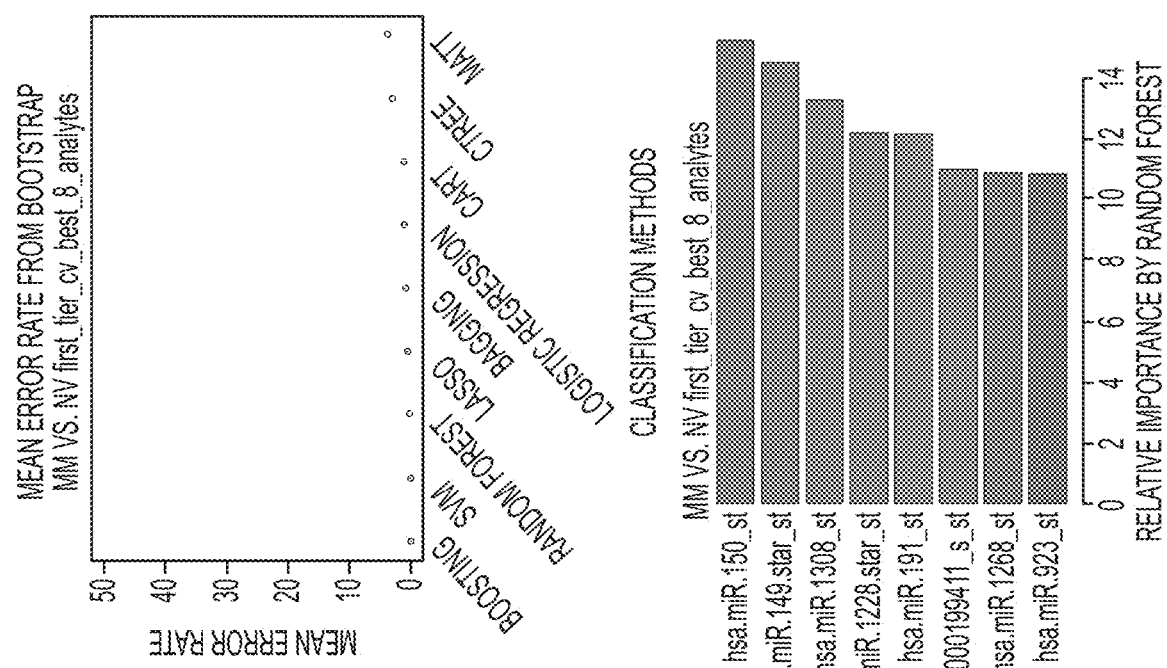
Figure 18:
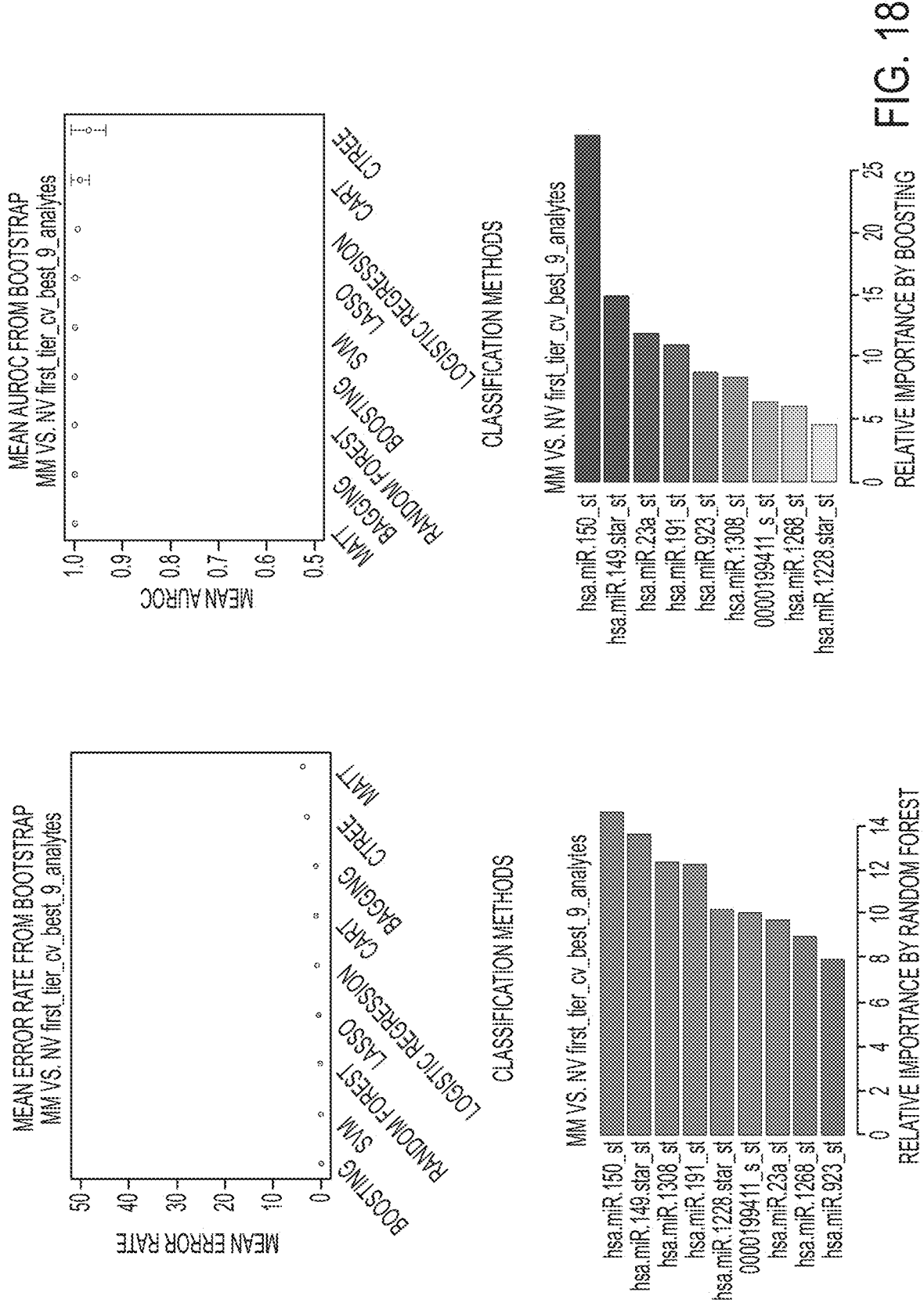
Figure 19:
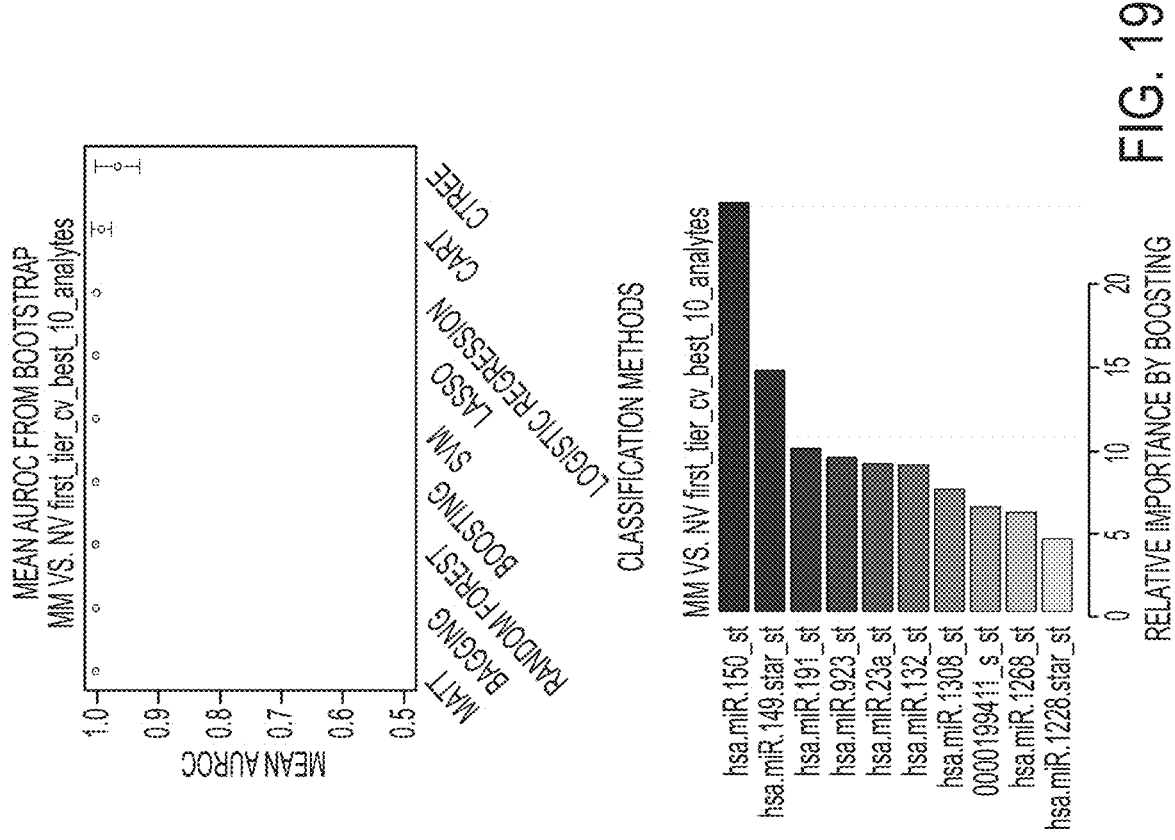
Figure 19:
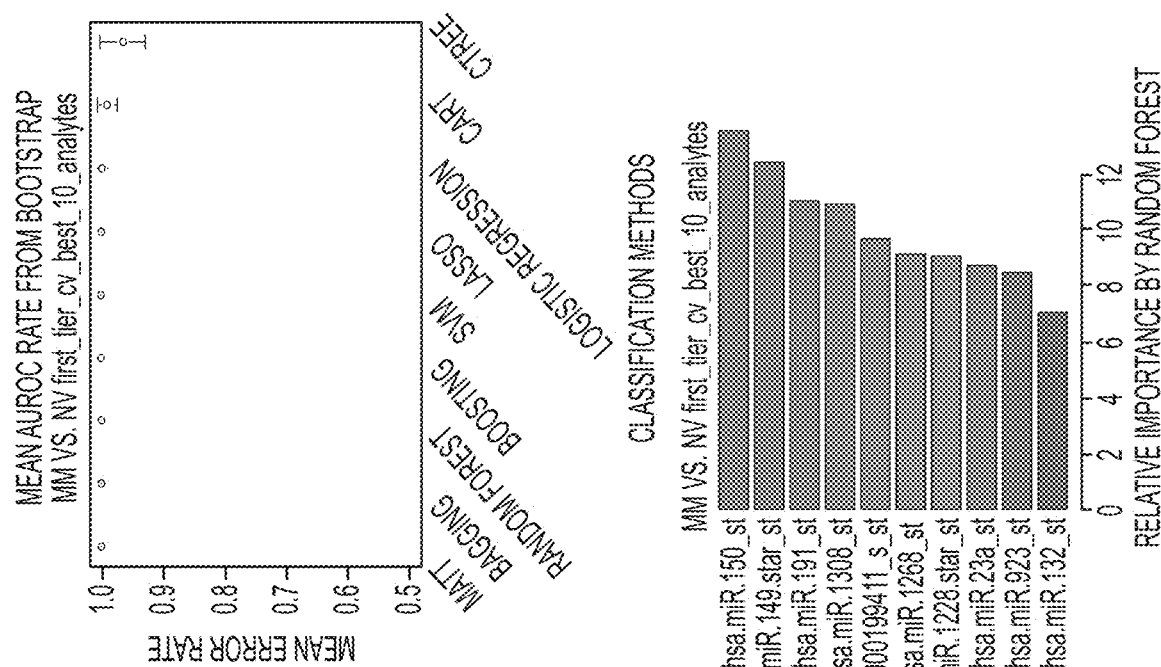
Figure 20:
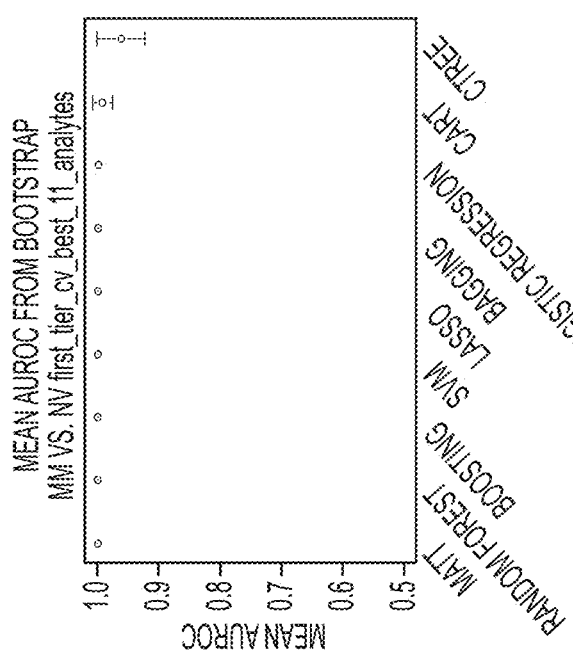
Figure 20:
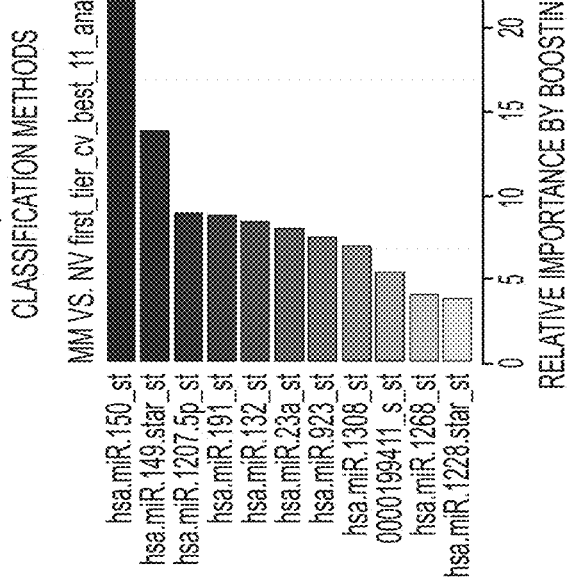
Figure 20:
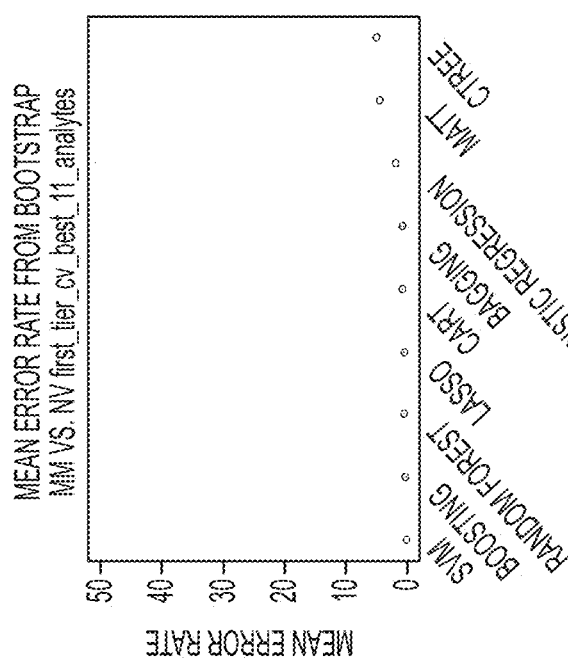
Figure 20:
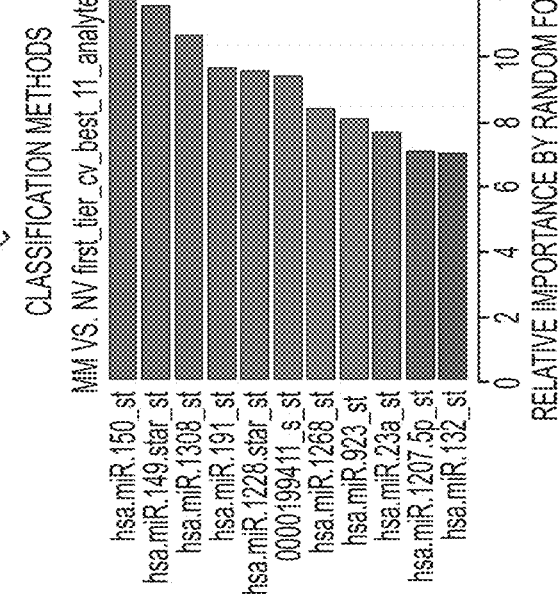
Figure 21:
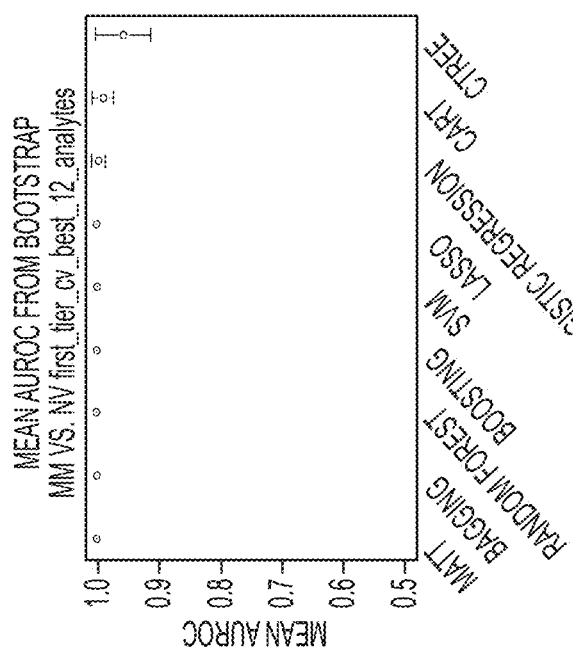
Figure 21:
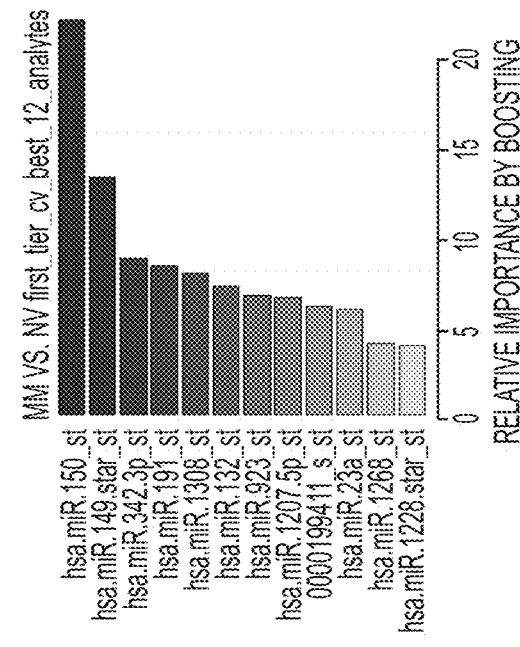
Figure 21:
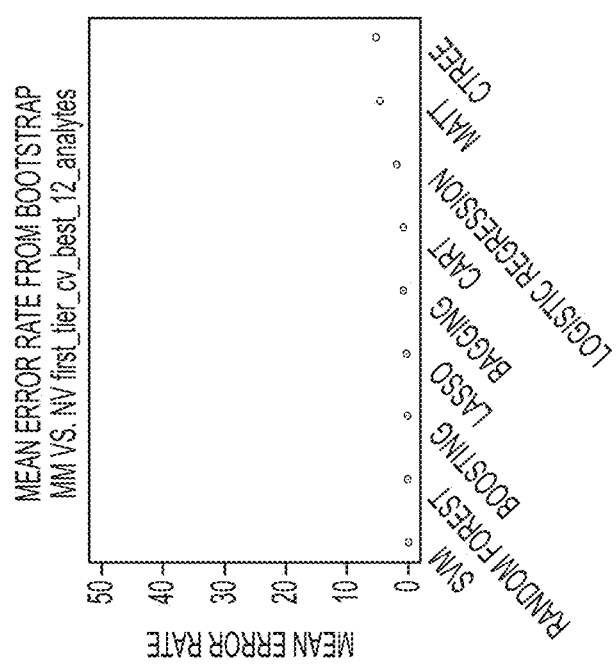
Figure 21:
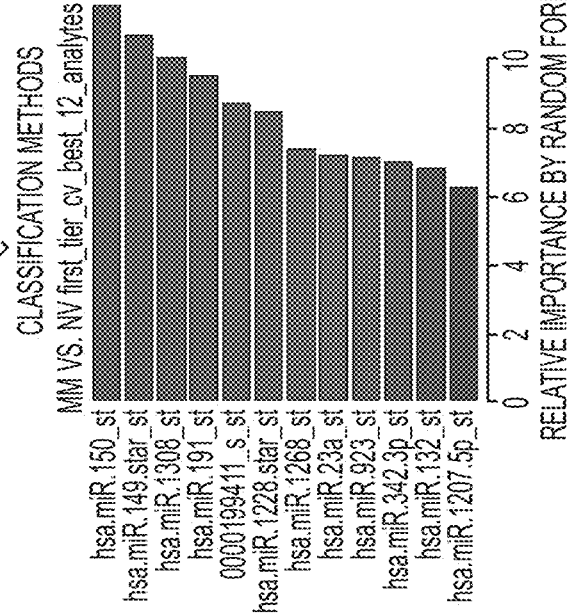
Figure 22:
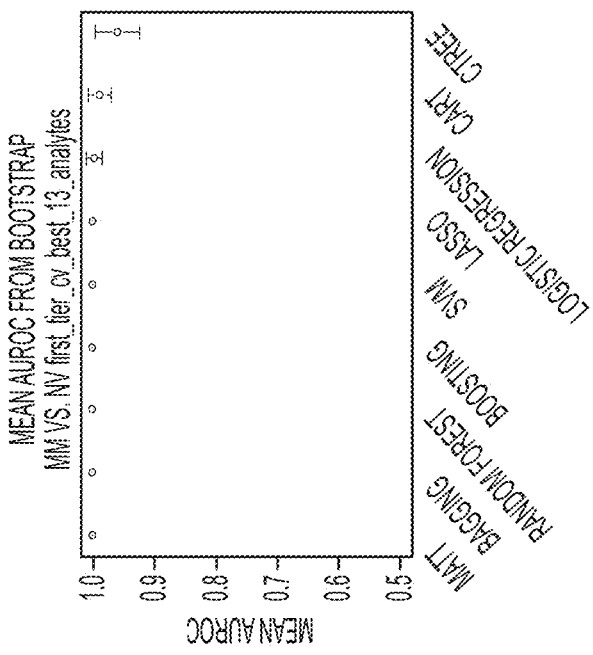
Figure 22:
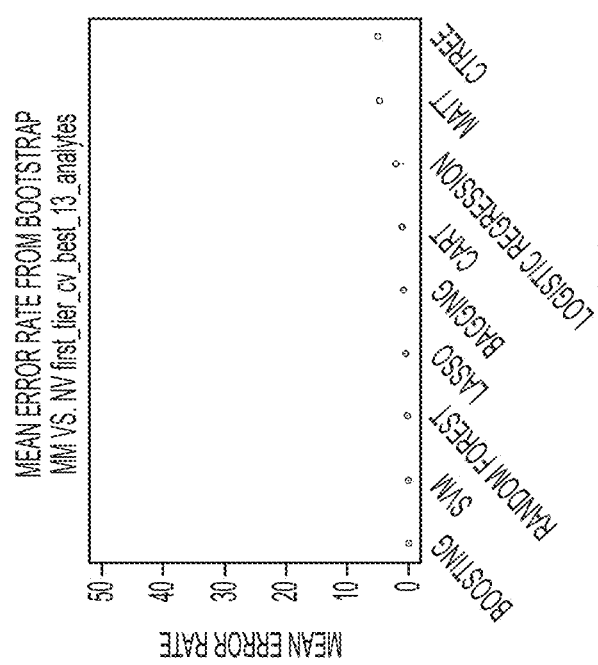
Figure 22:
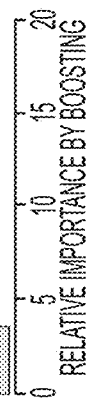
Figure 22:
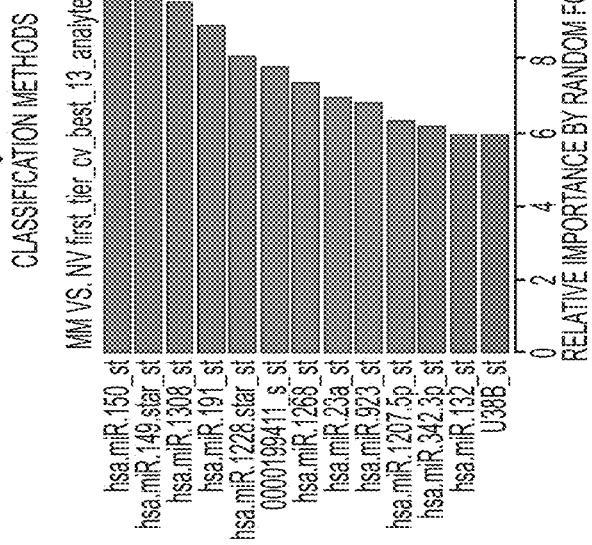
Figure 23:
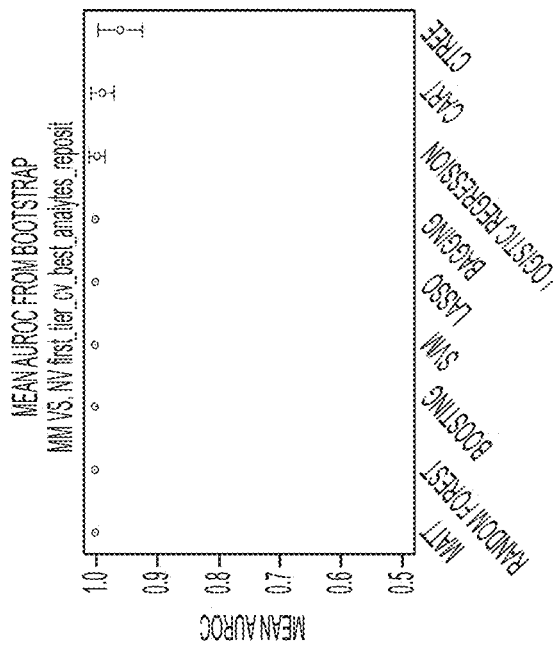
Figure 23:
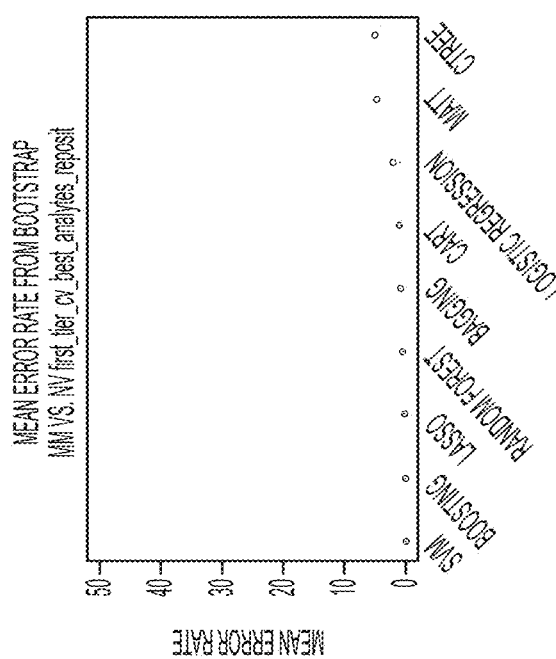
Figure 23:
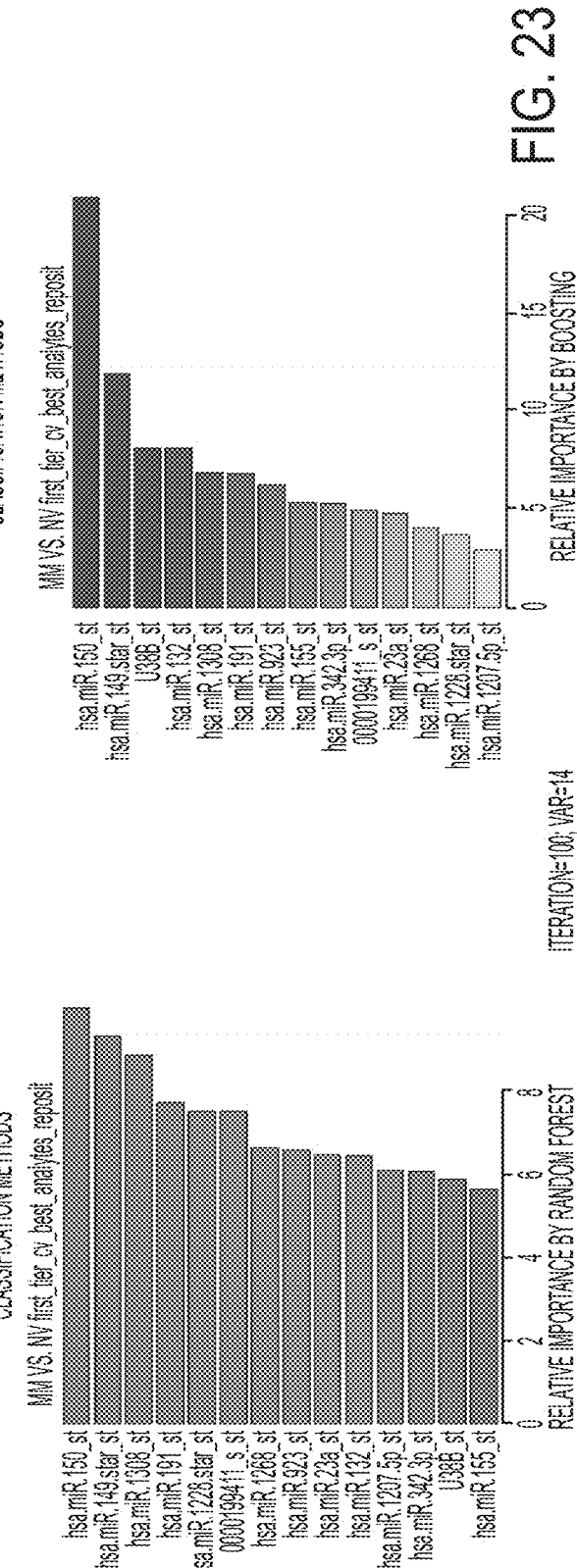

The present inventors have discovered that the levels of miRNAs in skin samples is a powerful tool to differentiate melanoma from non-tumorous nevi and, thereby, replace or supplement traditional clinical and histological methods of diagnosis.

Definitions

The present technology is described herein using several definitions, as set forth throughout the specification. As used herein, unless otherwise stated, the singular forms "a," "an," and "the" include plural reference. Thus, for example, a reference to "a nucleic acid" is a reference to one or more nucleic acids.

As used herein, "about" will be understood by persons of ordinary skill in the art and will vary to some extent depending upon the context in which it is used. If there are uses of the term which are not clear to persons of ordinary skill in the art, given the context in which it is used, the term "about" in reference to quantitative measurements or values will mean up to plus or minus 10% of the enumerated value.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, CA 1990, pp. 13-20; Wharam et al., *Nucleic Acids Res.,* 2001, 29(11):E54-E54; Hafner et al., *Biotechniques* 2001, 30(4):852-6, 858, 860; Zhong et al., *Biotechniques,* 2001, 30(4):852-6, 858, 860.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" includes determining the amount of something present, as well as determining whether it is present or absent.

The term "clinical factors" as used herein, refers to any data that a medical practitioner may consider in determining a diagnosis of melanoma. Such factors include, but are not limited to, the patient's medical history, age, gender, skin color, a physical examination of the patient, and histopathology.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

As used herein, the term "diagnosis" means detecting melanoma or the presence of melanoma cells. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical art for a particular disease or disorder, particularly melanoma.

As used herein, the phrase "difference of the level" refers to differences in the quantity of a particular marker, such as a nucleic acid or a protein, in a sample as compared to a control or reference level. For example, the quantity of a particular biomarker may be present at an elevated amount or at a decreased amount in samples of patients with a neoplastic disease compared to a reference level. In one embodiment, a "difference of a level" may be a difference between the quantity of a particular biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the quantity of a biomarker present in a sample as compared to a control. For example, a difference may be statistically significant if the measured level of the biomarker falls outside of about 1.0 standard deviations, about 1.5 standard deviations, about 2.0 standard deviations, or about 2.5 stand deviations of the mean of any control or reference group.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated. In some embodiments, the nucleic acid is isolated from the skin sample before further processing, such as PCR.

The term "label" as used herein, refers to any physical molecule directly or indirectly associated with a specific binding agent or antigen which provides a means for detection for that antibody or antigen. A "detectable label" as used herein refers any moiety used to achieve signal to measure the amount of complex formation between a target and a binding agent. These labels are detectable by spectroscopic, photochemical, biochemical, immunochemical, electromagnetic, radiochemical, or chemical means, such as fluorescence, chemifluorescence, or chemiluminescence, electrochemiluminescence or any other appropriate means. Suitable detectable labels include fluorescent dye molecules or fluorophores.

As used herein interchangeably, a "microRNA," "miR," or "miRNA" refers to the unprocessed or processed RNA transcript from a miRNA gene. MicroRNAs (miRNAs) are non-coding RNAs of 19-25 nucleotides in length that regulate gene expression by inducing translational inhibition or cleavage of their target mRNA through base pairing to partially or fully complementary sites. The unprocessed miRNA gene transcript is also called a "miRNA precursor," and typically comprises an RNA transcript of about 70-100 nucleotides in length. The miRNA precursor can be processed by digestion with an RNAse (for example, Dicer Argonaut, or RNAse III) into an active 19-25 nucleotide RNA molecule. This active 19-25 nucleotide RNA molecule is also called the "processed" miRNA gene transcript or "mature" miRNA As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, or reverse transcribed from sample DNA or RNA).

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are typically 15 to 70 nucleotides long, with 20 to 26 nucleotides being the most common. An oligonucleotide may be used as a primer or as a probe. An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

As used herein, the term "reference level" refers to a level of a substance which may be of interest for comparative purposes. In one embodiment, a reference level may be the miRNA levels expressed as an average of the level of miRNA from an area of normal skin or skin containing nevi and not melanoma. Nucleic acid samples may also be normalized relative to an internal control nucleic acid.

As used herein, the term "sample" refers to a skin biopsy from the subject, such at would typically be used for histopathological examination, or any section derived from such a sample. That is, a suspected melanoma may be entirely excised from the skin, but the biopsy is fixed and embedded in paraffin, and sectioned for further examination.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a subject who is, or is suspected to be, afflicted with melanoma.

The phrase "substantially the same as" in reference to a comparison of one value to another value for the purposes of clinical management of a disease or disorder means that the values are statistically not different. Differences between the values can vary, for example, one value may be within 20%, within 10%, or within 5% of the other value.

As used herein, the term "diagnostic score" refers to a single number or score, based on a statistical analysis of the measured level of one or more biomarkers that reflects a relationship of a specific subject to any one particular group of individuals, such as normal individuals or individuals having a disease or any progressive state thereof. In some embodiments, the diagnostic score is derived from a quantitative multivariate analysis, which reflects the overall statistical assessment of an individual patient's clinical condition based upon an integrated statistical calculation of a plurality of qualitatively unique factors, e.g., levels of diagnostic miRNA, combined with clinical presentation, etc.

Melanoma and Nevi

Nevus (or naevus, plural nevi or naevi, from naevus, Latin for "birthmark") is the medical term for sharply-circumscribed and chronic lesions of the skin. These lesions are commonly named birthmarks and moles. Nevi are benign by definition.

A melanocytic nevus (nevomelanocytic nevus, nevocellular nevus) is a benign proliferation of melanocytes, and are very common; almost all adults have at least one, usually more. A melanocytic nevus may be congenital or acquired.

A dysplastic nevus usually an acquired melanocytic nevus with abnormal features making it difficult to distinguish from a melanoma. It can be a marker for an individual at risk for developing melanomas.

Melanoma is a malignant tumor of melanocytes. Melanocytes predominantly occur in skin, between the outer layer of the skin (the epidermis) and the next layer (the dermis), but are also found in other parts of the body, including the bowel and the eye (see uveal melanoma). Melanoma can occur in any part of the body that contains melanocytes. Melanoma is less common than other skin cancers but is much more dangerous and causes the majority (75%) of deaths related to skin cancer Melanoma arises from DNA damage to melanocytes. The early stage of the disease is called the radial growth phase, and the tumour is less than 1 mm thick. Next is the invasive radial growth phase, when individual cells start to acquire invasive potential. The Breslow's depth of the lesion is usually less than 1 mm (0.04 in), the Clark level is usually 2. The following step is invasive melanoma, "vertical growth phase" (VGP). The tumour attains invasive potential, growing into the surrounding tissue and can spread around the body through blood or lymph vessels to form metastases. The tumour thickness is usually more than 1 mm (0.04 in), and the tumour involves the deeper parts of the dermis.

An immunological reaction against the tumour during the VGP may be judged by the presence and activity of the tumour infiltrating lymphocytes (TILs). These cells sometimes completely destroy the primary tumour, this is called regression, which is the latest stage of the melanoma development. In certain cases, the primary tumour is completely destroyed and only the metastatic tumour is discovered.

Melanoma may also have a genetic predisposition. Mutations in CDKN2A, CDK4, MCI R, MDM2 SNP309 and those associated with xeroderma pigmentosum (XP) predispose one to melanoma. Familial melanoma is genetically heterogeneous, [10] and loci for familial melanoma have been identified on the chromosome arms 1p, 9p and 12q. Multiple genetic events have been related to the pathogenesis (disease development) of melanoma.

Clinical and Pathological Diagnosis

Melanoma is usually first detected by visual examination of the skin, notably (A) asymmetry, (B) a border that is uneven, ragged, or notched, (C) coloring of different shades of brown, black, or tan and (D) diameter that had changed in size. Normal moles are symmetrical, have an even border, even color, and no change in diameter. The main concern is distinguishing between a benign nevus, a dysplastic nevus, and a melanoma. Moles that are irregular in color or shape are often treated as candidates of melanoma. Following a visual examination and a dermatoscopic exam, or in vivo diagnostic tools such as a confocal microscope, a sample (biopsy) of the suspicious mole may be obtained.

Sample Preparation

When an atypical mole has been identified, a skin biopsy takes place in order to best diagnose it. Local anesthetic is used to numb the area, then the mole is biopsied. The biopsy material is then sent to a laboratory to be evaluated by a pathologist. A skin biopsy can be a punch, shave, or complete excision. The complete excision is the preferred method, but a punch biopsy can suffice if the patient has cosmetic concerns (i.e. the patient does not want a scar) and the lesion is small. A scoop or deep shave biopsy is often advocated, but should be avoided due to risk of a recurrent nevus, which can complicate future diagnosis of a melanoma, and the possibility that resulting scar tissue can obscure tumor depth if a melanoma is found to be present and re-excised.

Most dermatologists and dermatopathologists use a system devised by the NIH for classifying melanocytic lesions. In this classification, a nevus can be defined as benign, having atypia, or being a melanoma. A benign nevus is read as (or understood as) having no cytologic or architectural atypia. An atypical mole is read as having architectural atypia, and having (mild, moderate, or severe) cytologic (melanocytic) atypia. Usually, cytologic atypia is of more important clinical concern than architectural atypia. Usually, moderate to severe cytologic atypia will require further excision to make sure that the surgical margin is completely clear of the lesion.

The most important aspect of the biopsy report is that the pathologist indicates if the margin is clear (negative or free of melanocytic nevus), or if further tissue (a second surgery) is required. If this is not mentioned, usually a dermatologist or clinician will require further surgery if moderate to severe cytologic atypia is present—and if residual nevus is present at the surgical margin.

miRNA Markers to Distinguish Nevi from Melanoma

Distinguishing nevi from melanoma requires a high degree of skill. Misdiagnosis of a melanoma as a nevus can result in delay in treatment, which can be lethal because melanoma is an aggressive cancer that requires prompt intervention. Conversely, incorrectly identifying a nevus as a melanoma may subject a patient to aggressive treatment that is unnecessary and harmful. The present inventors have established that melanoma may be distinguished from nevi by monitoring the levels of select miRNA.

The methods described herein can distinguish melanoma, normal skin, nevi and malignant melanoma. Most importantly, the method is suitable for differentiating nevi from melanoma, and therefore fill a need for diagnosis that it not fully met by histology. As such, the methods of the invention can replace, supplement, or confirm histology. A particular advantage of the methods of the invention is that they provide independent objective evidence.

An additional advantage of the invention is that they can be performed on formalin fixed paraffin embedded (FFPE) tissue, and therefore can be used on the same samples that are processed for standard histopathological examination, and thus do not require a separate sample, or special handling. Another advantage is that the inventors have found that the miRNAs are stable in FFPE tissue and can be detected some time after fixing and embedding.

Another advantage of the invention is that the mRNA's chosen do not require a relatively pure sample of melanoma cells, and can detect melanoma in a sample that also contains normal skin, nevi and other skin cells. Thus, the miRNA assay is not overly sensitive to contamination nor require special handling beyond that which is normally used for preparation of FFPE tissue for regular histology.

The inventors have identified 50 miRNAs that can readily distinguish melanoma from nevi. Through statistical modeling and analysis, groups of the best 2, 3, 4, 5, 6, 7, 8, 9, 10, 11, 12, 13 and 14 markers have been identified. An increase in the number of markers used may improve sensitivity and accuracy, but comes with increased cost and complexity.

Additional diagnostic markers may be combined with the miRNA measurements to further aid diagnosis. For example, the clinical and/or histopathological results can be converted into a score, which is then combined with a score derived from the miRNA data. The combination of scores can be used to obtain a single "diagnostic score" that reflects the likelihood of melanoma.

Nucleic Acid Extraction and Detection

The level of a miRNA gene product in a sample can be measured using any technique that is suitable for detecting RNA expression levels in a biological sample. Suitable techniques for determining RNA expression levels in a biological sample are well known to those of skill in the art. These include, for example, Northern blot analysis. RT-PCR, and in situ hybridization.

The nucleic acid to be detected may be from a biological sample such as a tissue sample and the like. Various methods of extraction are suitable for isolating the DNA or RNA. Suitable methods include phenol and chloroform extraction. See Maniatis et al., *Molecular Cloning, A Laboratory Manual*, 2d, Cold Spring Harbor Laboratory Press, pp. 16-54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France). In an illustrative embodiment, RNA is isolated from patient serum on the NucliSens easyMAG system (Biomeriux SA, France) according to the manufacturer's protocol.

In one embodiment, the level of at least one miRNA gene product is detected using Northern blot analysis. For example, total RNA can be purified from a sample in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, *Molecular Cloning: A Laboratory Manual*, J. Sambrook et al., eds., 2nd edition, Cold Spring Harbor Laboratory Press, 1989, Chapter 7.

Suitable probes (e.g., DNA probes or RNA probes) for Northern blot hybridization of a given miRNA gene product can be produced from the known nucleic acid sequences and include, but are not limited to, probes having at least about 70%, 75%, 80%, 85%, 90%, 95%, 98% or 99% complementarity to a miRNA gene product of interest, as well as probes that have complete complementarity to a miRNA gene product of interest. Methods for preparation of labeled DNA and RNA probes, and the conditions for hybridization thereof to target nucleotide sequences, are described in *Molecular Cloning: A Laboratory Manual*, J. Sambrook et al., eds., 2nd edition. Cold Spring Harbor Laboratory Press. 1989, Chapters 10 and 11.

For example, the nucleic acid probe can be labeled with, e.g., a radionuclide, such as $^3H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like. Probes can be labeled to high specific activity by either the nick translation method or by the random priming method. Autoradiographic detection of hybridization can then be performed by exposing hybridized filters to photographic film. Densitometric scanning of the photographic films exposed by the hybridized filters provides an accurate measurement of miRNA levels. Using another approach, miRNA gene transcript levels can be quantified by computerized imaging systems.

In one embodiment, the miRNA is detected using a nucleic acid amplification process. Nucleic acid extracted from a sample can be amplified using nucleic acid amplification techniques well known in the art. By way of example, but not by way of limitation, these techniques can include the polymerase chain reaction (PCR), reverse transcriptase polymerase chain reaction (RT-PCR), nested PCR, ligase chain reaction. See Abravaya, K., et al., *Nucleic Acids Research*, 23:675-682, (1995), branched DNA signal amplification, Urdea, M. S., et al., *AIDS*, 7 (suppl 2): S11-S14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., *J Virological Methods*, 35:273-286, (1991), Invader Technology, or other sequence replication assays or signal amplification assays may also be used.

Some methods employ reverse transcription of RNA to cDNA. The method of reverse transcription and amplification may be performed by previously published or recommended procedures. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus thermophilus*. For example, one method which may be used to convert RNA to cDNA is the protocol adapted from the Superscript II Preamplification system (Life Technologies, GIBCO BRL, Gaithersburg, Md.; catalog no. 18089-011), as described by Rashtchian, A., *PCR Methods Applic.*, 4:S83-S91, (1994).

In a suitable embodiment. PCR is used to amplify a target sequence of interest. PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan et al., *J of Clin Micro,* 33(3):556-561 (1995). Briefly, a PCR reaction mixture includes two specific primers, dNTPs, approximately 0.25 U of Taq polymerase, and 1×PCR Buffer.

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity.

In some embodiments, the amplification may include a labeled primer or probe, thereby allowing detection of the amplification products corresponding to that primer or probe. In particular embodiments, the amplification may include a multiplicity of labeled primers or probes; such primers may be distinguishably labeled, allowing the simultaneous detection of multiple amplification products. Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled.

In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, Dabcyl, or Black Hole Quencher® (BHQ), especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak el al., 1995. *PCR Method Appl.,* 4:357-362; Tyagi et al, 1996. *Nature Biotechnology,* 14:303-308; Nazarenko el al., 1997, *Nucl. Acids Res.,* 25:2516-2521; U.S. Pat. Nos. 5,866, 336 and 6,117,635).

Nucleic acids may be amplified prior to detection or may be detected directly during an amplification step (i.e., "real-time" methods). For example, amplified fragments may be detected using standard gel electrophoresis methods. In some embodiments, amplified fractions are separated on an agarose gel and stained with ethidium bromide by methods known in the art to detect amplified fragments. In some embodiments, the target sequence is amplified using a labeled primer such that the resulting amplicon is detectably labeled. In some embodiments, the primer is fluorescently labeled.

In one embodiment, detection of a miRNA, such as a nucleic acid from an a miR-16 or miR-199a, is performed using the TaqMan® assay, which is also known as the 5' nuclease assay (U.S. Pat. Nos. 5,210,015 and 5,538,848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target-containing template which is amplified during PCR.

TaqMan® primer and probe sequences can readily be determined using the nucleic acid sequence information of the miRNA of interest. A number of computer programs, such as Primer Express (Applied Biosystems, Foster City, CA), can be used to rapidly obtain optimal primer/probe sets. It will be apparent to one of skill in the art that such primers and probes for detecting the target nucleic acids are useful in diagnostic assays for neoplastic disorders, such as HCC, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866, 336 and 6,117,635).

In an illustrative embodiment, real time PCR is performed using TaqMan® Assays in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Real-time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually. The Ct can be correlated to the initial amount of nucleic acids or number of starting cells using a standard curve.

In one embodiment, TaqMan® MicroRNA Assays are used to detect the miRNA. TaqMan® MicroRNA Assays are predesigned assays that are available for the majority of content found on the miRBase miRNA sequence repository. In another embodiment, the mirVana® qRT-PCR miRNA Detection Kit (Ambion) is a used to detect and quantify the miRNA. This is a quantitative reverse transcription-PCR (qRT-PCR) kit enabling sensitive, rapid quantification of miRNA (miRNA) expression from total RNA samples.

As a quality control measure, an internal amplification control may be included in one or more samples to be extracted and amplified. The skilled artisan will understand that any detectable sequence that is not typically present in the sample can be used as the control sequence. A control sequence can be produced synthetically. If PCR amplification is successful, the internal amplification control amplicons can then be detected. Additionally, if included in the sample prior to purification of nucleic acids, the control sequences can also act as a positive purification control.

Statistical Methods

Statistical methods can be used to set thresholds for determining when the level in a subject can be considered to be different than or similar to a reference level. In addition, statistics can be used to determine the validity of the difference or similarity observed between a patient's circulating miRNA level and the reference level. Useful statistical analysis methods are described in L. D. Fisher & G. vanBelle, Biostatistics: *A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05. As used herein a "confidence interval" or "CI" refers to a measure of the precision of an estimated or calculated value. The interval represents the range of values, consistent with the data that is believed to encompass the "true" value with high probability (usually 95%). The confidence interval is expressed in the same units as the estimate or calculated value. Wider intervals indicate lower precision; narrow intervals indicate greater precision. Preferred confidence intervals of the invention are 90%, 95%, 97.5%, 98%, 99%, 99.5%, 99.9% and 99.99%. A "p-value" as used herein refers to a measure of probability that a difference between groups happened by chance. For example, a difference between two groups having a p-value of 0.01 (or p=0.01) means that there is a 1 in 100 chance the result occurred by chance. Preferred p values are 0.1, 0.05, 0.025, 0.02, 0.01, 0.005, 0.001, and 0.0001. Confidence intervals and p-values can be determined by methods well-known in the art. See, e.g., Dowdy and Wearden, *Statistics for Research*, John Wiley & Sons, New York, 1983.

On linear model for assessing differential expression in microarray experiments: Smith G K (2004) "Linear models and empirical bayes method for assessing differential expression in microarray experiments" *Statistical Applications in Genetics and Molecular Biology*. For AUC calculation: Mason S J and Graham N E (1982) "Areas beneath the relative operating characteristics (ROC) and relative operating levels (ROL) curves: Statistical significance and interpretation," *Q.J.R. Meteorol. Soc.* textbf30 291-303. Multiple algorithms program for marker combination selection: An R based program with nine algorithms including random forest, ada boosting, svm, bagging, logistic regression, lasso, matt, cart, etree is available, for example, as open-source software from the R Foundation. Random forests were also conducted according to Breiman, L. (2001), *Random Forests*, Machine Learning 45(1), 5-32. See also Breiman, L (2002). "Manual On Setting Up, Using, And Understanding Random Forests V3.1.

In connection with miRNA used to diagnose melanoma, one may seek levels that are lower or higher than a control. The term "elevated levels" or "higher levels" as used herein refers to levels of an miRNA that are higher than what would normally be observed in a comparable sample from control or normal subjects or normal tissue from the patient (i.e., a reference value). Similarly, "reduced levels" or "lower levels" as used herein refer to levels of that are lower than what would normally be observed in a comparable sample from control or normal subjects, or normal tissue from the patient (i.e., a reference value). In some embodiments, "control levels" (i.e., normal levels) refer to a range of miRNA levels that would be normally be expected to be observed in nevi, or normal skin. A control level may be used as a reference level for comparative purposes. The ranges accepted as outside "control levels" are dependent on a number of factors. For example, one laboratory may routinely determine the level of circulating miRNA in a sample that is different than the miRNA obtained for the same sample by another laboratory. Also, different assay methods may achieve different value ranges. Value ranges may also differ in various sample types, for example, different body fluids or by different treatments of the sample. One of ordinary skill in the art is capable of considering the relevant factors and establishing appropriate reference ranges for "control values" and "elevated/reduced values" of the present invention. For example, a series of samples from control subjects and subjects diagnosed with melanoma can be used to establish ranges that are "normal" or "control" levels and ranges that are "elevated" or "reduced" than the control range.

The level of one or more miRNAs measured in the test sample is normalized, such as by comparison to an internal reference nucleic acid, e.g., U44 or small RNA U6. The levels of the one or more miRNAs may then be compared to a reference value to determine if the levels of the one or more miRNAs are elevated or reduced relative to the reference value. Typically, the reference value is the level measured in a comparable sample from one or more healthy individuals. An increase or decrease in the level of the one or more miRNAs may be used in conjunction with clinical factors to diagnose melanoma.

In some embodiments, the level of one or more miRNAs is combined with one or more additional markers to improve diagnostic sensitivity and specificity. Exemplary markers include, but are not limited to, any useful diagnostic marker associated with melanoma including those which may be assessed by fluorescence in-situ hybridization (FISH) and/or comparative genomic hybridization (CGH).

Kits

A kit may be used for conducting the diagnostic and prognostic methods described herein. Typically, the kit should contain, in a carrier or compartmentalized container, reagents useful in any of the above-described embodiments of the diagnostic method. The carrier can be a container or support, in the form of, e.g., bag, box, tube, rack, and is optionally compartmentalized. The carrier may define an enclosed confinement for safety purposes during shipment and storage. In one embodiment, the kit includes one or more PCR primers capable of amplifying miRNA selected from miR-132, miR-150, miR-339-5p, miR-15b, miR-342-3p, miR-572, miR-155, miR-425, miR-1202, miR-1268, HBII-382_s, miR-1225-5p, miR-30c, miR-106b-star, miR-125a-5p, mgU6-53B, miR-25, miR-149-star, miR-939, miR- 92b-star, miR-500-star, miR-22, HBII-142_x, miR-181b, HBII-142, U38B, miR-663, miR-1224-5p, miR-23a, HBII-85-6_x, miR-1207-5p, miR-1301, miR-1228-star, miR-345, miR-30a-star. ENSG00000199411_s, ENSG00000202327, miR-92a, miR-127-3p, HBII-85-26, miR-1308, miR-31, miR-921, miR-146b-5p, miR-768-3p, miR-708, miR-139-5p, ACA24_x, miR-501-3p, miR-502-3p, miR-923, and miR-191.

In further embodiments, the invention comprise a kit. In one embodiment, a kit for differentially diagnosing between melanoma and nevus in a skin sample comprises primers for the amplification of at least two miRNA selected from the group consisting of: miR-150, miR-149-star, miR-1308; miR-191; miR-1228-star; ENSG00000199411_s; miR-1268; miR-923; miR-23a; miR-132; miR-1207.5p; miR-342.3p; U38B; and miR-155.

In another embodiment, the kit comprises primers for the amplification of at least two miRNAs selected from the group consisting of: miR-1268, miR-1228-star, miR-92b-star, miR-155, miR-345, miR-425, miR-132, miR-1207-5p, miR-1301, miR-663, miR-339-5p, miR-149-star, miR-150, miR-18a, miR-103, miR-191, miR-296-3p, miR-31, miR-107*, miR-93*, miR-1275*, miR-181B*, miR-921*, miR-1225-5p, miR-1202, and miR-342-3p.

The kit may also primers for amplification of controls, such as miR-27b, miR-195, miR-199b-3p, and miR-199a-3p.

The kit may also include suitable buffers, reagents for isolating nucleic acid, and instructions for use Kits may also include a microarray for measuring miRNA level The primers may be labeled with a detectable marker such as radioactive isotopes, or fluorescence markers. Instructions for using the kit or reagents contained therein are also included in the kit.

EXAMPLES

The present methods and kits, thus generally described, will be understood more readily by reference to the following examples, which are provided by way of illustration and are not intended to be limiting of the present methods and kits. The following is a description of the materials and experimental procedures used in the example.

Example 1

137 samples were examined: (1) 19 normal skin; (2) 38 nevi, of which 20 were intradermal, where the nevus cells are located in the dermis only, and 18 were compound nevus, which is a mixture of junctional and intradermal proliferation and are slightly raised and brown to black; (3) 58 primary melanoma; (4) 22 metastatic melanoma.

Total RNA, including low molecular weight RNA, was isolated from ten 10 μm-FFPE sections with RecoverAll RNA extraction kit (Applied Biosystems), according to the manufacturer's protocol.

The Affymetrix GeneChip® miRNA array was used, according to the manufacturer's protocol, to evaluate miRNA expression in FFPE samples. The miRNA array covers 71 organisms, including human, mouse, rat, and monkey, and contains 1801 sets of human miRNA, snoR-NAs and scaRNAs. Samples were labeled using the Genisphere FlashTag™ Biotin Labeling Assay, which utilizes the 3DNA™ technology. The 3DNA™ dendrimer was ligated to samples to allow multiple biotin molecules (~15) to bind to each poly-A tailed RNA molecule. Following FlashTag™ ligation, samples were hybridized on the Affymetrix GeneChip® miRNA array overnight. The hybridized chips were washed and processed to scan in an Affimatrix GeneChip Scanner 3000 7G.

Statistical Analyses

The raw microarray data was analyzed using the miRNA QC tool which performed an RNA normalization and extracted signals for data analysis. Log 2 values were used for miRNA expression in each group. The log 2 fold change (log 2 FC) was calculated by subtracting the mean of log 2 of group1 from the mean log 2 of group 2. Student's t test was used to compare the miRNA expression level of each miRNA between normal skin, nevi, melanoma, and metastatic melanoma. $P<0.05$ was used as statistical significance. The area under ROC (AUC) was calculated to reflect the separation between each group. The default AUC value is 0.5 meaning no separation, and the maximum possible value is 1.0, meaning complete separation between each group.

A screen on probe signal detection in samples was performed having of 137 samples at least >30 samples with signal detectable. There are 729 of 1801 human probes satisfying such condition. These 729 candidate markers were analyzed using multiple algorithm programs.

Two or three markers completely separate these melanoma from nevi, as confirmed by multiple algorithms. The best 15 miRNA markers from randomForest share 14 markers overlap with the best 15 markers from boosting. In addition, these 14 best overlap markers include 6 of 7 best markers from previous analyses of 40 melanoma vs 20 nevi. These results therefore show consistency across different assays at different times.

Example 2

Additional experiments were performed to identify miRNA that can distinguish between different skin conditions.

For melanoma vs nevus, specimens (n=380) included a training set of 20 paraffin-embedded blocks of normal skin, 60 paraffin-embedded blocks of skin biopsies with benign nevus, 60 paraffin-embedded blocks of skin biopsies with malignant melanoma. Next, a validation set of 100 paraffin-embedded blocks of skin biopsies with benign nevus, 100 paraffin-embedded blocks of skin biopsies with malignant melanoma and 50 paraffin-embedded blocks of dysplastic nevus.

To distinguish between primary melanoma and metastatic melanoma, 180 study specimens included a training set of 60 paraffin-embedded blocks of skin biopsies with malignant melanoma and 30 paraffin-embedded blocks of metastatic melanoma. The validation set comprised 60 paraffin-embedded blocks of skin biopsies with malignant melanoma and 30 paraffin-embedded blocks of metastatic melanoma.

The subject population targeted all ethnicities and was approximately 50% male and 50% female. Specimens of adults 18 year and younger, and all subjects 89 years or older (">90") were discarded.

Tissues (normal benign, nevi and indeterminate nevus, malignant melanoma and metastatic melanoma) were collected at DermaPath. 240 nevi and 40 melanoma FFPEs were purchased from BioTheme.

Total RNA, including low molecular weight RNA, was isolated from ten 10 μm-FFPE sections with RecoverAll RNA extraction kit from Applied Biosystems according to the manufacturer's protocol.

The Affymetrix GeneChip® miRNA array was used to evaluate miRNA expression in FFPE samples. The miRNA array covers 71 organisms, including human, mouse, rat, and monkey, and contains 1801 sets of human miRNA, snoRNAs and scaRNAs.

The experiment procedure was according to the Affymetrix miRNA expression analysis manual. Samples were labeled with the Genisphere FlashTag™ Biotin Labeling Assay, which utilizes the 3DNA™ technology. The 3DNA™ dendrimer was ligated to samples to allow multiple biotin molecules (~15) to bind to each poly-A tailed RNA molecule. Following FlashTag™ ligation, samples were hybridized on the Affymetrix GeneChip® miRNA array overnight. The hybridized chips were washed and processed to scan in an Affimatrix GeneChip Scanner 3000 7G.

Statistical Analyses

Log 2 values were used for miRNA expression in each group. The log 2 fold change (log 2 FC) was calculated by subtracting the mean of log 2 of group 1 from the mean log 2 of group 2. Student's t test was used to compare the miRNA expression level of each miRNA between normal skin, nevi, melanoma, and metastatic melanoma. $P<0.05$ was used as statistical significance. The area under ROC (AUC) was calculated to reflect the separation between each group. The default AUC value is 0.5 meaning no separation, and the maximum possible value is 1.0, meaning complete separation between each group.

Semi-Quantitative Reverse-Transcriptase PCR Analysis of miRNA

Two-step TaqMan reverse-transcriptase PCR analysis was performed for analysis of miRNAs. Reverse transcription was performed in a 15-µl reaction volume using specific primers for each miRNA contained in the TaqMan MicroRNA Reverse Transcription kit (Applied Biosystems, Foster City, Calif.) by sequentially incubating at 16° C. for 30 min, 42° C. for 30 min, and 85° C. for 5 min. Real-time PCR was done using the standard TaqMan MicroRNA assay protocol on an Applied Biosysytems 7900 system (Applied Biosystems). Each PCR mixture (20 µl) included the reverse transcription products, TaqMan 2X Universal PCR Master Mix without UNG Amperase, miRNA-specific TaqMan probes, and primers supplied by Applied Biosystems. The reactions were incubated in a 96-well plate with an initial denaturation at 95° C. for 10 min, followed by 40 cycles of 95° C. for 15 s and 60° C. for 1 min. The level of miRNA expression was measured using the threshold cycle (Ct), the fractional cycle number at which the fluorescence of each sample passes a fixed threshold. miRNA expression levels were normalized using an endogenous small RNA control U44 (Applied Biosystems). The expression of miRNA relative to small RNA U44 is reported as ΔCt, which was calculated by subtracting the Ct of U44 RNA from the Ct of target miRNA.

4. Results

MiRNA expression was analyzed between each group. Table 1 shows 523 miRNAs which have significant expression level, either over or less expression, between melanoma and nevi groups ($p<0.05$). Table 2 showed 50 miRNAs with the most significant expression between the two groups. Table 3 showed 378 miRNAs which have significant expression differences between melanoma and normal skin groups ($p<0.05$). Table 4 showed 50 miRNAs with the most significant expression differences between the two groups. Table 5 showed 174 miRNAs which have significant expression differences between melanoma and metastatic melanoma groups ($p<0.05$). Table 6 showed 50 miRNAs with the most significant expression differences between the two groups. Table 7 showed 442 miRNAs which have significant expression differences between nevi and normal skin groups ($p<0.05$). Table 8 showed 50 miRNAs with the most significant expression differences between the two groups.

TABLE 1 miRNAs significantly expressed between melanoma and nevi

| Probe Name | Log2-FC | P value | AUC | ProbeType | #Sample Detected |
|---|---|---|---|---|---|
| miR-132 | 2.98 | 1.2728E−32 | 0.994 | miRNA | 96 |
| miR-150 | 3.27 | 5.83192E−30 | 1.000 | miRNA | 117 |
| miR-339-5p | 2.73 | 1.69388E−27 | 0.988 | miRNA | 75 |
| miR-15b | 3.02 | 6.41784E−27 | 0.978 | miRNA | 125 |
| miR-342-3p | 2.23 | 7.03798E−26 | 0.993 | miRNA | 136 |
| miR-572 | −2.78 | 1.00008E−25 | 0.970 | miRNA | 116 |
| miR-155 | 4.14 | 1.28454E−25 | 0.981 | miRNA | 123 |
| miR-425 | 2.74 | 8.13135E−25 | 0.975 | miRNA | 114 |
| miR-1202 | −2.63 | 2.97795E−23 | 0.986 | miRNA | 57 |
| miR-1268 | −2.68 | 6.05905E−23 | 0.997 | miRNA | 133 |
| HBII-382_s | −1.71 | 6.58931E−22 | 0.971 | scaRna | 126 |
| miR-1225-5p | −2.36 | 1.05361E−21 | 0.953 | miRNA | 90 |
| miR-30c | 2.39 | 2.58594E−21 | 0.980 | miRNA | 125 |
| miR-106b-star | 2.24 | 3.48507E−21 | 0.961 | miRNA | 72 |
| miR-125a-5p | 2.39 | 6.90609E−21 | 0.967 | miRNA | 128 |
| mgU6-53B | −1.51 | 1.74782E−20 | 0.973 | CDBox | 99 |
| miR-25 | 2.57 | 1.52769E−19 | 0.956 | miRNA | 118 |
| miR-149-star | −2.03 | 1.64858E−19 | 1.000 | miRNA | 135 |
| miR-939 | −2.21 | 1.9129E−19 | 0.973 | miRNA | 57 |
| miR-92b-star | −2.30 | 2.05085E−19 | 0.969 | miRNA | 111 |
| miR-500-star | 2.38 | 3.11256E−19 | 0.956 | miRNA | 97 |
| miR-22 | 2.69 | 3.8844E−19 | 0.965 | miRNA | 120 |
| HBII-142_x | −1.22 | 4.93318E−19 | 0.981 | CDBox | 135 |
| miR-181b | 2.41 | 1.00639E−18 | 0.960 | miRNA | 130 |
| HBII-142 | −1.33 | 1.18794E−18 | 0.988 | CDBox | 135 |
| U38B | −1.95 | 1.35964E−18 | 0.975 | CDBox | 134 |
| miR-663 | −2.10 | 2.04672E−18 | 0.984 | miRNA | 134 |
| miR-1224-5p | −2.54 | 2.91169E−18 | 0.946 | miRNA | 78 |
| miR-23a | 1.18 | 2.99523E−18 | 0.967 | miRNA | 137 |
| HBII-85-6_x | −1.73 | 4.78418E−18 | 0.939 | CDBox | 137 |
| miR-1207-5p | −2.14 | 4.98991E−18 | 0.995 | miRNA | 133 |

TABLE 1-continued miRNAs significantly expressed between melanoma and nevi

| Probe Name | Log2-FC | P value | AUC | ProbeType | #Sample Detected |
|---|---|---|---|---|---|
| miR-1301 | 2.36 | 5.22389E−18 | 0.931 | miRNA | 54 |
| miR-1228-star | −2.41 | 5.51513E−18 | 0.997 | miRNA | 134 |
| miR-345 | 2.45 | 6.43552E−18 | 0.942 | miRNA | 75 |
| miR-30a-star | 2.32 | 6.92165E−18 | 0.932 | miRNA | 64 |
| ENSG00000199411_s | −1.97 | 7.23325E−18 | 0.991 | snoRNA | 135 |
| ENSG00000202327 | −1.40 | 8.75839E−18 | 0.938 | snoRNA | 54 |
| miR-92a | 1.67 | 9.49427E−18 | 0.979 | miRNA | 136 |
| miR-127-3p | 2.43 | 9.84615E−18 | 0.936 | miRNA | 89 |
| HBII-85-26 | −2.07 | 1.50619E−17 | 0.951 | CDBox | 136 |
| miR-1308 | −2.14 | 1.99888E−17 | 0.999 | miRNA | 135 |
| miR-31 | 3.29 | 2.46697E−17 | 0.913 | miRNA | 103 |
| miR-921 | −1.46 | 2.61089E−17 | 0.928 | miRNA | 49 |
| miR-146b-5p | 2.37 | 6.10422E−17 | 0.918 | miRNA | 83 |
| miR-768-3p | −1.05 | 6.66153E−17 | 0.949 | miRNA | 137 |
| miR-708 | 2.29 | 6.86187E−17 | 0.929 | miRNA | 102 |
| miR-139-5p | 2.23 | 2.78962E−16 | 0.922 | miRNA | 80 |
| ACA24_x | 1.33 | 3.37973E−16 | 0.925 | HAcaBox | 98 |
| miR-501-3p | 1.83 | 4.76751E−16 | 0.923 | miRNA | 80 |
| miR-502-3p | 2.16 | 5.19509E−16 | 0.925 | miRNA | 110 |
| miR-923 | −1.86 | 5.55191E−16 | 0.996 | miRNA | 135 |
| U94 | −1.17 | 6.40118E−16 | 0.926 | CDBox | 109 |
| miR-574-3p | 2.32 | 8.68105E−16 | 0.946 | miRNA | 122 |
| miR-135a-star | −1.90 | 1.03062E−15 | 0.914 | miRNA | 44 |
| ENSG00000207098_x | −1.03 | 1.25346E−15 | 0.924 | snoRNA | 86 |
| U38B_x | −1.55 | 2.54255E−15 | 0.958 | CDBox | 133 |
| miR-423-3p | 1.83 | 2.74508E−15 | 0.932 | miRNA | 107 |
| miR-198 | −1.79 | 3.57486E−15 | 0.909 | miRNA | 31 |
| ACA16 | 1.43 | 4.07871E−15 | 0.919 | HAcaBox | 47 |
| ACA25 | 1.06 | 4.62028E−15 | 0.910 | HAcaBox | 73 |
| miR-769-5p | 1.63 | 4.79679E−15 | 0.920 | miRNA | 56 |
| ENSG00000212523_x | −1.38 | 6.22717E−15 | 0.927 | snoRNA | 135 |
| mgU6-53B_x | −0.99 | 6.32629E−15 | 0.919 | CDBox | 121 |
| Z17B | 0.97 | 1.1349E−14 | 0.903 | CDBox | 117 |
| U81_x | 1.22 | 1.25935E−14 | 0.913 | CDBox | 120 |
| miR-532-5p | 2.10 | 1.27686E−14 | 0.933 | miRNA | 113 |
| ENSG00000200879 | 1.27 | 1.49096E−14 | 0.917 | snoRNA | 120 |
| HBII-419 | −1.07 | 2.02184E−14 | 0.938 | CDBox | 133 |
| U58B_x | 0.96 | 9.25535E−14 | 0.898 | CDBox | 132 |
| ENSG00000201619 | −1.66 | 1.14582E−13 | 0.911 | snoRNA | 62 |
| miR-28-3p | 2.15 | 1.17402E−13 | 0.900 | miRNA | 94 |
| miR-1300 | −1.86 | 1.21666E−13 | 0.892 | miRNA | 32 |
| miR-191 | 1.18 | 1.2767E−13 | 0.983 | miRNA | 135 |
| miR-181a-2-star | 1.93 | 2.91245E−13 | 0.898 | miRNA | 99 |
| U38A | −1.52 | 3.04032E−13 | 0.971 | CDBox | 134 |
| U59A | −1.01 | 3.86379E−13 | 0.948 | CDBox | 135 |
| ENSG00000212397 | −1.21 | 4.58111E−13 | 0.902 | snoRNA | 134 |
| HBII-85-26_x | −1.13 | 4.73092E−13 | 0.897 | CDBox | 135 |
| miR-638 | −1.62 | 5.93273E−13 | 0.967 | miRNA | 135 |
| miR-421 | 1.84 | 6.09941E−13 | 0.881 | miRNA | 68 |
| miR-21 | 2.62 | 6.26336E−13 | 0.888 | miRNA | 79 |
| miR-24-2-star | 1.81 | 8.95923E−13 | 0.879 | miRNA | 63 |
| U36C | −0.92 | 1.1248E−12 | 0.931 | CDBox | 135 |
| miR-92b | 1.43 | 1.15239E−12 | 0.901 | miRNA | 91 |
| miR-199a-5p | 1.69 | 1.22362E−12 | 0.901 | miRNA | 129 |
| ACA24_s | 1.36 | 1.86137E−12 | 0.880 | HAcaBox | 128 |
| ACA9 | 1.36 | 1.92813E−12 | 0.888 | HAcaBox | 82 |
| ENSG00000199411_x | −0.87 | 2.22903E−12 | 0.868 | snoRNA | 132 |
| ENSG00000199435 | −0.94 | 2.45067E−12 | 0.903 | snoRNA | 63 |
| miR-182 | 1.80 | 3.73608E−12 | 0.905 | miRNA | 113 |
| miR-1275 | −1.56 | 3.97629E−12 | 0.888 | miRNA | 127 |
| miR-150-star | −1.70 | 4.59839E−12 | 0.897 | miRNA | 48 |
| ACA48_x | 1.08 | 5.05927E−12 | 0.881 | HAcaBox | 130 |
| HBII-85-8_x | −1.09 | 5.47576E−12 | 0.877 | CDBox | 135 |
| miR-99b | 1.33 | 5.48764E−12 | 0.907 | miRNA | 129 |
| U74_x | −1.00 | 6.23625E−12 | 0.941 | CDBox | 135 |
| miR-1271 | 1.71 | 6.2815E−12 | 0.885 | miRNA | 70 |
| ENSG00000206637_x | −0.86 | 6.43179E−12 | 0.878 | snoRNA | 59 |
| miR-20b | 2.16 | 1.13294E−11 | 0.892 | miRNA | 99 |
| ENSG00000200652 | −0.93 | 1.18064E−11 | 0.876 | snoRNA | 40 |
| U13 | −0.94 | 1.19458E−11 | 0.899 | CDBox | 135 |
| ENSG00000201660 | −1.13 | 1.27245E−11 | 0.903 | snoRNA | 132 |
| HBII-85-23_x | 1.18 | 1.36679E−11 | 0.883 | CDBox | 58 |
| miR-149 | 1.85 | 1.38908E−11 | 0.896 | miRNA | 100 |
| ACA9_x | 1.14 | 2.05352E−11 | 0.877 | HAcaBox | 77 |
| miR-1234 | −1.10 | 2.16855E−11 | 0.856 | miRNA | 68 |

TABLE 1-continued miRNAs significantly expressed between melanoma and nevi

| Probe Name | Log2-FC | P value | AUC | ProbeType | #Sample Detected |
|---|---|---|---|---|---|
| miR-1180 | 1.50 | 2.61371E−11 | 0.878 | miRNA | 37 |
| miR-30a | 1.80 | 3.39494E−11 | 0.861 | miRNA | 113 |
| U44_x | 1.13 | 3.71768E−11 | 0.953 | CDBox | 135 |
| miR-181c | 1.54 | 4.41605E−11 | 0.861 | miRNA | 59 |
| ENSG00000202498_x | −1.07 | 4.69703E−11 | 0.855 | snoRNA | 137 |
| miR-940 | −1.22 | 5.55177E−11 | 0.861 | miRNA | 53 |
| miR-500 | 1.76 | 6.23662E−11 | 0.854 | miRNA | 86 |
| ENSG00000212627 | −0.78 | 6.92771E−11 | 0.871 | snoRNA | 69 |
| ENSG00000207027 | −0.84 | 8.23933E−11 | 0.879 | snoRNA | 36 |
| miR-27a-star | 1.63 | 8.66657E−11 | 0.856 | miRNA | 40 |
| miR-128 | 1.66 | 9.46068E−11 | 0.858 | miRNA | 44 |
| snR38C | −1.01 | 9.50785E−11 | 0.926 | CDBox | 134 |
| ENSG00000212266 | −0.93 | 9.6633E−11 | 0.848 | snoRNA | 93 |
| miR-185 | 1.76 | 1.06661E−10 | 0.922 | miRNA | 132 |
| ACA64 | −0.97 | 1.08821E−10 | 0.858 | HAcaBox | 33 |
| miR-151-3p | 1.71 | 1.37187E−10 | 0.884 | miRNA | 117 |
| miR-130b | 2.12 | 1.55732E−10 | 0.870 | miRNA | 90 |
| miR-27b-star | 1.70 | 1.72122E−10 | 0.849 | miRNA | 51 |
| miR-665 | −1.43 | 1.78835E−10 | 0.853 | miRNA | 47 |
| miR-18a | 2.01 | 1.91068E−10 | 0.854 | miRNA | 77 |
| ACA36_x | −1.03 | 2.0756E−10 | 0.875 | HAcaBox | 88 |
| ENS00000212432_s | −0.94 | 2.08962E−10 | 0.882 | snoRNA | 75 |
| ENSG00000202093_x | 1.01 | 4.04338E−10 | 0.873 | snoRNA | 125 |
| miR-487b | 1.41 | 4.22069E−10 | 0.848 | miRNA | 58 |
| U65 | −0.98 | 4.31315E−10 | 0.847 | HAcaBox | 128 |
| miR-532-3p | 1.19 | 4.73885E−10 | 0.881 | miRNA | 95 |
| U101 | −0.79 | 5.89958E−10 | 0.845 | CDBox | 134 |
| miR-138 | 2.09 | 6.68933E−10 | 0.839 | miRNA | 82 |
| HBII-99 | 1.01 | 7.89663E−10 | 0.847 | CDBox | 122 |
| miR-222 | 1.12 | 9.21171E−10 | 0.913 | miRNA | 135 |
| miR-652 | 1.46 | 9.82734E−10 | 0.862 | miRNA | 119 |
| miR-10a | 1.82 | 9.97674E−10 | 0.843 | miRNA | 69 |
| miR-625 | 1.46 | 1.06062E−09 | 0.833 | miRNA | 59 |
| ENSG00000212182 | −0.89 | 1.13997E−09 | 0.828 | snoRNA | 59 |
| miR-331-3p | 1.47 | 1.22124E−09 | 0.834 | miRNA | 64 |
| miR-1281 | −1.46 | 1.31027E−09 | 0.843 | miRNA | 137 |
| miR-28-5p | 1.53 | 1.35526E−09 | 0.863 | miRNA | 105 |
| ACA23 | 0.76 | 2.45172E−09 | 0.837 | HAcaBox | 113 |
| U27 | 1.04 | 2.55698E−09 | 0.874 | CDBox | 134 |
| miR-339-3p | 1.12 | 2.9234E−09 | 0.836 | miRNA | 60 |
| U68_x | 1.00 | 3.99716E−09 | 0.861 | HAcaBox | 133 |
| miR-92a-2-star | −1.06 | 4.67209E−09 | 0.830 | miRNA | 46 |
| miR-107 | 1.08 | 5.05068E−09 | 0.946 | miRNA | 135 |
| U104 | −0.79 | 5.07142E−09 | 0.918 | CDBox | 135 |
| miR-671-5p | −1.16 | 6.05404E−09 | 0.877 | miRNA | 69 |
| miR-193b | 1.22 | 6.27171E−09 | 0.852 | miRNA | 130 |
| miR-1272 | −1.13 | 6.29028E−09 | 0.826 | miRNA | 67 |
| miR-221 | 1.23 | 6.5716E−09 | 0.911 | miRNA | 135 |
| 14qII-14 | 1.27 | 6.8516E−09 | 0.828 | CDBox | 56 |
| miR-1288 | −0.92 | 6.95468E−09 | 0.804 | miRNA | 43 |
| ENSG00000212458 | −0.80 | 7.62772E−09 | 0.853 | snoRNA | 95 |
| miR-584 | 1.61 | 7.63622E−09 | 0.815 | miRNA | 57 |
| U106 | 0.64 | 8.00299E−09 | 0.821 | CDBox | 112 |
| miR-152 | 1.58 | 8.26552E−09 | 0.885 | miRNA | 122 |
| ENSG00000212551 | −0.72 | 9.08023E−09 | 0.841 | snoRNA | 73 |
| U96a_x | −0.89 | 1.00143E−08 | 0.863 | CDBox | 134 |
| ENSG00000212139_x | −0.74 | 1.22887E−08 | 0.811 | snoRNA | 124 |
| miR-409-3p | 1.14 | 1.25923E−08 | 0.832 | miRNA | 92 |
| miR-214-star | 1.59 | 1.34912E−08 | 0.830 | miRNA | 47 |
| ACA20 | 0.91 | 1.36416E−08 | 0.873 | HAcaBox | 131 |
| HBII-82 | −0.73 | 1.52532E−08 | 0.823 | CDBox | 90 |
| U49A | −0.86 | 1.55769E−08 | 0.856 | CDBox | 135 |
| miR-362-5p | 1.63 | 1.67441E−08 | 0.824 | miRNA | 94 |
| ACA40_x | 1.17 | 1.68127E−08 | 0.872 | HAcaBox | 134 |
| U63 | −0.98 | 1.83203E−08 | 0.916 | CDBox | 135 |
| HBII-436 | 0.76 | 1.85498E−08 | 0.810 | CDBox | 102 |
| miR-15a | 1.74 | 1.8639E−08 | 0.826 | miRNA | 80 |
| U103_s | 0.83 | 2.02002E−08 | 0.809 | CDBox | 111 |
| miR-1185 | −0.96 | 2.35573E−08 | 0.822 | miRNA | 42 |
| ACA15_s | 0.74 | 2.84086E−08 | 0.812 | HAcaBox | 116 |
| miR-30b | 1.37 | 3.22874E−08 | 0.843 | miRNA | 128 |
| spike_in-control-21 | −0.70 | 3.25874E−08 | 0.832 | Oligonucleotide spike-in controls | 42 |
| U15B | 0.71 | 3.51612E−08 | 0.825 | CDBox | 129 |

TABLE 1-continued miRNAs significantly expressed between melanoma and nevi

| Probe Name | Log2-FC | P value | AUC | ProbeType | #Sample Detected |
|---|---|---|---|---|---|
| miR-143 | 1.99 | 3.72999E−08 | 0.820 | miRNA | 126 |
| U67_x | 0.79 | 4.12783E−08 | 0.813 | HAcaBox | 50 |
| miR-10b | 1.41 | 4.29563E−08 | 0.821 | miRNA | 106 |
| U99 | −0.65 | 4.50576E−08 | 0.817 | HAcaBox | 137 |
| miR-194 | 1.27 | 5.18787E−08 | 0.813 | miRNA | 54 |
| miR-324-5p | 1.14 | 5.23291E−08 | 0.804 | miRNA | 102 |
| miR-125b-2-star | 1.19 | 5.54514E−08 | 0.819 | miRNA | 58 |
| HBII-52-37_x | −0.76 | 8.93997E−08 | 0.805 | CDBox | 37 |
| ACA48 | 0.72 | 9.13165E−08 | 0.825 | HAcaBox | 121 |
| miR-103 | 0.97 | 9.25296E−08 | 0.931 | miRNA | 135 |
| miR-342-5p | 1.32 | 9.27998E−08 | 0.827 | miRNA | 98 |
| miR-93 | 1.08 | 9.93604E−08 | 0.896 | miRNA | 134 |
| miR-296-3p | −1.00 | 1.10115E−07 | 0.818 | miRNA | 90 |
| miR-200b-star | 1.30 | 1.13507E−07 | 0.791 | miRNA | 74 |
| U44 | 0.87 | 1.17791E−07 | 0.897 | CDBox | 134 |
| ENSG00000207016_x | −0.63 | 1.23122E−07 | 0.803 | snoRNA | 48 |
| spike_in-control-31 | −0.14 | 1.24357E−07 | 0.798 | Oligonucleotide spike-in controls | 137 |
| U68 | 0.83 | 1.72086E−07 | 0.856 | HAcaBox | 130 |
| U24 | −0.55 | 2.39582E−07 | 0.822 | CDBox | 133 |
| U83 | 0.62 | 2.42808E−07 | 0.846 | CDBox | 135 |
| ENSG00000212273_x | −0.80 | 2.45728E−07 | 0.811 | snoRNA | 126 |
| 14qII-14_x | 1.03 | 2.59298E−07 | 0.797 | CDBox | 56 |
| miR-660 | 1.26 | 2.65402E−07 | 0.788 | miRNA | 71 |
| 14qII-7 | −0.70 | 2.89281E−07 | 0.762 | CDBox | 77 |
| U78_s | 1.01 | 3.07849E−07 | 0.836 | CDBox | 135 |
| miR-744 | −1.03 | 3.11141E−07 | 0.818 | miRNA | 133 |
| U22 | −0.54 | 3.14269E−07 | 0.793 | CDBox | 135 |
| ACA11 | 0.70 | 3.50307E−07 | 0.793 | HAcaBox | 48 |
| ENSG00000212553_x | −0.69 | 3.51184E−07 | 0.794 | snoRNA | 60 |
| U67 | 0.76 | 3.78503E−07 | 0.796 | HAcaBox | 44 |
| miR-382 | 1.35 | 3.83783E−07 | 0.787 | miRNA | 47 |
| miR-212 | 1.58 | 3.89653E−07 | 0.854 | miRNA | 62 |
| miR-93-star | 1.26 | 4.02443E−07 | 0.808 | miRNA | 48 |
| U18C_x | 0.74 | 4.1571E−07 | 0.794 | CDBox | 74 |
| miR-1274a | 1.22 | 4.1577E−07 | 0.788 | miRNA | 48 |
| ACA25_x | 0.77 | 4.42948E−07 | 0.799 | HAcaBox | 114 |
| U15A | −0.74 | 4.57833E−07 | 0.821 | CDBox | 128 |
| 14qI-1 | −0.77 | 5.08646E−07 | 0.784 | CDBox | 70 |
| ENSG00000201816 | −0.60 | 5.51521E−07 | 0.789 | snoRNA | 49 |
| miR-145 | 1.56 | 6.30644E−07 | 0.775 | miRNA | 135 |
| HBII-420 | −0.75 | 7.96309E−07 | 0.828 | CDBox | 131 |
| ACA2b | −0.66 | 8.56351E−07 | 0.787 | HAcaBox | 47 |
| miR-1273 | −0.94 | 1.01224E−06 | 0.768 | miRNA | 47 |
| miR-641 | −0.85 | 1.0165E−06 | 0.765 | miRNA | 39 |
| ENSG00000202216 | −0.60 | 1.02726E−06 | 0.778 | snoRNA | 53 |
| U97 | −0.72 | 1.06795E−06 | 0.794 | CDBox | 133 |
| EN8G00000200706_x | −0.66 | 1.06937E−06 | 0.778 | snoRNA | 43 |
| miR-363 | 1.33 | 1.20135E−06 | 0.806 | miRNA | 44 |
| ENSG00000201348 | −0.48 | 1.23741E−06 | 0.779 | snoRNA | 94 |
| U83A | 0.75 | 1.32496E−06 | 0.818 | CDBox | 127 |
| miR-197 | 1.27 | 1.3431E−06 | 0.807 | miRNA | 103 |
| miR-106b | 1.23 | 1.49024E−06 | 0.805 | miRNA | 127 |
| HBII-180A_x | 0.60 | 1.62491E−06 | 0.784 | CDBox | 123 |
| snR38B | −0.76 | 1.68966E−06 | 0.803 | CDBox | 126 |
| snR38A | −0.87 | 1.99208E−06 | 0.838 | CDBox | 130 |
| miR-134 | 1.15 | 2.09717E−06 | 0.774 | miRNA | 61 |
| miR-29b-1-star | 1.41 | 2.20964E−06 | 0.764 | miRNA | 46 |
| mgh18S-121 | −0.66 | 2.37986E−06 | 0.833 | CDBox | 134 |
| mgU6-77 | 0.59 | 2.38866E−06 | 0.742 | CDBox | 129 |
| HBII-52-25_x | −0.60 | 2.44738E−06 | 0.767 | CDBox | 57 |
| U48 | 0.83 | 2.51688E−06 | 0.777 | CDBox | 129 |
| 14qII-19 | −0.73 | 2.52816E−06 | 0.770 | CDBox | 43 |
| miR-552 | −0.66 | 2.70576E−06 | 0.760 | miRNA | 34 |
| miR-424-star | 1.31 | 2.79344E−06 | 0.762 | miRNA | 41 |
| HBII-316 | −0.60 | 3.06016E−06 | 0.795 | CDBox | 130 |
| U35B | −0.64 | 3.21695E−06 | 0.811 | CDBox | 128 |
| miR-30d | 1.02 | 3.25088E−06 | 0.817 | miRNA | 131 |
| miR-1248 | −0.72 | 3.27937E−06 | 0.746 | miRNA | 39 |
| ENSG00000212579_x | −0.65 | 3.55239E−06 | 0.758 | snoRNA | 100 |
| hsa-let-7b | 0.90 | 3.76667E−06 | 0.919 | miRNA | 136 |
| miR-29b-2-star | −0.78 | 3.86015E−06 | 0.760 | miRNA | 126 |
| miR-148a | 1.04 | 4.16979E−06 | 0.773 | miRNA | 41 |
| miR-629 | 1.16 | 4.35623E−06 | 0.776 | miRNA | 64 |

TABLE 1-continued miRNAs significantly expressed between melanoma and nevi

| Probe Name | Log2-FC | P value | AUC | ProbeType | #Sample Detected |
|---|---|---|---|---|---|
| HBII-295 | −0.58 | 4.36224E−06 | 0.767 | CDBox | 128 |
| miR-877 | −1.00 | 4.43293E−06 | 0.794 | miRNA | 126 |
| ACA62 | −0.61 | 4.43469E−06 | 0.774 | HAcaBox | 88 |
| ENSG00000207100_x | −0.50 | 4.49659E−06 | 0.765 | snoRNA | 72 |
| HBII-180C | 0.62 | 4.78509E−06 | 0.780 | CDBox | 115 |
| HBII-115 | −0.57 | 5.03448E−06 | 0.768 | CDBox | 117 |
| miR-192 | 1.14 | 5.73989E−06 | 0.763 | miRNA | 32 |
| miR-505-star | 1.23 | 5.74055E−06 | 0.762 | miRNA | 58 |
| spike_in-control-7 | −0.80 | 5.89851E−06 | 0.790 | Oligonucleotide spike-in controls | 54 |
| miR-422a | 1.17 | 5.96437E−06 | 0.782 | miRNA | 84 |
| U83B | −0.56 | 6.55847E−06 | 0.842 | CDBox | 135 |
| ENSG00000212134_x | −0.65 | 6.92676E−06 | 0.752 | snoRNA | 88 |
| U50B_x | −0.67 | 7.13703E−06 | 0.783 | CDBox | 135 |
| miR-193a-3p | 0.91 | 8.82408E−06 | 0.747 | miRNA | 42 |
| ENSG00000201848 | −0.62 | 9.39369E−06 | 0.759 | snoRNA | 34 |
| miR-148b | 0.93 | 9.94696E−06 | 0.757 | miRNA | 32 |
| miR-483-5p | −1.10 | 1.1191E−05 | 0.756 | miRNA | 48 |
| ACA58_x | 0.62 | 1.17327E−05 | 0.766 | HAcaBox | 89 |
| miR-1260 | 0.94 | 1.21296E−05 | 0.776 | miRNA | 120 |
| U108_x | −0.50 | 1.23481E−05 | 0.763 | HAcaBox | 87 |
| ACA61 | −0.60 | 1.27104E−05 | 0.839 | HAcaBox | 135 |
| 14q-0 | −0.58 | 1.39356E−05 | 0.767 | CDBox | 49 |
| ACA16_x | 0.55 | 1.40972E−05 | 0.763 | HAcaBox | 98 |
| miR-30b-star | 1.22 | 1.61096E−05 | 0.755 | miRNA | 61 |
| ENSG00000201848_x | −0.58 | 2.11059E−05 | 0.740 | snoRNA | 40 |
| U3-2_s | −0.57 | 2.19611E−05 | 0.800 | CDBox | 135 |
| spike_in-control-2 | −0.31 | 2.25868E−05 | 0.747 | Oligonucleotide spike-in controls | 137 |
| miR-933 | −0.56 | 2.89505E−05 | 0.776 | miRNA | 100 |
| miR-181d | 1.03 | 2.90988E−05 | 0.750 | miRNA | 61 |
| HBII-239 | 0.45 | 2.92435E−05 | 0.744 | CDBox | 135 |
| miR-497 | 1.17 | 2.92719E−05 | 0.730 | miRNA | 104 |
| HBII-251 | −0.48 | 3.04823E−05 | 0.797 | CDBox | 135 |
| U51 | −0.73 | 3.10371E−05 | 0.809 | CDBox | 134 |
| miR-211 | 1.45 | 3.41149E−05 | 0.759 | miRNA | 84 |
| miR-29a | 1.10 | 3.68833E−05 | 0.777 | miRNA | 128 |
| ENSG00000212538 | −0.54 | 3.71864E−05 | 0.746 | snoRNA | 35 |
| miR-886-3p | 1.11 | 4.28603E−05 | 0.711 | miRNA | 110 |
| miR-361-5p | 0.58 | 4.51572E−05 | 0.859 | miRNA | 135 |
| U51_x | −0.48 | 4.6523E−05 | 0.773 | CDBox | 130 |
| U46 | 0.59 | 4.67792E−05 | 0.744 | CDBox | 133 |
| HBII-85-11 | 0.73 | 4.72933E−05 | 0.743 | CDBox | 31 |
| ENSG00000207410_x | −0.51 | 4.76931E−05 | 0.731 | snoRNA | 55 |
| ENSG00000200492 | −0.51 | 5.13688E−05 | 0.756 | snoRNA | 60 |
| miR-503 | 1.05 | 5.22927E−05 | 0.730 | miRNA | 41 |
| HBII-85-21_x | 0.68 | 5.24419E−05 | 0.749 | CDBox | 39 |
| miR-506 | 1.27 | 5.49222E−05 | 0.750 | miRNA | 76 |
| ENSG00000212206_x | −0.55 | 5.68573E−05 | 0.730 | snoRNA | 74 |
| U64 | 0.49 | 5.7913E−05 | 0.755 | HAcaBox | 101 |
| miR-629-star | 1.07 | 5.89793E−05 | 0.745 | miRNA | 46 |
| ENSG00000212284 | −0.62 | 6.56826E−05 | 0.740 | snoRNA | 89 |
| ENSG00000212423_x | −0.60 | 6.59628E−05 | 0.728 | snoRNA | 115 |
| U14B_x | 0.58 | 6.71139E−05 | 0.714 | CDBox | 53 |
| miR-324-3p | 0.78 | 6.71385E−05 | 0.766 | miRNA | 100 |
| miR-1287 | 0.79 | 7.37546E−05 | 0.733 | miRNA | 40 |
| ENSG00000200897 | −0.49 | 7.55587E−05 | 0.730 | snoRNA | 38 |
| miR-498 | −0.68 | 8.15427E−05 | 0.730 | miRNA | 56 |
| U80 | 0.53 | 8.25012E−05 | 0.750 | CDBox | 132 |
| 14qI-8_x | −0.55 | 8.60271E−05 | 0.740 | CDBox | 74 |
| miR-181a | 0.82 | 8.99722E−05 | 0.766 | miRNA | 134 |
| HBII-166 | −0.46 | 9.07119E−05 | 0.782 | CDBox | 134 |
| miR-181a-star | 1.03 | 9.30754E−05 | 0.727 | miRNA | 35 |
| U17b | 0.85 | 9.69173E−05 | 0.854 | HAcaBox | 135 |
| U55 | 0.61 | 0.000102241 | 0.749 | CDBox | 135 |
| ENSG00000207407 | −0.43 | 0.000115453 | 0.706 | snoRNA | 56 |
| ENSG00000212206 | −0.50 | 0.000123184 | 0.701 | snoRNA | 46 |
| miR-489 | 0.86 | 0.000125451 | 0.724 | miRNA | 58 |
| hsa-let-7g | 1.09 | 0.000128044 | 0.820 | miRNA | 127 |
| ENSG00000199363 | 0.63 | 0.000135904 | 0.722 | snoRNA | 42 |
| miR-27a | 0.72 | 0.000140934 | 0.687 | miRNA | 136 |
| ACA32 | −0.40 | 0.000144838 | 0.746 | HAcaBox | 135 |
| ENSG00000207022 | −0.51 | 0.000149628 | 0.733 | snoRNA | 36 |

TABLE 1-continued miRNAs significantly expressed between melanoma and nevi

| Probe Name | Log2-FC | P value | AUC | ProbeType | #Sample Detected |
|---|---|---|---|---|---|
| miR-371-5p | −0.86 | 0.000152576 | 0.706 | miRNA | 64 |
| miR-559 | −0.73 | 0.000161415 | 0.728 | miRNA | 72 |
| miR-193a-5p | 0.92 | 0.000163281 | 0.777 | miRNA | 121 |
| U23 | 0.46 | 0.00016459 | 0.724 | HAcaBox | 127 |
| miR-196a-star | −0.69 | 0.000167433 | 0.695 | miRNA | 37 |
| U52 | 0.47 | 0.00016782 | 0.770 | CDBox | 135 |
| ACA38 | 0.50 | 0.000170509 | 0.713 | HAcaBox | 42 |
| miR-30e-star | 0.82 | 0.000173654 | 0.736 | miRNA | 35 |
| U49A_x | −0.61 | 0.000183863 | 0.785 | CDBox | 135 |
| U49B_x | −0.54 | 0.000189603 | 0.729 | CDBox | 122 |
| U71a | 0.50 | 0.000191925 | 0.721 | HAcaBox | 50 |
| HBII-95 | 0.42 | 0.000194646 | 0.724 | CDBox | 78 |
| ENSG00000212587 | −0.55 | 0.000201583 | 0.711 | snoRNA | 45 |
| ENSG00000212401 | −0.45 | 0.000208666 | 0.714 | snoRNA | 41 |
| HBII-296A | −0.45 | 0.000214033 | 0.713 | CDBox | 78 |
| ACA67_x | 0.49 | 0.000214513 | 0.730 | HAcaBox | 54 |
| miR-494 | 0.79 | 0.000221314 | 0.725 | miRNA | 135 |
| miR-17 | 0.77 | 0.00024803 | 0.782 | miRNA | 134 |
| HBII-85-4_x | −0.49 | 0.000264241 | 0.714 | CDBox | 125 |
| miR-16 | 0.67 | 0.000270072 | 0.819 | miRNA | 135 |
| miR-135b-star | −0.68 | 0.000271929 | 0.710 | miRNA | 38 |
| ACA37_x | 0.47 | 0.00028645 | 0.718 | HAcaBox | 84 |
| miR-126 | 0.82 | 0.000326027 | 0.780 | miRNA | 133 |
| miR-200b | 0.93 | 0.000339327 | 0.714 | miRNA | 109 |
| miR-320d | 0.89 | 0.000373646 | 0.811 | miRNA | 134 |
| U100 | 0.41 | 0.000374728 | 0.702 | scaRna | 80 |
| HBII-85-27_x | −0.40 | 0.000383642 | 0.706 | CDBox | 56 |
| HBII-85-15_x | 0.60 | 0.000397454 | 0.706 | CDBox | 49 |
| miR-885-3p | −1.11 | 0.000407264 | 0.692 | miRNA | 73 |
| miR-23b-star | 0.76 | 0.000423736 | 0.723 | miRNA | 52 |
| ENSG00000206909_x | −0.46 | 0.000424153 | 0.710 | snoRNA | 47 |
| U92 | −0.50 | 0.000428521 | 0.750 | scaRna | 129 |
| miR-628-3p | 0.86 | 0.000458761 | 0.702 | miRNA | 38 |
| miR-27b | 0.70 | 0.00047114 | 0.718 | miRNA | 133 |
| U88 | −0.43 | 0.000500023 | 0.708 | scaRna | 69 |
| miR-130a | 1.00 | 0.000518644 | 0.729 | miRNA | 122 |
| ACA4 | 0.42 | 0.00055437 | 0.673 | HAcaBox | 117 |
| miR-151-5p | 0.60 | 0.00055594 | 0.790 | miRNA | 135 |
| ENSG00000200394 | 0.46 | 0.000561813 | 0.692 | snoRNA | 119 |
| ACA5 | 0.48 | 0.000585113 | 0.708 | HAcaBox | 85 |
| miR-1285 | −0.74 | 0.000607741 | 0.698 | miRNA | 54 |
| miR-664-star | −0.82 | 0.000652475 | 0.686 | miRNA | 96 |
| U56 | −0.57 | 0.000672557 | 0.787 | CDBox | 135 |
| ENSG00000200307 | −0.44 | 0.000679263 | 0.686 | snoRNA | 86 |
| miR-18b | 0.81 | 0.000708619 | 0.688 | miRNA | 32 |
| U76 | 0.38 | 0.000723275 | 0.712 | CDBox | 135 |
| miR-378 | 0.75 | 0.000726542 | 0.769 | miRNA | 131 |
| ENSG00000200307_x | −0.43 | 0.000739867 | 0.716 | snoRNA | 50 |
| miR-513b | 1.02 | 0.000775353 | 0.701 | miRNA | 64 |
| U56_x | 0.54 | 0.000779671 | 0.716 | CDBox | 134 |
| miR-642 | −0.59 | 0.000808799 | 0.695 | miRNA | 69 |
| miR-106a | 0.66 | 0.000811882 | 0.788 | miRNA | 135 |
| miR-379 | 0.94 | 0.000829873 | 0.702 | miRNA | 57 |
| miR-570 | −0.61 | 0.000842848 | 0.697 | miRNA | 88 |
| ACA3-2 | 0.46 | 0.000855145 | 0.720 | HAcaBox | 135 |
| U55_x | 0.50 | 0.000899835 | 0.746 | CDBox | 135 |
| ACA7_s | −0.34 | 0.000995798 | 0.703 | HAcaBox | 133 |
| miR-1228 | −0.67 | 0.001047707 | 0.730 | miRNA | 114 |
| miR-199a-3p | 0.75 | 0.001282519 | 0.729 | miRNA | 134 |
| ENSG00000212508 | −0.59 | 0.001303596 | 0.687 | snoRNA | 122 |
| ENSG00000200961 | −0.41 | 0.001335597 | 0.699 | snoRNA | 41 |
| miR-23b | 0.45 | 0.00142683 | 0.817 | miRNA | 137 |
| ENSG00000207177 | −0.34 | 0.001464718 | 0.697 | snoRNA | 59 |
| ACA50 | 0.41 | 0.001642667 | 0.674 | HAcaBox | 88 |
| miR-550-star | 0.75 | 0.001687411 | 0.692 | miRNA | 58 |
| miR-617 | −0.56 | 0.001827038 | 0.676 | miRNA | 64 |
| U75 | −0.57 | 0.001850734 | 0.729 | CDBox | 134 |
| HBII-85-2_x | −0.41 | 0.001956673 | 0.706 | CDBox | 135 |
| miR-508-5p | 0.77 | 0.001978936 | 0.711 | miRNA | 92 |
| miR-200a | 0.66 | 0.002095909 | 0.676 | miRNA | 33 |
| miR-574-5p | 0.79 | 0.002104165 | 0.749 | miRNA | 103 |
| ACA49 | −0.37 | 0.00221029 | 0.692 | HAcaBox | 127 |
| miR-1826 | 0.46 | 0.002224183 | 0.799 | miRNA | 137 |
| ENSG00000212377 | −0.45 | 0.002249473 | 0.676 | snoRNA | 31 |
| U45A | −0.44 | 0.002283826 | 0.686 | CDBox | 74 |

TABLE 1-continued miRNAs significantly expressed between melanoma and nevi

| Probe Name | Log2-FC | P value | AUC | ProbeType | #Sample Detected |
|---|---|---|---|---|---|
| miR-34a-star | 0.61 | 0.002356105 | 0.682 | miRNA | 39 |
| miR-378-star | 0.71 | 0.002495647 | 0.710 | miRNA | 82 |
| miR-509-5p | 0.98 | 0.002612774 | 0.705 | miRNA | 81 |
| miR-34a | 0.79 | 0.00270219 | 0.676 | miRNA | 132 |
| ACA2a | 0.41 | 0.002741773 | 0.690 | HAcaBox | 55 |
| miR-98 | 0.63 | 0.002795533 | 0.698 | miRNA | 47 |
| miR-337-3p | −0.59 | 0.002924904 | 0.709 | miRNA | 94 |
| U58A | −0.37 | 0.002957231 | 0.667 | CDBox | 129 |
| miR-30e | 0.66 | 0.003008812 | 0.673 | miRNA | 57 |
| miR-196a | 0.99 | 0.003061353 | 0.686 | miRNA | 77 |
| miR-17-star | 0.87 | 0.003088295 | 0.675 | miRNA | 56 |
| HBII-429 | −0.26 | 0.003238494 | 0.681 | CDBox | 137 |
| HBII-85-5__x | 0.38 | 0.003305314 | 0.678 | CDBox | 31 |
| miR-191-star | −0.50 | 0.003313493 | 0.701 | miRNA | 54 |
| U102 | −0.32 | 0.003411715 | 0.662 | CDBox | 124 |
| ACA57 | −0.35 | 0.003594842 | 0.737 | scaRna | 135 |
| HBII-234__x | −0.33 | 0.003636016 | 0.676 | CDBox | 102 |
| hsa-let-7i | 0.62 | 0.003881627 | 0.748 | miRNA | 135 |
| spike__in-control-23 | −0.30 | 0.003884651 | 0.673 | Oligonucleotide spike-in controls | 137 |
| HBII-276 | 0.37 | 0.003895578 | 0.676 | CDBox | 132 |
| mgU6-53 | −0.37 | 0.004017934 | 0.667 | CDBox | 94 |
| miR-575 | −0.55 | 0.004110263 | 0.666 | miRNA | 41 |
| miR-486-5p | 1.06 | 0.004302169 | 0.672 | miRNA | 65 |
| HBII-85-20__x | 0.37 | 0.004413582 | 0.662 | CDBox | 42 |
| U43 | 0.49 | 0.004416752 | 0.847 | CDBox | 135 |
| miR-199b-3p | 0.64 | 0.00460804 | 0.711 | miRNA | 134 |
| U50B | −0.47 | 0.004646908 | 0.678 | CDBox | 135 |
| HBII-202 | −0.37 | 0.004720422 | 0.711 | CDBox | 135 |
| U32A__x | 0.30 | 0.004742469 | 0.634 | CDBox | 136 |
| U28__x | 0.43 | 0.005077583 | 0.733 | CDBox | 133 |
| miR-223 | 0.54 | 0.005512872 | 0.635 | miRNA | 83 |
| U36A | 0.26 | 0.005677159 | 0.654 | CDBox | 132 |
| miR-548a-3p | −0.65 | 0.005852929 | 0.669 | miRNA | 65 |
| U82 | −0.43 | 0.005931718 | 0.686 | CDBox | 131 |
| ACA13 | −0.40 | 0.005934282 | 0.697 | HAcaBox | 134 |
| ENSG00000208308__x | 0.48 | 0.005982879 | 0.755 | snoRNA | 129 |
| 14qI-8 | −0.41 | 0.006020932 | 0.647 | CDBox | 61 |
| ACA41__x | 0.38 | 0.006458897 | 0.687 | HAcaBox | 122 |
| U20 | 0.34 | 0.006504359 | 0.665 | CDBox | 117 |
| HBII-210 | −0.33 | 0.006967845 | 0.684 | CDBox | 135 |
| ACA53 | 0.33 | 0.007009476 | 0.656 | HAcaBox | 105 |
| miR-188-5p | 0.59 | 0.00730559 | 0.668 | miRNA | 51 |
| miR-653 | −0.48 | 0.007396776 | 0.652 | miRNA | 50 |
| ACA18__x | 0.33 | 0.007506763 | 0.656 | HAcaBox | 135 |
| ENSG00000202440__x | −0.29 | 0.007646916 | 0.654 | snoRNA | 91 |
| HBII-180C__x | 0.33 | 0.007676115 | 0.666 | CDBox | 131 |
| ENSG00000200235__x | −0.29 | 0.007854884 | 0.650 | snoRNA | 59 |
| HBII-85-17__x | 0.43 | 0.008991412 | 0.650 | CDBox | 57 |
| miR-205 | 0.39 | 0.009048012 | 0.665 | miRNA | 135 |
| ACA27__x | 0.24 | 0.009084132 | 0.676 | HAcaBox | 130 |
| ACA52 | 0.31 | 0.009338308 | 0.664 | HAcaBox | 121 |
| U8__x | 0.37 | 0.00950871 | 0.638 | CDBox | 135 |
| ENSG00000201229 | 0.35 | 0.009710558 | 0.662 | snoRNA | 32 |
| miR-423-5p | −0.49 | 0.009884603 | 0.704 | miRNA | 132 |
| U72__x | 0.27 | 0.009902439 | 0.642 | HAcaBox | 103 |
| U50 | 0.37 | 0.010130893 | 0.679 | CDBox | 134 |
| miR-34b | 0.95 | 0.010634429 | 0.647 | miRNA | 32 |
| U60 | 0.33 | 0.010937468 | 0.653 | CDBox | 103 |
| ACA26 | −0.38 | 0.011152582 | 0.688 | scaRna | 125 |
| ACA21 | −0.44 | 0.011353671 | 0.661 | HAcaBox | 133 |
| U47 | 0.30 | 0.01143234 | 0.651 | CDBox | 74 |
| miR-26a | 0.40 | 0.011704306 | 0.793 | miRNA | 136 |
| miR-21-star | 0.54 | 0.012900809 | 0.648 | miRNA | 64 |
| U43__x | 0.42 | 0.013355042 | 0.808 | CDBox | 135 |
| HBII-55 | 0.27 | 0.013604568 | 0.636 | CDBox | 135 |
| ACA19 | −0.29 | 0.013694584 | 0.634 | HAcaBox | 118 |
| ENSG00000200897__x | −0.34 | 0.013964134 | 0.628 | snoRNA | 70 |
| ENSG00000207118 | 0.42 | 0.01420542 | 0.652 | snoRNA | 93 |
| U31 | −0.42 | 0.014421405 | 0.684 | CDBox | 132 |
| miR-204 | 0.70 | 0.015040931 | 0.620 | miRNA | 53 |
| miR-195 | 0.59 | 0.01545596 | 0.646 | miRNA | 132 |
| miR-432 | 0.70 | 0.015655418 | 0.649 | miRNA | 51 |
| hsa-let-7c | 0.48 | 0.015958151 | 0.801 | miRNA | 135 |

TABLE 1-continued miRNAs significantly expressed between melanoma and nevi

| Probe Name | Log2-FC | P value | AUC | ProbeType | #Sample Detected |
|---|---|---|---|---|---|
| ACA10_s | 0.33 | 0.015973764 | 0.658 | HAcaBox | 113 |
| miR-1825 | −0.60 | 0.016002367 | 0.679 | miRNA | 132 |
| 14qII-1 | −0.53 | 0.016171959 | 0.621 | CDBox | 128 |
| 14qII-21_x | 0.32 | 0.017134601 | 0.670 | CDBox | 51 |
| U34 | 0.24 | 0.017406393 | 0.609 | CDBox | 137 |
| miR-138-1-star | 0.64 | 0.017790103 | 0.611 | miRNA | 91 |
| miR-1257 | −0.40 | 0.018052873 | 0.633 | miRNA | 31 |
| ACA51_x | −0.23 | 0.018226343 | 0.656 | HAcaBox | 135 |
| 14qII-1_x | −0.50 | 0.018262482 | 0.626 | CDBox | 131 |
| ACA43 | 0.31 | 0.018272258 | 0.620 | HAcaBox | 114 |
| hsa-let-7d | 0.38 | 0.01921824 | 0.855 | miRNA | 135 |
| 14qII-12_x | 0.40 | 0.020581734 | 0.652 | CDBox | 85 |
| 14qII-28_x | 0.34 | 0.02070105 | 0.641 | CDBox | 51 |
| spike_in-control-30 | −0.36 | 0.02072199 | 0.657 | Oligonucleotide spike-in controls | 53 |
| U49B_s | −0.38 | 0.021350114 | 0.648 | CDBox | 129 |
| U45B_x | −0.32 | 0.022203975 | 0.615 | CDBox | 46 |
| miR-125b | 0.42 | 0.022489574 | 0.718 | miRNA | 135 |
| ENSG00000202252 | −0.23 | 0.023928736 | 0.654 | snoRNA | 135 |
| miR-1324 | −0.37 | 0.024126574 | 0.638 | miRNA | 57 |
| HBI-61 | −0.34 | 0.024172419 | 0.639 | HAcaBox | 134 |
| miR-99b-star | 0.34 | 0.024194238 | 0.626 | miRNA | 74 |
| miR-20a | 0.51 | 0.024441924 | 0.640 | miRNA | 134 |
| U54 | 0.36 | 0.02454759 | 0.749 | CDBox | 135 |
| ENSG00000200932 | −0.31 | 0.024839208 | 0.656 | snoRNA | 47 |
| ENSG00000212326 | 0.34 | 0.024965859 | 0.611 | snoRNA | 104 |
| U95 | −0.35 | 0.026080784 | 0.723 | CDBox | 135 |
| miR-193b-star | 0.57 | 0.028801534 | 0.684 | miRNA | 77 |
| ACA5_x | 0.29 | 0.0293861 | 0.662 | HAcaBox | 103 |
| ACA1_x | −0.30 | 0.029505966 | 0.627 | HAcaBox | 51 |
| mgU6-53_x | −0.26 | 0.03076806 | 0.618 | CDBox | 113 |
| U26 | −0.36 | 0.030778322 | 0.608 | CDBox | 135 |
| miR-24 | 0.36 | 0.031162316 | 0.771 | miRNA | 135 |
| spike_in-control-29 | −0.24 | 0.03150161 | 0.615 | Oligonucleotide spike-in controls | 137 |
| miR-19b | 0.57 | 0.03221182 | 0.612 | miRNA | 124 |
| miR-513c | 0.78 | 0.032937767 | 0.632 | miRNA | 73 |
| U42B_x | 0.27 | 0.033688384 | 0.613 | CDBox | 109 |
| miR-20a-star | −0.90 | 0.033742183 | 0.639 | miRNA | 61 |
| U25 | −0.30 | 0.035318167 | 0.655 | CDBox | 135 |
| miR-455-3p | 0.34 | 0.036186611 | 0.643 | miRNA | 136 |
| U109 | 0.32 | 0.036189693 | 0.634 | scaRna | 69 |
| miR-938 | −0.32 | 0.037572276 | 0.639 | miRNA | 45 |
| ENSG00000207503 | −0.27 | 0.037791965 | 0.622 | snoRNA | 42 |
| HBII-289 | −0.24 | 0.041306388 | 0.652 | CDBox | 135 |
| U17b_x | 0.34 | 0.041402099 | 0.728 | HAcaBox | 135 |
| ACA8_x | −0.28 | 0.042136422 | 0.624 | HAcaBox | 125 |
| ACA44 | 0.29 | 0.043557966 | 0.693 | HAcaBox | 135 |
| U45C_x | −0.33 | 0.043838427 | 0.586 | CDBox | 72 |
| ENSG00000201133 | −0.27 | 0.045035669 | 0.645 | snoRNA | 35 |
| ACA55 | −0.26 | 0.045152107 | 0.606 | HAcaBox | 85 |
| miR-451 | 0.53 | 0.046730942 | 0.628 | miRNA | 72 |
| 14qII-26 | −0.32 | 0.047726134 | 0.619 | CDBox | 32 |
| miR-141 | 0.44 | 0.049534195 | 0.627 | miRNA | 69 |

TABLE 2

50 miRNAs most significantly expressed between melanoma and nevi

| Probe Name | Log2-FC | P value | AUC | ProbeType | #Sample Detected |
|---|---|---|---|---|---|
| miR-132 | 2.98 | 1.2728E−32 | 0.994 | miRNA | 96 |
| miR-150 | 3.27 | 5.83192E−30 | 1.000 | miRNA | 117 |
| miR-339-5p | 2.73 | 1.69388E−27 | 0.988 | miRNA | 75 |
| miR-15b | 3.02 | 6.41784E−27 | 0.978 | miRNA | 125 |
| miR-342-3p | 2.23 | 7.03798E−26 | 0.993 | miRNA | 136 |
| miR-572 | −2.78 | 1.00008E−25 | 0.970 | miRNA | 116 |
| miR-155 | 4.14 | 1.28454E−25 | 0.981 | miRNA | 123 |
| miR-425 | 2.74 | 8.13135E−25 | 0.975 | miRNA | 114 |

TABLE 2-continued 50 miRNAs most significantly expressed between melanoma and nevi

| Probe Name | Log2-FC | P value | AUC | ProbeType | #Sample Detected |
|---|---|---|---|---|---|
| miR-1202 | -2.63 | 2.97795E-23 | 0.986 | miRNA | 57 |
| miR-1268 | -2.68 | 6.05905E-23 | 0.997 | miRNA | 133 |
| HBII-382_s | -1.71 | 6.58931E-22 | 0.971 | scaRna | 126 |
| miR-1225-5p | -2.36 | 1.05361E-21 | 0.953 | miRNA | 90 |
| miR-30c | 2.39 | 2.58594E-21 | 0.980 | miRNA | 125 |
| miR-106b-star | 2.24 | 3.48507E-21 | 0.961 | miRNA | 72 |
| miR-125a-5p | 2.39 | 6.90609E-21 | 0.967 | miRNA | 128 |
| mgU6-53B | -1.51 | 1.74782E-20 | 0.973 | CDBox | 99 |
| miR-25 | 2.57 | 1.52769E-19 | 0.956 | miRNA | 118 |
| miR-149-star | -2.03 | 1.64858E-19 | 1.000 | miRNA | 135 |
| miR-939 | -2.21 | 1.9129E-19 | 0.973 | miRNA | 57 |
| miR-92b-star | -2.30 | 2.05085E-19 | 0.969 | miRNA | 111 |
| miR-500-star | 2.38 | 3.11256E-19 | 0.956 | miRNA | 97 |
| miR-22 | 2.69 | 3.8844E-19 | 0.965 | miRNA | 120 |
| HBII-142_x | -1.22 | 4.93318E-19 | 0.981 | CDBox | 135 |
| miR-181b | 2.41 | 1.00639E-18 | 0.960 | miRNA | 130 |
| HBII-142 | -1.33 | 1.18794E-18 | 0.988 | CDBox | 135 |
| U38B | -1.95 | 1.35964E-18 | 0.975 | CDBox | 134 |
| miR-663 | -2.10 | 2.04672E-18 | 0.984 | miRNA | 134 |
| miR-1224-5p | -2.54 | 2.91169E-18 | 0.946 | miRNA | 78 |
| miR-23a | 1.18 | 2.99523E-18 | 0.967 | miRNA | 137 |
| HBII-85-6_x | -1.73 | 4.78418E-18 | 0.939 | CDBox | 137 |
| miR-1207-5p | -2.14 | 4.98991E-18 | 0.995 | miRNA | 133 |
| miR-1301 | 2.36 | 5.22389E-18 | 0.931 | miRNA | 54 |
| miR-1228-star | -2.41 | 5.51513E-18 | 0.997 | miRNA | 134 |
| miR-345 | 2.45 | 6.43552E-18 | 0.942 | miRNA | 75 |
| miR-30a-star | 2.32 | 6.92165E-18 | 0.932 | miRNA | 64 |
| ENSG00000199411_s | -1.97 | 7.23325E-18 | 0.991 | snoRNA | 135 |
| ENSG00000202327 | -1.40 | 8.75839E-18 | 0.938 | snoRNA | 54 |
| miR-92a | 1.67 | 9.49427E-18 | 0.979 | miRNA | 136 |
| miR-127-3p | 2.43 | 9.84615E-18 | 0.936 | miRNA | 89 |
| HBII-85-26 | -2.07 | 1.50619E-17 | 0.951 | CDBox | 136 |
| miR-1308 | -2.14 | 1.99888E-17 | 0.999 | miRNA | 135 |
| miR-31 | 3.29 | 2.46697E-17 | 0.913 | miRNA | 103 |
| miR-921 | -1.46 | 2.61089E-17 | 0.928 | miRNA | 49 |
| miR-146b-5p | 2.37 | 6.10422E-17 | 0.918 | miRNA | 83 |
| miR-768-3p | -1.05 | 6.66153E-17 | 0.949 | miRNA | 137 |
| miR-708 | 2.29 | 6.86187E-17 | 0.929 | miRNA | 102 |
| miR-139-5p | 2.23 | 2.78962E-16 | 0.922 | miRNA | 80 |
| ACA24_x | 1.33 | 3.37973E-16 | 0.925 | HAcaBox | 98 |
| miR-501-3p | 1.83 | 4.76751E-16 | 0.923 | miRNA | 80 |
| miR-502-3p | 2.16 | 5.19509E-16 | 0.925 | miRNA | 110 |
| miR-923 | -1.86 | 5.55191E-16 | 0.996 | miRNA | 135 |

TABLE 3 miRNAs significantly expressed between melanoma and normal skin

| Probe Name | Log2-FC | P value | AUC | ProbeType | #Sample Detected |
|---|---|---|---|---|---|
| miR-146a | 4.6 | 9.43624E-20 | 0.983 | miRNA | 129 |
| miR-509-3p | 5.2 | 5.61558E-17 | 0.969 | miRNA | 116 |
| 14qII-14 | -2.6 | 1.16829E-14 | 0.978 | CDBox | 56 |
| miR-25 | 2.4 | 2.08E-14 | 0.949 | miRNA | 118 |
| miR-138 | 3.2 | 2.51219E-13 | 0.954 | miRNA | 82 |
| miR-509-3-5p | 3.6 | 2.94532E-13 | 0.963 | miRNA | 107 |
| miR-506 | 3.4 | 6.99753E-13 | 0.954 | miRNA | 76 |
| 14qII-14_x | -2.2 | 8.36026E-13 | 0.970 | CDBox | 56 |
| 14qI-4 | -2.1 | 8.9267E-13 | 0.964 | CDBox | 80 |
| miR-30b | 2.2 | 2.43822E-12 | 0.957 | miRNA | 128 |
| miR-513a-5p | 3.5 | 3.17158E-12 | 0.939 | miRNA | 105 |
| miR-21 | 3.3 | 4.58391E-12 | 0.926 | miRNA | 79 |
| Z17B | -1.0 | 6.92137E-12 | 0.956 | CDBox | 117 |
| U33 | -0.9 | 8.19977E-12 | 0.968 | CDBox | 137 |
| miR-20b | 2.8 | 2.24496E-11 | 0.939 | miRNA | 99 |
| hsa-let-7i | 2.3 | 3.27742E-11 | 0.973 | CDBox | 135 |
| HBII-239 | -1.0 | 3.9295E-11 | 0.920 | CDBox | 135 |
| miR-146b-5p | 2.3 | 8.71488E-11 | 0.910 | miRNA | 83 |
| 14qII-26_x | -1.8 | 9.17329E-11 | 0.914 | CDBox | 41 |
| miR-155 | 2.8 | 1.12361E-10 | 0.940 | miRNA | 123 |
| miR-151-3p | 1.8 | 1.7141E-10 | 0.922 | miRNA | 117 |

TABLE 3-continued miRNAs significantly expressed between melanoma and normal skin

| Probe Name | Log2-FC | P value | AUC | ProbeType | #Sample Detected |
|---|---|---|---|---|---|
| HBII-289 | −1.1 | 1.76712E-10 | 0.963 | CDBox | 135 |
| 14qII-12_x | −1.7 | 1.9475E-10 | 0.907 | CDBox | 85 |
| miR-1274a | 1.9 | 3.28343E-10 | 0.928 | miRNA | 48 |
| HBII-180A_x | −0.8 | 4.68853E-10 | 0.933 | CDBox | 123 |
| miR-1301 | 2.0 | 7.22101E-10 | 0.896 | miRNA | 54 |
| 14qII-1_x | −1.7 | 7.72545E-10 | 0.965 | CDBox | 131 |
| miR-193b | −1.4 | 8.7852E-10 | 0.974 | miRNA | 130 |
| miR-510 | 2.7 | 1.03096E-09 | 0.914 | miRNA | 82 |
| miR-126 | 2.1 | 1.35297E-09 | 0.959 | miRNA | 133 |
| miR-24-2-star | 1.8 | 1.36986E-09 | 0.895 | miRNA | 63 |
| miR-106b | 2.1 | 1.91606E-09 | 0.930 | miRNA | 127 |
| HBII-276 | −1.0 | 2.06051E-09 | 0.908 | CDBox | 132 |
| miR-532-5p | 1.8 | 2.9654E-09 | 0.887 | miRNA | 113 |
| 14qII-12 | −1.7 | 3.71443E-09 | 0.859 | CDBox | 58 |
| miR-19b | 2.1 | 3.71682E-09 | 0.908 | miRNA | 124 |
| miR-30a | 1.6 | 6.61873E-09 | 0.894 | miRNA | 113 |
| HBII-85-26_x | −1.1 | 7.76845E-09 | 0.895 | CDBox | 135 |
| miR-150 | 1.7 | 1.08172E-08 | 0.894 | miRNA | 117 |
| 14qII-26 | −1.5 | 1.16704E-08 | 0.869 | CDBox | 32 |
| miR-324-5p | 1.6 | 1.24724E-08 | 0.880 | miRNA | 102 |
| 14qI-8 | −1.2 | 1.39067E-08 | 0.894 | CDBox | 61 |
| miR-185 | 1.6 | 1.44139E-08 | 0.952 | miRNA | 132 |
| miR-194 | 1.8 | 1.72961E-08 | 0.883 | miRNA | 54 |
| 14qII-1 | −1.5 | 2.76507E-08 | 0.928 | CDBox | 128 |
| HBII-202 | −1.0 | 2.89826E-08 | 0.946 | CDBox | 135 |
| miR-768-5p | −1.6 | 3.1365E-08 | 0.986 | miRNA | 135 |
| miR-421 | 1.6 | 4.42916E-08 | 0.872 | miRNA | 68 |
| miR-28-5p | 1.7 | 5.45027E-08 | 0.877 | miRNA | 105 |
| miR-151-5p | 1.2 | 5.48542E-08 | 0.968 | miRNA | 135 |
| miR-15a | 2.0 | 5.77662E-08 | 0.889 | miRNA | 80 |
| miR-26a | 1.3 | 6.8712E-08 | 0.968 | miRNA | 136 |
| U25 | −1.0 | 7.35643E-08 | 0.976 | CDBox | 135 |
| HBII-180C | −0.9 | 7.47464E-08 | 0.836 | CDBox | 115 |
| miR-584 | 1.9 | 8.0812E-08 | 0.863 | miRNA | 57 |
| hsa-let-7f | 2.2 | 1.05873E-07 | 0.924 | miRNA | 130 |
| miR-1268 | −1.7 | 1.09503E-07 | 0.954 | miRNA | 133 |
| miR-572 | −1.4 | 1.12523E-07 | 0.886 | miRNA | 116 |
| ENSG00000200897 | −0.9 | 1.38587E-07 | 0.843 | snoRNA | 38 |
| miR-508-5p | 1.8 | 1.57345E-07 | 0.873 | miRNA | 92 |
| hsa-let-7g | 1.8 | 1.57818E-07 | 0.916 | miRNA | 127 |
| miR-20a | 1.7 | 1.58351E-07 | 0.926 | miRNA | 134 |
| miR-1225-5p | −1.3 | 6.2291E-07 | 0.890 | miRNA | 90 |
| U55 | −0.8 | 1.8721E-07 | 0.942 | CDBox | 135 |
| miR-509-5p | 2.3 | 1.95354E-07 | 0.864 | miRNA | 81 |
| HBII-85-6_x | −1.1 | 2.0107E-07 | 0.872 | CDBox | 137 |
| U99 | −0.7 | 2.22915E-07 | 0.872 | HAcaBox | 137 |
| miR-501-3p | 1.4 | 2.27557E-07 | 0.858 | miRNA | 80 |
| miR-29a | 1.8 | 2.42514E-07 | 0.907 | miRNA | 128 |
| miR-1274b | 1.6 | 2.6096E-07 | 0.863 | miRNA | 112 |
| miR-210 | −1.2 | 2.81748E-07 | 0.895 | miRNA | 130 |
| HBII-85-26 | −1.4 | 3.5949E-07 | 0.896 | CDBox | 136 |
| miR-199a-5p | −0.8 | 3.93185E-07 | 0.870 | miRNA | 129 |
| miR-149 | −1.6 | 5.63545E-07 | 0.920 | miRNA | 100 |
| miR-1307 | −0.9 | 5.6459E-07 | 0.907 | miRNA | 97 |
| miR-744 | −1.1 | 5.78243E-07 | 0.971 | miRNA | 133 |
| miR-92b-star | −1.4 | 6.45948E-07 | 0.907 | miRNA | 111 |
| ACA11 | 0.8 | 7.08497E-07 | 0.842 | HAcaBox | 48 |
| miR-27a | 1.0 | 7.17204E-07 | 0.887 | miRNA | 136 |
| miR-34a-star | 1.4 | 8.89848E-07 | 0.842 | miRNA | 39 |
| U46 | −0.8 | 9.2248E-07 | 0.884 | CDBox | 133 |
| miR-214 | −1.2 | 1.02234E-06 | 0.930 | miRNA | 135 |
| miR-132 | 1.2 | 1.15319E-06 | 0.808 | miRNA | 96 |
| miR-18a | 2.0 | 1.3554E-06 | 0.866 | miRNA | 77 |
| miR-125a-5p | −1.0 | 1.86884E-06 | 0.934 | miRNA | 128 |
| 14qI-8_x | −0.9 | 1.95428E-06 | 0.831 | CDBox | 74 |
| miR-663 | −1.3 | 1.9913E-06 | 0.910 | miRNA | 134 |
| miR-16 | 1.1 | 2.78721E-06 | 0.955 | miRNA | 135 |
| HBII-142_x | −0.8 | 2.95334E-06 | 0.909 | CDBox | 135 |
| U103_s | −0.8 | 3.6466E-06 | 0.825 | CDBox | 111 |
| U55_x | −0.8 | 3.84586E-06 | 0.958 | CDBox | 135 |
| HBII-142 | −0.8 | 3.88875E-06 | 0.917 | CDBox | 135 |
| miR-130b | 1.9 | 4.19812E-06 | 0.858 | miRNA | 90 |
| miR-339-3p | 1.1 | 4.25751E-06 | 0.796 | miRNA | 60 |
| miR-30d | 1.2 | 4.40714E-06 | 0.902 | miRNA | 131 |
| miR-196a | 2.0 | 4.53608E-06 | 0.833 | miRNA | 77 |

TABLE 3-continued miRNAs significantly expressed between melanoma and normal skin

| Probe Name | Log2-FC | P value | AUC | ProbeType | #Sample Detected |
|---|---|---|---|---|---|
| miR-199a-3p | 1.4 | 5.28457E−06 | 0.889 | miRNA | 134 |
| miR-211 | 2.1 | 5.7974E−06 | 0.859 | miRNA | 84 |
| miR-30e | 1.2 | 5.88414E−06 | 0.839 | miRNA | 57 |
| ACA54 | −0.6 | 7.09713E−06 | 0.861 | HAcaBox | 133 |
| miR-106b-star | 1.1 | 7.86756E−06 | 0.720 | miRNA | 72 |
| 14qII-3 | −1.1 | 8.39354E−06 | 0.832 | CDBox | 95 |
| HBII-55 | −0.6 | 8.41728E−06 | 0.860 | CDBox | 135 |
| miR-486-5p | −2.2 | 1.02088E−05 | 0.829 | miRNA | 65 |
| miR-145 | −1.3 | 1.03604E−05 | 0.831 | miRNA | 135 |
| miR-34a | 1.4 | 1.04763E−05 | 0.868 | miRNA | 132 |
| miR-106a | 1.2 | 1.06568E−05 | 0.919 | miRNA | 135 |
| miR-1271 | 1.3 | 1.06608E−05 | 0.829 | miRNA | 70 |
| miR-500 | 1.3 | 1.07278E−05 | 0.816 | miRNA | 86 |
| miR-625 | 1.4 | 1.08708E−05 | 0.800 | miRNA | 59 |
| 14qII-9_x | −0.8 | 1.14849E−05 | 0.821 | CDBox | 36 |
| 14qII-21_x | −0.9 | 1.17647E−05 | 0.797 | CDBox | 51 |
| U83 | −0.6 | 1.19481E−05 | 0.889 | CDBox | 135 |
| miR-638 | −1.3 | 1.34963E−05 | 0.914 | miRNA | 135 |
| HBII-180C_x | −0.6 | 1.39632E−05 | 0.841 | CDBox | 131 |
| ENSG00000212139_x | −0.6 | 1.67825E−05 | 0.831 | snoRNA | 124 |
| miR-628-3p | 1.4 | 1.76296E−05 | 0.811 | miRNA | 38 |
| U104 | −0.8 | 1.84466E−05 | 0.886 | CDBox | 135 |
| miR-10b | 1.2 | 2.02886E−05 | 0.829 | miRNA | 106 |
| U34 | −0.4 | 2.06445E−05 | 0.807 | CDBox | 137 |
| miR-127-3p | −1.1 | 2.16929E−05 | 0.799 | miRNA | 89 |
| 14qII-28_x | −0.9 | 2.21554E−05 | 0.815 | CDBox | 51 |
| miR-1207-5p | −1.2 | 2.25272E−05 | 0.917 | miRNA | 133 |
| miR-199b-3p | 1.3 | 2.29577E−05 | 0.863 | miRNA | 134 |
| U35A | −0.7 | 2.50745E−05 | 0.900 | CDBox | 135 |
| U91_s | −0.8 | 2.92768E−05 | 0.806 | scaRna | 132 |
| spike_in-control-36 | 0.6 | 2.95775E−05 | 0.865 | Oligonucleotide spike-in controls | 137 |
| U32A_x | −0.4 | 3.05381E−05 | 0.827 | CDBox | 136 |
| miR-21-star | 1.2 | 3.24139E−05 | 0.808 | miRNA | 64 |
| miR-149-star | −1.1 | 4.06943E−05 | 0.888 | miRNA | 135 |
| miR-193b-star | −1.4 | 4.09065E−05 | 0.831 | miRNA | 77 |
| U67_x | 0.8 | 4.09255E−05 | 0.792 | HAcaBox | 50 |
| ACA20 | −0.8 | 4.42355E−05 | 0.839 | HAcaBox | 131 |
| miR-1287 | 1.2 | 4.69003E−05 | 0.775 | miRNA | 40 |
| ACA64 | −0.7 | 4.84198E−05 | 0.802 | HAcaBox | 33 |
| U57 | −0.8 | 5.04018E−05 | 0.944 | CDBox | 135 |
| miR-193a-3p | 1.1 | 5.08442E−05 | 0.766 | miRNA | 42 |
| miR-371-5p | 1.1 | 5.19682E−05 | 0.775 | miRNA | 64 |
| HBII-85-8_x | −0.7 | 5.46471E−05 | 0.782 | CDBox | 135 |
| miR-503 | 1.4 | 5.4991E−05 | 0.794 | miRNA | 41 |
| miR-138-1-star | 1.5 | 5.60721E−05 | 0.877 | miRNA | 91 |
| ACA67_x | 0.7 | 5.78125E−05 | 0.790 | HAcaBox | 54 |
| miR-1228-star | −1.3 | 5.81565E−05 | 0.895 | miRNA | 134 |
| U41 | −0.8 | 5.85491E−05 | 0.875 | CDBox | 135 |
| miR-193a-5p | −1.2 | 5.98826E−05 | 0.897 | miRNA | 121 |
| ENSG00000202252 | −0.5 | 6.64141E−05 | 0.839 | snoRNA | 135 |
| 14qI-4_x | −1.0 | 6.7457E−05 | 0.760 | CDBox | 51 |
| miR-508-3p | 1.7 | 6.91432E−05 | 0.801 | miRNA | 74 |
| miR-200b | 1.4 | 7.07093E−05 | 0.779 | miRNA | 109 |
| miR-660 | 1.2 | 7.13979E−05 | 0.791 | miRNA | 71 |
| U67 | 0.8 | 7.16134E−05 | 0.774 | HAcaBox | 44 |
| U50B | −0.8 | 7.249E−05 | 0.869 | CDBox | 135 |
| miR-513c | 1.9 | 7.46404E−05 | 0.771 | miRNA | 73 |
| 14qI-9_x | −0.7 | 7.67649E−05 | 0.772 | CDBox | 34 |
| U60 | −0.6 | 8.34902E−05 | 0.779 | CDBox | 103 |
| U102 | 0.5 | 8.47602E−05 | 0.772 | CDBox | 124 |
| EN8G00000200235_x | −0.5 | 9.4306E−05 | 0.793 | snoRNA | 59 |
| miR-17 | 1.0 | 9.79941E−05 | 0.910 | miRNA | 134 |
| U36C | −0.6 | 0.000107866 | 0.854 | CDBox | 135 |
| miR-491-5p | 0.9 | 0.000121664 | 0.753 | miRNA | 92 |
| miR-425 | 1.0 | 0.000138461 | 0.771 | miRNA | 114 |
| miR-500-star | 1.0 | 0.000148221 | 0.761 | miRNA | 97 |
| U78_x | 1.0 | 0.000150233 | 0.872 | CDBox | 134 |
| ENSG00000202327 | −0.6 | 0.000153478 | 0.783 | snoRNA | 54 |
| miR-181c | 1.1 | 0.000156102 | 0.772 | miRNA | 59 |
| ENSG00000212523_x | −0.8 | 0.000165203 | 0.772 | snoRNA | 135 |
| mgU6-53B_x | −0.5 | 0.00016649 | 0.784 | CDBox | 121 |
| miR-99b-star | 0.8 | 0.00017311 | 0.743 | miRNA | 74 |
| U53 | −0.7 | 0.000175804 | 0.763 | CDBox | 126 |

TABLE 3-continued miRNAs significantly expressed between melanoma and normal skin

| Probe Name | Log2-FC | P value | AUC | ProbeType | #Sample Detected |
|---|---|---|---|---|---|
| miR-296-3p | −1.0 | 0.000180884 | 0.771 | miRNA | 90 |
| U50B_x | −0.7 | 0.000181435 | 0.829 | CDBox | 135 |
| miR-30a-star | 1.2 | 0.00018331 | 0.766 | miRNA | 64 |
| U46_x | −0.8 | 0.000183742 | 0.819 | CDBox | 131 |
| ENSG00000207410_x | −0.5 | 0.000198904 | 0.779 | snoRNA | 55 |
| miR-99a | −0.8 | 0.000204711 | 0.829 | miRNA | 135 |
| miR-513b | 1.4 | 0.000214575 | 0.781 | miRNA | 64 |
| miR-23a | 0.6 | 0.000218135 | 0.908 | miRNA | 137 |
| miR-31 | 1.7 | 0.00023269 | 0.721 | miRNA | 103 |
| miR-345 | 1.2 | 0.000250483 | 0.782 | miRNA | 75 |
| miR-212 | 1.5 | 0.000254534 | 0.831 | miRNA | 62 |
| ENSG00000212266 | −0.6 | 0.000255339 | 0.777 | snoRNA | 93 |
| miR-152 | 1.1 | 0.000260732 | 0.813 | miRNA | 122 |
| U19 | 0.6 | 0.000277432 | 0.757 | HAcaBox | 118 |
| miR-886-3p | 1.0 | 0.000298839 | 0.768 | miRNA | 110 |
| U73a | −0.6 | 0.000338569 | 0.846 | CDBox | 135 |
| miR-423-3p | −0.7 | 0.000347496 | 0.848 | miRNA | 107 |
| mgh28S-2411 | −0.6 | 0.00034785 | 0.901 | CDBox | 135 |
| miR-103 | 0.8 | 0.000430411 | 0.930 | miRNA | 135 |
| miR-629 | 1.1 | 0.000473215 | 0.769 | miRNA | 64 |
| U65 | −0.6 | 0.000562655 | 0.778 | HAcaBox | 128 |
| 14qI-7 | −0.7 | 0.000569692 | 0.803 | CDBox | 51 |
| miR-933 | −0.6 | 0.000572446 | 0.769 | miRNA | 100 |
| miR-205 | −0.6 | 0.000653671 | 0.767 | miRNA | 135 |
| U105 | −0.4 | 0.000692027 | 0.749 | CDBox | 126 |
| miR-378-star | 1.1 | 0.000731339 | 0.769 | miRNA | 82 |
| miR-939 | −0.9 | 0.000748523 | 0.822 | miRNA | 57 |
| hsa-let-7d | 0.8 | 0.000759497 | 0.978 | miRNA | 135 |
| miR-362-5p | 1.2 | 0.000775756 | 0.762 | miRNA | 94 |
| ACA9 | 0.7 | 0.000834583 | 0.739 | HAcaBox | 82 |
| miR-10a | 1.1 | 0.000844868 | 0.759 | miRNA | 69 |
| miR-877 | −0.9 | 0.000845569 | 0.789 | miRNA | 126 |
| miR-128 | 1.1 | 0.000865867 | 0.762 | miRNA | 44 |
| miR-27b | 0.8 | 0.000876954 | 0.799 | miRNA | 133 |
| miR-17-star | 1.2 | 0.000905238 | 0.748 | miRNA | 56 |
| mgh18S-121 | −0.5 | 0.000964406 | 0.789 | CDBox | 134 |
| ENSG00000200394 | 0.5 | 0.000968073 | 0.772 | snoRNA | 119 |
| ENSG00000212315 | 0.6 | 0.000971189 | 0.757 | snoRNA | 117 |
| ENSG00000212615_x | −0.5 | 0.000998331 | 0.707 | snoRNA | 102 |
| miR-148a | 0.9 | 0.001014157 | 0.733 | miRNA | 41 |
| miR-923 | −0.9 | 0.001032772 | 0.826 | miRNA | 135 |
| ACA20_x | −0.6 | 0.001087206 | 0.830 | HAcaBox | 134 |
| ENSG00000212579_x | −0.6 | 0.001126846 | 0.765 | snoRNA | 100 |
| miR-589-star | 0.5 | 0.001225281 | 0.703 | miRNA | 43 |
| miR-107 | 0.7 | 0.001260426 | 0.932 | miRNA | 135 |
| ENSG00000199363 | 0.6 | 0.001425983 | 0.750 | snoRNA | 42 |
| ACA55 | 0.5 | 0.001430114 | 0.746 | HAcaBox | 85 |
| U54 | −0.7 | 0.001511402 | 0.868 | CDBox | 135 |
| U36A | −0.4 | 0.001519955 | 0.759 | CDBox | 132 |
| U95 | −0.7 | 0.001551616 | 0.929 | CDBox | 135 |
| 14qII-22_x | −0.7 | 0.001591836 | 0.701 | CDBox | 50 |
| U58B_x | −0.5 | 0.001603166 | 0.726 | CDBox | 132 |
| miR-720 | 0.7 | 0.001622509 | 0.760 | miRNA | 137 |
| ENSG00000200394_x | 0.5 | 0.001742151 | 0.711 | snoRNA | 115 |
| HBII-166 | −0.5 | 0.001874456 | 0.769 | CDBox | 134 |
| miR-29b-1-star | 1.3 | 0.001938943 | 0.736 | miRNA | 46 |
| HBII-436 | −0.5 | 0.001978078 | 0.731 | CDBox | 102 |
| U23 | −0.5 | 0.002014594 | 0.748 | HAcaBox | 127 |
| miR-346 | −0.9 | 0.002054981 | 0.774 | miRNA | 55 |
| U58A | −0.5 | 0.002095349 | 0.735 | CDBox | 129 |
| HBII-95 | 0.5 | 0.00219824 | 0.703 | CDBox | 78 |
| miR-339-5p | 0.7 | 0.002357824 | 0.693 | miRNA | 75 |
| ACA25 | 0.4 | 0.002440171 | 0.724 | HAcaBox | 73 |
| miR-363 | 1.1 | 0.002716266 | 0.735 | miRNA | 44 |
| miR-432 | −1.1 | 0.002752773 | 0.738 | miRNA | 51 |
| miR-424-star | 1.1 | 0.002765097 | 0.718 | miRNA | 41 |
| U27 | −0.6 | 0.002765603 | 0.792 | CDBox | 134 |
| miR-30c | 0.6 | 0.002778453 | 0.770 | miRNA | 125 |
| miR-93 | 0.7 | 0.002813996 | 0.863 | miRNA | 134 |
| hsa-let-7a | 0.8 | 0.002856983 | 0.911 | miRNA | 136 |
| miR-181d | 1.0 | 0.002954008 | 0.748 | miRNA | 61 |
| miR-99b | −0.5 | 0.00296227 | 0.757 | miRNA | 129 |
| miR-550-star | 0.9 | 0.003086147 | 0.740 | miRNA | 58 |
| U43 | −0.7 | 0.00327637 | 0.865 | CDBox | 135 |
| U52 | −0.5 | 0.003332494 | 0.783 | CDBox | 135 |

TABLE 3-continued miRNAs significantly expressed between melanoma and normal skin

| Probe Name | Log2-FC | P value | AUC | ProbeType | #Sample Detected |
|---|---|---|---|---|---|
| miR-502-3p | 0.8 | 0.003628993 | 0.775 | miRNA | 110 |
| spike_in-control-29 | −0.4 | 0.003663934 | 0.723 | Oligonucleotide spike-in controls | 137 |
| 14qII-17 | −0.7 | 0.003689916 | 0.703 | CDBox | 71 |
| ENSG00000212302_x | −0.4 | 0.003876466 | 0.676 | snoRNA | 56 |
| miR-574-3p | −0.7 | 0.003955226 | 0.842 | miRNA | 122 |
| miR-320d | −0.8 | 0.004248663 | 0.868 | miRNA | 134 |
| miR-1246 | 1.0 | 0.004275913 | 0.772 | miRNA | 131 |
| ACA7_s | −0.4 | 0.004475709 | 0.719 | HAcaBox | 133 |
| miR-15b | 0.6 | 0.004714973 | 0.792 | miRNA | 125 |
| HBII-52-37_x | −0.5 | 0.004773282 | 0.714 | CDBox | 37 |
| gi555853_copy0 | −0.6 | 0.004784885 | 0.799 | 5.8s rRNA | 137 |
| miR-30e-star | 0.8 | 0.00500785 | 0.717 | miRNA | 35 |
| miR-18a-star | 0.8 | 0.005024206 | 0.723 | miRNA | 40 |
| ENSG00000201847_x | −0.4 | 0.005059414 | 0.688 | snoRNA | 48 |
| gi555853_copy5 | −0.5 | 0.005220274 | 0.809 | 5.8s rRNA | 137 |
| U24 | −0.4 | 0.005634443 | 0.708 | CDBox | 133 |
| miR-1280 | −0.4 | 0.005689807 | 0.740 | miRNA | 134 |
| miR-1231 | −0.8 | 0.005810993 | 0.676 | miRNA | 79 |
| ENSG00000202498_x | −0.5 | 0.005898128 | 0.701 | snoRNA | 137 |
| gi555853_copy7 | −0.5 | 0.006325433 | 0.804 | 5.8s rRNA | 137 |
| miR-28-3p | 0.9 | 0.006506887 | 0.711 | miRNA | 94 |
| ENSG00000199435 | 0.4 | 0.006656491 | 0.706 | snoRNA | 63 |
| gi555853_copy2 | −0.5 | 0.00671481 | 0.800 | 5.8s rRNA | 137 |
| U43_x | −0.6 | 0.006913554 | 0.854 | CDBox | 135 |
| ENSG00000212273_x | −0.5 | 0.007104981 | 0.725 | snoRNA | 126 |
| ENSG00000200961 | −0.4 | 0.007247826 | 0.716 | snoRNA | 41 |
| U38A | −0.7 | 0.007390068 | 0.814 | CDBox | 134 |
| E3_x | −0.4 | 0.007704052 | 0.779 | HAcaBox | 135 |
| gi555853_copy8 | −0.5 | 0.00776022 | 0.799 | 5.8s rRNA | 137 |
| HBII-234_x | −0.3 | 0.007814833 | 0.703 | CDBox | 102 |
| U28 | −0.5 | 0.008026327 | 0.771 | CDBox | 135 |
| ENSG00000212587 | −0.5 | 0.008211191 | 0.685 | snoRNA | 45 |
| ENSG00000212149_x | −0.5 | 0.008233504 | 0.678 | snoRNA | 77 |
| HBII-420 | −0.5 | 0.00828299 | 0.771 | CDBox | 131 |
| gi555853_copy1 | −0.5 | 0.008395769 | 0.791 | 5.8s rRNA | 137 |
| HBII-85-21_x | 0.5 | 0.008439987 | 0.717 | CDBox | 39 |
| gi555853_copy4 | −0.5 | 0.008541113 | 0.793 | 5.8s rRNA | 137 |
| gi555853_copy6 | −0.5 | 0.008815947 | 0.792 | 5.8s rRNA | 137 |
| ENSG00000200897_x | −0.5 | 0.009024011 | 0.686 | snoRNA | 70 |
| ENSG00000207002 | −0.4 | 0.009046282 | 0.706 | snoRNA | 35 |
| ENSG00000212627 | −0.4 | 0.009345896 | 0.714 | snoRNA | 69 |
| gi555853_copy3 | −0.5 | 0.009628403 | 0.777 | 5.8s rRNA | 137 |
| HBII-85-17_x | 0.5 | 0.009677702 | 0.685 | CDBox | 57 |
| miR-92b | 0.5 | 0.009817789 | 0.672 | miRNA | 91 |
| HBII-210 | −0.4 | 0.009959111 | 0.756 | CDBox | 135 |
| ACA3 | −0.5 | 0.010166004 | 0.740 | HAcaBox | 134 |
| miR-769-5p | 0.7 | 0.010207709 | 0.622 | miRNA | 56 |
| U100 | 0.4 | 0.010232137 | 0.645 | scaRna | 80 |
| U13 | −0.4 | 0.010247574 | 0.720 | CDBox | 135 |
| miR-181b | 0.6 | 0.010316868 | 0.816 | miRNA | 130 |
| ACA46 | 0.4 | 0.010365242 | 0.699 | HAcaBox | 124 |
| gi555853_copy9 | −0.5 | 0.010460125 | 0.788 | 5.8s rRNA | 137 |
| U70_x | −0.5 | 0.011265988 | 0.704 | HAcaBox | 53 |
| HBII-85-15_x | 0.5 | 0.011411104 | 0.695 | CDBox | 49 |
| miR-203 | 0.7 | 0.01182754 | 0.822 | miRNA | 132 |
| miR-320c | −0.6 | 0.011901129 | 0.845 | miRNA | 135 |
| miR-191-star | −0.6 | 0.012197187 | 0.680 | miRNA | 54 |
| ACA18_x | −0.4 | 0.012258626 | 0.694 | HAcaBox | 135 |
| miR-27a-star | 0.8 | 0.013060406 | 0.702 | miRNA | 40 |
| miR-192 | 0.7 | 0.013123545 | 0.703 | miRNA | 32 |
| U74_x | 0.5 | 0.013418084 | 0.804 | CDBox | 135 |
| ACA15_x | −0.3 | 0.013532632 | 0.691 | HAcaBox | 124 |
| miR-198 | −0.6 | 0.013839541 | 0.687 | miRNA | 31 |
| U28_x | −0.5 | 0.013863106 | 0.711 | CDBox | 133 |
| ACA28 | 0.4 | 0.013886424 | 0.685 | HAcaBox | 120 |
| U97 | −0.4 | 0.013970203 | 0.692 | CDBox | 133 |
| ACA4 | 0.3 | 0.014571497 | 0.655 | HAcaBox | 117 |
| miR-423-5p | −0.6 | 0.015447652 | 0.754 | miRNA | 132 |
| ACA25_x | 0.4 | 0.015584731 | 0.701 | HAcaBox | 114 |
| HBII-382_s | −0.4 | 0.016066802 | 0.670 | scaRna | 126 |
| miR-34b | 1.2 | 0.016083233 | 0.693 | miRNA | 32 |
| miR-181a-2-star | 0.7 | 0.016427521 | 0.646 | miRNA | 99 |
| U15B | −0.3 | 0.017584552 | 0.689 | CDBox | 129 |

TABLE 3-continued miRNAs significantly expressed between melanoma and normal skin

| Probe Name | Log2-FC | P value | AUC | ProbeType | #Sample Detected |
|---|---|---|---|---|---|
| miR-361-5p | 0.4 | 0.017617483 | 0.783 | miRNA | 135 |
| ACA9__x | 0.5 | 0.017621407 | 0.669 | HAcaBox | 77 |
| ACA15__s | −0.3 | 0.017633335 | 0.738 | HAcaBox | 116 |
| miR-23b-star | 0.7 | 0.018210894 | 0.672 | miRNA | 52 |
| ACA60 | −0.3 | 0.018634054 | 0.702 | HAcaBox | 129 |
| 14q-0 | −0.4 | 0.019666039 | 0.681 | CDBox | 49 |
| HBII-85-22__x | 0.5 | 0.019999179 | 0.673 | CDBox | 42 |
| miR-30b-star | 0.9 | 0.020172985 | 0.686 | miRNA | 61 |
| miR-125b | −0.5 | 0.020376572 | 0.707 | miRNA | 135 |
| ENSG00000199411__s | −0.6 | 0.020504379 | 0.779 | snoRNA | 135 |
| HBII-251 | −0.3 | 0.020538747 | 0.679 | CDBox | 135 |
| miR-483-3p | 0.9 | 0.020547545 | 0.666 | miRNA | 40 |
| ACA23 | −0.3 | 0.021199129 | 0.685 | HAcaBox | 113 |
| ENSG00000212432__s | −0.4 | 0.021742945 | 0.649 | snoRNA | 75 |
| miR-25-star | 0.7 | 0.022483461 | 0.671 | miRNA | 52 |
| ENSG00000200932 | −0.3 | 0.023007003 | 0.687 | snoRNA | 47 |
| U49B__s | 0.5 | 0.023157964 | 0.726 | CDBox | 129 |
| ENSG00000212214__x | 0.4 | 0.023504965 | 0.687 | snoRNA | 88 |
| U83B | −0.4 | 0.024471226 | 0.745 | CDBox | 135 |
| miR-320b | −0.6 | 0.025686249 | 0.790 | miRNA | 135 |
| miR-489 | 0.6 | 0.025963923 | 0.680 | miRNA | 58 |
| miR-26b | 0.7 | 0.026201573 | 0.682 | miRNA | 45 |
| U14B | −0.4 | 0.027046414 | 0.632 | CDBox | 51 |
| HBII-115 | −0.3 | 0.027115569 | 0.730 | CDBox | 117 |
| ENSG00000207027 | −0.4 | 0.028391297 | 0.621 | snoRNA | 36 |
| miR-494 | 0.5 | 0.029570695 | 0.689 | miRNA | 135 |
| miR-181a-star | 0.7 | 0.030787798 | 0.668 | miRNA | 35 |
| U49A__x | 0.4 | 0.03088655 | 0.750 | CDBox | 135 |
| ACA14b__x | −0.3 | 0.030912946 | 0.693 | HAcaBox | 105 |
| U21 | −0.4 | 0.031731894 | 0.691 | CDBox | 134 |
| HBII-135__x | 0.6 | 0.032076241 | 0.663 | CDBox | 132 |
| miR-382 | 0.8 | 0.032245385 | 0.651 | miRNA | 47 |
| miR-532-3p | 0.4 | 0.032767036 | 0.697 | miRNA | 95 |
| miR-214-star | 0.8 | 0.032818193 | 0.670 | miRNA | 47 |
| mgU6-53B | −0.3 | 0.033293267 | 0.663 | CDBox | 99 |
| miR-200c | −0.7 | 0.033609817 | 0.659 | miRNA | 134 |
| miR-575 | 0.5 | 0.034489882 | 0.657 | miRNA | 41 |
| mgU6-53 | −0.3 | 0.034658143 | 0.674 | CDBox | 94 |
| miR-422a | 0.8 | 0.035772116 | 0.674 | miRNA | 84 |
| ENSG00000201848 | −0.3 | 0.036190647 | 0.652 | snoRNA | 34 |
| ACA45 | 0.3 | 0.036575475 | 0.653 | scaRna | 53 |
| miR-559 | −0.5 | 0.036810259 | 0.647 | miRNA | 72 |
| ACA61 | −0.4 | 0.037187144 | 0.716 | HAcaBox | 135 |
| snR38C | −0.4 | 0.037656608 | 0.721 | CDBox | 134 |
| HBII-85-23__x | 0.5 | 0.037660456 | 0.650 | CDBox | 58 |
| miR-551b-star | −0.5 | 0.037971736 | 0.645 | miRNA | 61 |
| miR-27b-star | 0.7 | 0.041289539 | 0.663 | miRNA | 51 |
| U50 | −0.4 | 0.041514005 | 0.696 | CDBox | 134 |
| ACA58__x | 0.3 | 0.041793061 | 0.653 | HAcaBox | 89 |
| ACA53 | −0.3 | 0.0421874 | 0.635 | HAcaBox | 105 |
| U49A | 0.4 | 0.042284609 | 0.694 | CDBox | 135 |
| ACA16 | −0.4 | 0.042968027 | 0.658 | HAcaBox | 47 |
| ACA13 | −0.4 | 0.043493352 | 0.722 | HAcaBox | 134 |
| miR-320a | −0.5 | 0.043683231 | 0.755 | miRNA | 135 |
| ENSG00000200969 | −0.4 | 0.043904585 | 0.663 | snoRNA | 67 |
| miR-642 | −0.4 | 0.04542452 | 0.640 | miRNA | 69 |
| miR-148b | 0.5 | 0.046811178 | 0.645 | miRNA | 32 |
| U84 | −0.2 | 0.046963896 | 0.683 | CDBox | 131 |
| U56__x | 0.4 | 0.047943262 | 0.701 | CDBox | 134 |
| miR-451 | 0.7 | 0.049304242 | 0.632 | miRNA | 72 |
| miR-195 | 0.6 | 0.049397144 | 0.698 | miRNA | 132 |

TABLE 4

50 miRNAs most significantly expressed between melanoma and normal skin

| Probe Name | Log2-FC | P value | AUC | ProbeType | #Sample Detected |
|---|---|---|---|---|---|
| miR-146a | 4.6 | 9.43624E−20 | 0.983 | miRNA | 129 |
| miR-509-3p | 5.2 | 5.61558E−17 | 0.969 | miRNA | 116 |
| 14qII-14 | −2.6 | 1.16829E−14 | 0.978 | CDBox | 56 |
| miR-25 | 2.4 | 2.08E−14 | 0.949 | miRNA | 118 |

TABLE 4-continued

50 miRNAs most significantly expressed between melanoma and normal skin

| Probe Name | Log2-FC | P value | AUC | ProbeType | #Sample Detected |
|---|---|---|---|---|---|
| miR-138 | 3.2 | 2.51219E−13 | 0.954 | miRNA | 82 |
| miR-509-3-5p | 3.6 | 2.94532E−13 | 0.963 | miRNA | 107 |
| miR-506 | 3.4 | 6.99753E−13 | 0.954 | miRNA | 76 |
| 14qII-14_x | −2.2 | 8.36026E−13 | 0.970 | CDBox | 56 |
| 14qI-4 | −2.1 | 8.9267E−13 | 0.964 | CDBox | 80 |
| miR-30b | 2.2 | 2.43822E−12 | 0.957 | miRNA | 128 |
| miR-513a-5p | 3.5 | 3.17158E−12 | 0.939 | miRNA | 105 |
| miR-21 | 3.3 | 4.58391E−12 | 0.926 | miRNA | 79 |
| Z17B | −1.0 | 6.92137E−12 | 0.956 | CDBox | 117 |
| U33 | −0.9 | 8.19977E−12 | 0.968 | CDBox | 137 |
| miR-20b | 2.8 | 2.24496E−11 | 0.939 | miRNA | 99 |
| hsa-let-7i | 2.3 | 3.27742E−11 | 0.973 | miRNA | 135 |
| HBII-239 | −1.0 | 3.9295E−11 | 0.920 | CDBox | 135 |
| miR-146b-5p | 2.3 | 8.71488E−11 | 0.910 | miRNA | 83 |
| 14qII-26_x | −1.8 | 9.17329E−11 | 0.914 | CDBox | 41 |
| miR-155 | 2.8 | 1.12361E−10 | 0.940 | miRNA | 123 |
| miR-151-3p | 1.8 | 1.7141E−10 | 0.922 | miRNA | 117 |
| HBII-289 | −1.1 | 1.76712E−10 | 0.963 | CDBox | 135 |
| 14qII-12_x | −1.7 | 1.9475E−10 | 0.907 | CDBox | 85 |
| miR-1274a | 1.9 | 3.28343E−10 | 0.928 | miRNA | 48 |
| HBII-180A_x | −0.8 | 4.68853E−10 | 0.933 | CDBox | 123 |
| miR-1301 | 2.0 | 7.22101E−10 | 0.896 | miRNA | 54 |
| 14qII-1_x | −1.7 | 7.72545E−10 | 0.965 | CDBox | 131 |
| miR-193b | −1.4 | 8.7852E−10 | 0.974 | miRNA | 130 |
| miR-510 | 2.7 | 1.03096E−09 | 0.914 | miRNA | 82 |
| miR-126 | 2.1 | 1.35297E−09 | 0.959 | miRNA | 133 |
| miR-24-2-star | 1.8 | 1.36986E−09 | 0.895 | miRNA | 63 |
| miR-106b | 2.1 | 1.91606E−09 | 0.930 | miRNA | 127 |
| HBII-276 | −1.0 | 2.06051E−09 | 0.908 | CDBox | 132 |
| miR-532-5p | 1.8 | 2.9654E−09 | 0.887 | miRNA | 113 |
| 14qII-12 | −1.7 | 3.71443E−09 | 0.859 | CDBox | 58 |
| miR-19b | 2.1 | 3.71682E−09 | 0.908 | miRNA | 124 |
| miR-30a | 1.6 | 6.61873E−09 | 0.894 | miRNA | 113 |
| HBII-85-26_x | −1.1 | 7.76845E−09 | 0.895 | CDBox | 135 |
| miR-150 | 1.7 | 1.08172E−08 | 0.894 | miRNA | 117 |
| 14qII-26 | −1.5 | 1.16704E−08 | 0.869 | CDBox | 32 |
| miR-324-5p | 1.6 | 1.24724E−08 | 0.880 | miRNA | 102 |
| 14qI-8 | −1.2 | 1.39067E−08 | 0.894 | CDBox | 61 |
| miR-185 | 1.6 | 1.44139E−08 | 0.952 | miRNA | 132 |
| miR-194 | 1.8 | 1.72961E−08 | 0.883 | miRNA | 54 |
| 14qII-1 | −1.5 | 2.76507E−08 | 0.928 | CDBox | 128 |
| HBII-202 | −1.0 | 2.89826E−08 | 0.946 | CDBox | 135 |
| miR-768-5p | −1.6 | 3.1365E−08 | 0.986 | miRNA | 135 |
| miR-421 | 1.6 | 4.42916E−08 | 0.872 | miRNA | 68 |
| miR-28-5p | 1.7 | 5.45027E−08 | 0.877 | miRNA | 105 |
| miR-151-5p | 1.2 | 5.48542E−08 | 0.968 | miRNA | 135 |

TABLE 5 miRNAs significantly expressed between metastatic melanoma and melanoma

| Probe Name | Log2-FC | P value | AUC | ProbeType | #Sample Detected |
|---|---|---|---|---|---|
| miR-31 | −2.4 | 6.23649E−09 | 0.891 | miRNA | 103 |
| miR-150 | −1.2 | 4.84574E−06 | 0.783 | miRNA | 117 |
| miR-203 | −2.0 | 2.77555E−05 | 0.764 | miRNA | 132 |
| ENSG00000212139_x | 0.6 | 2.83257E−05 | 0.799 | snoRNA | 124 |
| mgU6-53 | 0.6 | 3.8628E−05 | 0.828 | CDBox | 94 |
| U72_x | 0.5 | 4.47709E−05 | 0.783 | HAcaBox | 103 |
| U94 | 0.6 | 7.34024E−05 | 0.776 | CDBox | 109 |
| HBII-85-15_x | 0.8 | 0.000176472 | 0.767 | CDBox | 49 |
| HBII-85-29_x | 0.8 | 0.000274959 | 0.734 | CDBox | 85 |
| HBII-55 | 0.5 | 0.000331716 | 0.806 | CDBox | 135 |
| snR38B | 0.8 | 0.000374886 | 0.750 | CDBox | 126 |
| miR-200c | −1.6 | 0.00042063 | 0.718 | miRNA | 134 |
| U61 | 0.7 | 0.000440758 | 0.785 | CDBox | 116 |
| HBII-316 | 0.6 | 0.000548042 | 0.744 | CDBox | 130 |
| U32A_x | 0.4 | 0.000553879 | 0.748 | CDBox | 136 |
| U81_x | 0.6 | 0.000598062 | 0.720 | CDBox | 120 |
| U15A | 0.7 | 0.000649777 | 0.785 | CDBox | 128 |
| ACA14b_x | 0.4 | 0.000764147 | 0.748 | HAcaBox | 105 |
| miR-182 | −0.9 | 0.000868427 | 0.762 | miRNA | 113 |
| miR-455-3p | −0.7 | 0.000874654 | 0.718 | miRNA | 136 |
| miR-532-5p | −0.8 | 0.000883675 | 0.752 | miRNA | 113 |
| mgU6-53_x | 0.5 | 0.001038416 | 0.783 | CDBox | 113 |
| ACA46 | 0.4 | 0.001076758 | 0.746 | HAcaBox | 124 |
| miR-1234 | −0.5 | 0.001112272 | 0.756 | miRNA | 68 |
| U53 | 0.6 | 0.001130502 | 0.769 | CDBox | 126 |
| HBII-85-29 | 0.7 | 0.001192467 | 0.702 | CDBox | 82 |
| U47 | 0.5 | 0.001218674 | 0.702 | CDBox | 74 |
| U42B_x | 0.5 | 0.001412559 | 0.735 | CDBox | 109 |
| miR-155 | −1.3 | 0.001425842 | 0.716 | miRNA | 123 |
| U64 | 0.5 | 0.001493551 | 0.728 | HAcaBox | 101 |
| ACA28 | 0.5 | 0.001565276 | 0.692 | HAcaBox | 120 |
| U13 | 0.6 | 0.001630341 | 0.748 | CDBox | 135 |
| U84 | 0.4 | 0.001673776 | 0.769 | CDBox | 131 |
| U22 | 0.5 | 0.001739769 | 0.714 | CDBox | 135 |
| U46_x | 0.6 | 0.001758635 | 0.755 | CDBox | 131 |
| ACA17_x | 0.6 | 0.001827243 | 0.705 | HAcaBox | 44 |
| ENSG00000200897 | 0.4 | 0.001857043 | 0.735 | snoRNA | 38 |
| U36A_x | 0.4 | 0.00192703 | 0.728 | CDBox | 133 |
| HBII-180C | 0.4 | 0.001987135 | 0.757 | CDBox | 115 |
| HBII-251 | 0.4 | 0.0020213 | 0.741 | CDBox | 135 |

TABLE 5-continued miRNAs significantly expressed between metastatic melanoma and melanoma

| Probe Name | Log2-FC | P value | AUC | ProbeType | #Sample Detected |
|---|---|---|---|---|---|
| ACA49 | 0.4 | 0.002175278 | 0.744 | HAcaBox | 127 |
| U19 | 0.6 | 0.00221226 | 0.696 | HAcaBox | 118 |
| miR-940 | −0.6 | 0.002377881 | 0.713 | miRNA | 53 |
| U76 | 0.6 | 0.002408733 | 0.755 | CDBox | 135 |
| HBII-13_x | 0.7 | 0.002521867 | 0.730 | CDBox | 60 |
| HBII-382_s | 0.6 | 0.002554678 | 0.770 | scaRna | 126 |
| miR-205 | −1.1 | 0.002610442 | 0.603 | miRNA | 135 |
| U21 | 0.7 | 0.002613305 | 0.774 | CDBox | 134 |
| miR-342-3p | −0.5 | 0.002621512 | 0.706 | miRNA | 136 |
| ENSG00000212326 | 0.5 | 0.002879558 | 0.728 | snoRNA | 104 |
| U82 | 0.7 | 0.002979246 | 0.828 | CDBox | 131 |
| HBII-234_x | 0.3 | 0.003087142 | 0.734 | CDBox | 102 |
| HBII-85-24_x | 0.4 | 0.003172633 | 0.703 | CDBox | 34 |
| U101 | 0.5 | 0.003644287 | 0.672 | CDBox | 134 |
| U46 | 0.5 | 0.003690792 | 0.747 | CDBox | 133 |
| U58A | 0.5 | 0.003778891 | 0.735 | CDBox | 129 |
| HBII-210 | 0.5 | 0.003785668 | 0.767 | CDBox | 135 |
| U102 | 0.4 | 0.00401337 | 0.705 | CDBox | 124 |
| HBII-85-3_x | 0.5 | 0.004030857 | 0.694 | CDBox | 72 |
| U92 | 0.4 | 0.004575813 | 0.712 | scaRna | 129 |
| spike_in-control-31 | 0.1 | 0.004779896 | 0.705 | Oligonucleotide spike-in controls | 137 |
| snR38C | 0.6 | 0.005413855 | 0.779 | CDBox | 134 |
| HBII-99 | 0.5 | 0.005634509 | 0.714 | CDBox | 122 |
| ACA47 | 0.5 | 0.006095831 | 0.696 | scaRna | 77 |
| HBII-420 | 0.6 | 0.006404916 | 0.824 | CDBox | 131 |
| ENSG00000212423_x | 0.5 | 0.006424898 | 0.684 | snoRNA | 115 |
| HBII-85-17_x | 0.6 | 0.006577979 | 0.678 | CDBox | 57 |
| ACA27_x | 0.3 | 0.006580858 | 0.725 | HAcaBox | 130 |
| U79 | 0.6 | 0.007498133 | 0.748 | CDBox | 134 |
| U107 | 0.4 | 0.00761608 | 0.707 | HAcaBox | 129 |
| HBI-43 | 0.3 | 0.007872874 | 0.691 | CDBox | 122 |
| U49B_x | 0.5 | 0.008037057 | 0.736 | CDBox | 122 |
| miR-548i | −0.5 | 0.008242048 | 0.684 | miRNA | 36 |
| miR-500-star | −0.6 | 0.008434274 | 0.697 | miRNA | 97 |
| HBII-85-2_x | 0.4 | 0.008511275 | 0.708 | CDBox | 135 |
| ACA41 | 0.5 | 0.008991193 | 0.723 | HAcaBox | 115 |
| ACA3 | 0.5 | 0.009231708 | 0.737 | HAcaBox | 134 |
| U49A | 0.6 | 0.009381377 | 0.745 | CDBox | 135 |
| HBII-85-20_x | 0.5 | 0.00942941 | 0.672 | CDBox | 42 |
| ENSG00000212508 | −0.5 | 0.009471802 | 0.712 | snoRNA | 122 |
| U38B_x | 0.7 | 0.009547747 | 0.837 | CDBox | 133 |
| ACA51_x | 0.3 | 0.009599762 | 0.686 | HAcaBox | 135 |
| ENSG00000200879 | 0.5 | 0.009860049 | 0.697 | snoRNA | 120 |
| miR-181a | −0.6 | 0.009890715 | 0.730 | miRNA | 134 |
| ENSG00000200932 | 0.4 | 0.010075893 | 0.740 | snoRNA | 47 |
| miR-589-star | −0.4 | 0.010240715 | 0.650 | miRNA | 43 |
| ENSG00000199262 | 0.4 | 0.010309025 | 0.694 | snoRNA | 59 |
| miR-1324 | −0.5 | 0.010648472 | 0.724 | miRNA | 57 |
| U91_s | 0.5 | 0.010903574 | 0.695 | scaRna | 132 |
| U3-2_s | 0.5 | 0.011269742 | 0.729 | CDBox | 135 |
| U51_x | 0.4 | 0.011519055 | 0.713 | CDBox | 130 |
| ACA9 | 0.5 | 0.012046848 | 0.703 | HAcaBox | 82 |
| miR-1825 | −0.8 | 0.01292318 | 0.738 | miRNA | 132 |
| mgU6-47 | 0.4 | 0.013536315 | 0.710 | CDBox | 47 |
| miR-1281 | −0.7 | 0.014086281 | 0.701 | miRNA | 137 |
| U71d_x | 0.5 | 0.01413005 | 0.678 | HAcaBox | 99 |
| ACA42 | 0.4 | 0.014283243 | 0.786 | HAcaBox | 117 |
| ACA34 | 0.3 | 0.014399902 | 0.637 | HAcaBox | 109 |
| U48 | 0.4 | 0.014650847 | 0.654 | CDBox | 129 |
| ENSG00000202093 | 0.5 | 0.014675533 | 0.689 | snoRNA | 97 |
| miR-665 | 0.5 | 0.014853517 | 0.678 | miRNA | 47 |
| miR-141 | −0.7 | 0.015316578 | 0.647 | miRNA | 69 |
| U23 | 0.4 | 0.015408258 | 0.701 | HAcaBox | 127 |
| U15B | 0.4 | 0.015684928 | 0.719 | CDBox | 129 |
| miR-1274b | 0.6 | 0.01695735 | 0.679 | miRNA | 112 |
| U31_x | 0.5 | 0.017818548 | 0.771 | CDBox | 135 |
| ENSG00000200394_x | 0.4 | 0.017859341 | 0.682 | snoRNA | 115 |
| ACA67_x | 0.4 | 0.018242565 | 0.663 | HAcaBox | 54 |
| U80 | 0.4 | 0.019116778 | 0.683 | CDBox | 132 |
| HBII-85-18_x | 0.4 | 0.019329528 | 0.661 | CDBox | 48 |
| U106 | 0.3 | 0.019924806 | 0.653 | CDBox | 112 |
| U99 | 0.3 | 0.01993828 | 0.674 | HAcaBox | 137 |
| U24 | 0.3 | 0.020062119 | 0.673 | CDBox | 133 |

TABLE 5-continued miRNAs significantly expressed between metastatic melanoma and melanoma

| Probe Name | Log2-FC | P value | AUC | ProbeType | #Sample Detected |
|---|---|---|---|---|---|
| miR-20a-star | 1.0 | 0.020518991 | 0.694 | miRNA | 61 |
| U16 | 0.4 | 0.0213066 | 0.669 | CDBox | 131 |
| U49B_s | 0.5 | 0.0213349 | 0.716 | CDBox | 129 |
| miR-885-3p | 0.7 | 0.021367498 | 0.694 | miRNA | 73 |
| U36B | 0.4 | 0.021413004 | 0.669 | CDBox | 121 |
| HBII-295 | 0.3 | 0.021589703 | 0.678 | CDBox | 128 |
| miR-148b | 0.6 | 0.021711762 | 0.661 | miRNA | 32 |
| U38B | 0.7 | 0.022451358 | 0.834 | CDBox | 134 |
| U31 | 0.6 | 0.023045818 | 0.738 | CDBox | 132 |
| ACA8_x | 0.4 | 0.023508719 | 0.697 | HAcaBox | 125 |
| HBI-6_x | 0.5 | 0.02438732 | 0.675 | HAcaBox | 115 |
| mgU6-53B | 0.3 | 0.024830223 | 0.687 | CDBox | 99 |
| ACA62 | 0.4 | 0.024948935 | 0.714 | HAcaBox | 88 |
| miR-23b | -0.5 | 0.025010006 | 0.658 | miRNA | 137 |
| mgh18S-121 | 0.4 | 0.02717981 | 0.773 | CDBox | 134 |
| miR-134 | -0.6 | 0.027498011 | 0.648 | miRNA | 61 |
| ENSG00000202216 | -0.3 | 0.02787169 | 0.654 | snoRNA | 53 |
| snR38A | 0.5 | 0.028058616 | 0.706 | CDBox | 130 |
| ACA54 | 0.4 | 0.028079033 | 0.741 | HAcaBox | 133 |
| U83 | 0.4 | 0.028849489 | 0.733 | CDBox | 135 |
| U56_x | 0.5 | 0.03056515 | 0.673 | CDBox | 134 |
| ENSG00000207118 | 0.5 | 0.030731527 | 0.642 | snoRNA | 93 |
| U71b_x | 0.3 | 0.031331331 | 0.639 | HAcaBox | 117 |
| U104 | 0.5 | 0.031533136 | 0.750 | CDBox | 135 |
| miR-26b | 0.6 | 0.031546885 | 0.666 | miRNA | 45 |
| ENSG00000201129 | 0.4 | 0.031647545 | 0.658 | snoRNA | 54 |
| HBII-180C_x | 0.3 | 0.031765824 | 0.686 | CDBox | 131 |
| miR-1257 | -0.4 | 0.032490122 | 0.676 | miRNA | 31 |
| miR-1285 | 0.6 | 0.032817723 | 0.656 | miRNA | 54 |
| ACA6 | 0.4 | 0.033332825 | 0.706 | HAcaBox | 126 |
| HBII-166 | 0.3 | 0.033479679 | 0.715 | CDBox | 134 |
| U20 | 0.3 | 0.033581135 | 0.659 | CDBox | 117 |
| U49A_x | 0.5 | 0.034235707 | 0.734 | CDBox | 135 |
| HBII-85-11 | 0.5 | 0.034401945 | 0.626 | CDBox | 31 |
| miR-198 | 0.5 | 0.035071443 | 0.673 | miRNA | 31 |
| miR-1273 | 0.4 | 0.035126423 | 0.649 | miRNA | 47 |
| U8_x | 0.4 | 0.035369399 | 0.661 | CDBox | 135 |
| miR-127-3p | -0.5 | 0.035478749 | 0.646 | miRNA | 89 |
| U36C | 0.3 | 0.036400622 | 0.690 | CDBox | 135 |
| miR-502-3p | -0.5 | 0.036440109 | 0.696 | miRNA | 110 |
| U97 | 0.4 | 0.036556318 | 0.713 | CDBox | 133 |
| HBII-13 | 0.5 | 0.038037592 | 0.639 | CDBox | 52 |
| miR-148a | 0.6 | 0.038972124 | 0.647 | miRNA | 41 |
| hsa-let-7b | -0.7 | 0.040092161 | 0.713 | miRNA | 136 |
| U55 | 0.3 | 0.041929175 | 0.687 | CDBox | 135 |
| HBII-85-5_x | 0.3 | 0.04234391 | 0.645 | CDBox | 31 |
| U105 | 0.3 | 0.043199784 | 0.658 | CDBox | 126 |
| U90 | 0.3 | 0.043617609 | 0.701 | scaRna | 114 |
| ENSG00000202252 | 0.3 | 0.044418964 | 0.647 | snoRNA | 135 |
| ENSG00000201467_x | -0.3 | 0.04502792 | 0.628 | snoRNA | 31 |
| ACA21 | 0.5 | 0.045481211 | 0.754 | HAcaBox | 133 |
| U52 | 0.4 | 0.045645643 | 0.708 | CDBox | 135 |
| U18C_x | 0.4 | 0.046127928 | 0.637 | CDBox | 74 |
| HBII-296B | 0.3 | 0.046365102 | 0.657 | CDBox | 98 |
| ENSG00000200307 | 0.3 | 0.048211492 | 0.613 | snoRNA | 86 |
| miR-509-3p | -1.2 | 0.048257749 | 0.574 | miRNA | 116 |
| miR-1202 | 0.5 | 0.048318042 | 0.661 | miRNA | 57 |
| ACA36_x | 0.4 | 0.048990385 | 0.670 | HAcaBox | 88 |
| ENSG00000207016_x | 0.3 | 0.049618219 | 0.660 | snoRNA | 48 |
| miR-30c | 0.3 | 0.049698 | 0.709 | miRNA | 125 |
| ACA19 | 0.3 | 0.049825075 | 0.655 | HAcaBox | 118 |

TABLE 6

50 miRNAs most significantly expressed between metastatic melanoma and melanoma

| Probe Name | Log2-FC | P value | AUC | ProbeType | #Sample Detected |
|---|---|---|---|---|---|
| miR-31 | -2.4 | 6.23649E-09 | 0.891 | miRNA | 103 |
| miR-150 | -1.2 | 4.84574E-06 | 0.783 | miRNA | 117 |

TABLE 6-continued 50 miRNAs most significantly expressed between metastatic melanoma and melanoma

| Probe Name | Log2-FC | P value | AUC | ProbeType | #Sample Detected |
|---|---|---|---|---|---|
| miR-203 | −2.0 | 2.77555E−05 | 0.764 | miRNA | 132 |
| ENSG00000212139_x | 0.6 | 2.83257E−05 | 0.799 | snoRNA | 124 |
| mgU6-53 | 0.6 | 3.8628E−05 | 0.828 | CDBox | 94 |
| U72_x | 0.5 | 4.47709E−05 | 0.783 | HAcaBox | 103 |
| U94 | 0.6 | 7.34024E−05 | 0.776 | CDBox | 109 |
| HBII-85-15_x | 0.8 | 0.000176472 | 0.767 | CDBox | 49 |
| HBII-85-29_x | 0.8 | 0.000274959 | 0.734 | CDBox | 85 |
| HBII-55 | 0.5 | 0.000331716 | 0.806 | CDBox | 135 |
| snR38B | 0.8 | 0.000374886 | 0.750 | CDBox | 126 |
| miR-200c | −1.6 | 0.00042063 | 0.718 | miRNA | 134 |
| U61 | 0.7 | 0.000440758 | 0.785 | CDBox | 116 |
| HBII-316 | 0.6 | 0.000548042 | 0.744 | CDBox | 130 |
| U32A_x | 0.4 | 0.000553879 | 0.748 | CDBox | 136 |
| U81_x | 0.6 | 0.000598062 | 0.720 | CDBox | 120 |
| U15A | 0.7 | 0.000649777 | 0.785 | CDBox | 128 |
| ACA14b_x | 0.4 | 0.000764147 | 0.748 | HAcaBox | 105 |
| miR-182 | −0.9 | 0.000868427 | 0.762 | miRNA | 113 |
| miR-455-3p | −0.7 | 0.000874654 | 0.718 | miRNA | 136 |
| miR-532-5p | −0.8 | 0.000883675 | 0.752 | miRNA | 113 |
| mgU6-53_x | 0.5 | 0.001038416 | 0.783 | CDBox | 113 |
| ACA46 | 0.4 | 0.001076758 | 0.746 | HAcaBox | 124 |
| miR-1234 | −0.5 | 0.001112272 | 0.756 | miRNA | 68 |
| U53 | 0.6 | 0.001130502 | 0.769 | CDBox | 126 |
| HBII-85-29 | 0.7 | 0.001192467 | 0.702 | CDBox | 82 |
| U47 | 0.5 | 0.001218674 | 0.702 | CDBox | 74 |
| U42B_x | 0.5 | 0.001412559 | 0.735 | CDBox | 109 |
| miR-155 | −1.3 | 0.001425842 | 0.716 | miRNA | 123 |
| U64 | 0.5 | 0.001493551 | 0.728 | HAcaBox | 101 |
| ACA28 | 0.5 | 0.001565276 | 0.692 | HAcaBox | 120 |
| U13 | 0.6 | 0.001630341 | 0.748 | CDBox | 135 |
| U84 | 0.4 | 0.001673776 | 0.769 | CDBox | 131 |
| U22 | 0.5 | 0.001739769 | 0.714 | CDBox | 135 |
| U46_x | 0.6 | 0.001758635 | 0.755 | CDBox | 131 |
| ACA17_x | 0.6 | 0.001827243 | 0.705 | HAcaBox | 44 |
| ENSG00000200897 | 0.4 | 0.001857043 | 0.735 | snoRNA | 38 |
| U36A_x | 0.4 | 0.00192703 | 0.728 | CDBox | 133 |
| HBII-180C | 0.4 | 0.001987135 | 0.757 | CDBox | 115 |
| HBII-251 | 0.4 | 0.0020213 | 0.741 | CDBox | 135 |
| ACA49 | 0.4 | 0.002175278 | 0.744 | HAcaBox | 127 |
| U19 | 0.6 | 0.00221226 | 0.696 | HAcaBox | 118 |
| miR-940 | −0.6 | 0.002377881 | 0.713 | miRNA | 53 |
| U76 | 0.6 | 0.002408733 | 0.755 | CDBox | 135 |
| HBII-13_x | 0.7 | 0.002521867 | 0.730 | CDBox | 60 |
| HBII-382_s | 0.6 | 0.002554678 | 0.770 | scaRna | 126 |
| miR-205 | −1.1 | 0.002610442 | 0.603 | miRNA | 135 |
| U21 | 0.7 | 0.002613305 | 0.774 | CDBox | 134 |
| miR-342-3p | −0.5 | 0.002621512 | 0.706 | miRNA | 136 |
| ENSG00000212326 | 0.5 | 0.002879558 | 0.728 | snoRNA | 104 |

TABLE 7 miRNAs significantly expressed between nevi and normal skin

| Probe Name | Log2-FC | P value | AUC | ProbeType | #Sample Detected |
|---|---|---|---|---|---|
| 14qII-14 | −3.87 | 3.6592E−27 | 1.000 | CDBox | 56 |
| 14qII-14_x | −3.21 | 3.815E−24 | 1.000 | CDBox | 56 |
| U74_x | 1.46 | 3.89068E−23 | 1.000 | CDBox | 135 |
| miR-509-3p | 5.78 | 1.67661E−22 | 0.997 | miRNA | 116 |
| miR-768-5p | −1.46 | 5.23441E−22 | 1.000 | miRNA | 135 |
| ENSG00000199411_s | 1.36 | 1.56796E−21 | 1.000 | snoRNA | 135 |
| Z17B | −1.94 | 2.89347E−20 | 0.997 | CDBox | 117 |
| miR-149 | −3.46 | 1.55425E−19 | 1.000 | miRNA | 100 |
| miR-125a-5p | −3.44 | 1.86526E−19 | 1.000 | miRNA | 128 |
| U43 | −1.19 | 3.32514E−19 | 1.000 | CDBox | 135 |
| miR-1308 | 1.55 | 8.1184E−19 | 0.964 | miRNA | 135 |
| U59A | 1.13 | 9.99768E−18 | 0.993 | CDBox | 135 |
| miR-146a | 4.44 | 3.16232E−17 | 0.975 | miRNA | 129 |
| miR-513a-5p | 3.77 | 1.05679E−16 | 0.972 | miRNA | 105 |
| ACA20 | −1.74 | 1.56297E−16 | 0.993 | HAcaBox | 131 |

TABLE 7-continued miRNAs significantly expressed between nevi and normal skin

| Probe Name | Log2-FC | P value | AUC | ProbeType | #Sample Detected |
|---|---|---|---|---|---|
| U43_x | −1.05 | 1.04459E−15 | 1.000 | CDBox | 135 |
| U44_x | −1.37 | 5.54123E−15 | 0.994 | CDBox | 135 |
| miR-127-3p | −3.56 | 7.53549E−15 | 0.988 | miRNA | 89 |
| miR-193b | −2.57 | 7.81928E−15 | 1.000 | miRNA | 130 |
| U83 | −1.25 | 9.30493E−15 | 0.993 | CDBox | 135 |
| miR-768-3p | 0.98 | 2.39925E−14 | 0.972 | miRNA | 137 |
| U33 | −1.02 | 2.44194E−14 | 0.997 | CDBox | 137 |
| miR-574-3p | −3.05 | 3.0433E−14 | 0.974 | miRNA | 122 |
| ACA16 | −1.86 | 3.35128E−14 | 0.968 | HAcaBox | 47 |
| 14qI-4 | −2.43 | 3.96317E−14 | 0.979 | CDBox | 80 |
| hsa-let-7c | −1.01 | 4.99111E−14 | 0.986 | miRNA | 135 |
| miR-342-3p | −2.06 | 1.67074E−13 | 0.996 | miRNA | 136 |
| hsa-let-7b | −1.01 | 2.25904E−13 | 0.964 | miRNA | 136 |
| miR-423-3p | −2.52 | 2.97967E−13 | 1.000 | miRNA | 107 |
| HBII-239 | −1.41 | 3.2162E−13 | 0.975 | CDBox | 135 |
| U38B_x | 1.52 | 3.80613E−13 | 0.968 | CDBox | 133 |
| miR-320b | −0.63 | 6.31909E−13 | 0.971 | miRNA | 135 |
| miR-923 | 0.93 | 6.48332E−13 | 0.990 | miRNA | 135 |
| U54 | −1.06 | 1.17197E−12 | 0.975 | CDBox | 135 |
| U38B | 1.80 | 1.18885E−12 | 0.976 | CDBox | 134 |
| U44 | −1.07 | 1.28887E−12 | 0.981 | CDBox | 134 |
| miR-139-5p | −2.70 | 2.74261E−12 | 0.940 | miRNA | 80 |
| miR-1826 | −0.71 | 2.83317E−12 | 0.958 | miRNA | 137 |
| ENSG00000199435 | 1.38 | 2.88249E−12 | 0.954 | snoRNA | 63 |
| miR-26a | 0.89 | 2.88328E−12 | 0.960 | miRNA | 136 |
| U58B_x | −1.47 | 3.60008E−12 | 0.940 | CDBox | 132 |
| HBII-180A_x | −1.43 | 4.25614E−12 | 0.992 | CDBox | 123 |
| 14qII-12_x | −2.09 | 4.30741E−12 | 0.949 | CDBox | 85 |
| miR-509-3-5p | 3.46 | 5.53398E−12 | 0.953 | miRNA | 107 |
| U55_x | −1.35 | 6.7836E−12 | 0.996 | CDBox | 135 |
| miR-149-star | 0.93 | 9.6022E−12 | 0.940 | miRNA | 135 |
| HBII-276 | −1.41 | 1.19464E−11 | 0.964 | CDBox | 132 |
| miR-23b | −0.75 | 1.72105E−11 | 0.968 | miRNA | 137 |
| miR-15b | −2.42 | 1.7823E−11 | 0.968 | miRNA | 125 |
| miR-921 | 1.73 | 1.93285E−11 | 0.954 | miRNA | 49 |
| miR-191 | −0.85 | 2.0881E−11 | 0.972 | miRNA | 135 |
| U103_s | −1.60 | 2.57483E−11 | 0.943 | CDBox | 111 |
| miR-486-5p | −3.27 | 2.90873E−11 | 0.942 | miRNA | 65 |
| U27 | −1.61 | 3.28995E−11 | 0.960 | CDBox | 134 |
| miR-1202 | 2.18 | 4.44562E−11 | 0.945 | miRNA | 57 |
| U49A | 1.25 | 4.51441E−11 | 0.970 | CDBox | 135 |
| ACA24_x | −1.50 | 5.61856E−11 | 0.922 | HAcaBox | 98 |
| HBII-382_s | 1.30 | 5.89071E−11 | 0.953 | scaRna | 126 |
| U52 | −0.92 | 1.05668E−10 | 0.976 | CDBox | 135 |
| miR-99b | −1.84 | 1.06853E−10 | 0.988 | miRNA | 129 |
| U38A | 0.84 | 1.30902E−10 | 0.936 | CDBox | 134 |
| U46 | −1.44 | 1.33613E−10 | 0.965 | CDBox | 133 |
| U57 | −1.10 | 1.66897E−10 | 0.967 | CDBox | 135 |
| U3-2_s | 0.70 | 1.79537E−10 | 0.925 | CDBox | 135 |
| 14qII-26_x | −1.60 | 1.92804E−10 | 0.922 | CDBox | 41 |
| ENSG00000207098_x | 1.21 | 2.17044E−10 | 0.956 | snoRNA | 86 |
| miR-320c | −0.84 | 2.33286E−10 | 0.994 | miRNA | 135 |
| miR-199a-5p | −2.53 | 2.85196E−10 | 0.994 | miRNA | 129 |
| HBII-180C | −1.55 | 3.80017E−10 | 0.924 | CDBox | 115 |
| U63 | 0.94 | 4.46838E−10 | 0.945 | CDBox | 135 |
| HBII-436 | −1.22 | 4.98357E−10 | 0.929 | CDBox | 102 |
| U81_x | −1.25 | 6.27975E−10 | 0.928 | CDBox | 120 |
| HBII-419 | 1.10 | 6.92884E−10 | 0.932 | CDBox | 133 |
| U17b | −1.32 | 8.76094E−10 | 0.996 | HAcaBox | 135 |
| miR-506 | 2.11 | 1.46252E−09 | 0.931 | miRNA | 76 |
| miR-1268 | 1.02 | 1.54826E−09 | 0.909 | miRNA | 133 |
| miR-671-5p | 1.38 | 1.60795E−09 | 0.914 | miRNA | 69 |
| miR-339-5p | −2.03 | 1.92249E−09 | 0.907 | miRNA | 75 |
| ACA48_x | −1.25 | 1.98889E−09 | 0.945 | HAcaBox | 130 |
| 14qII-21_x | −1.20 | 2.04198E−09 | 0.907 | CDBox | 51 |
| ENSG00000202093_x | −1.37 | 2.13676E−09 | 0.902 | snoRNA | 125 |
| U73a | −0.76 | 3.11274E−09 | 0.924 | CDBox | 135 |
| miR-1228-star | 1.09 | 3.32612E−09 | 0.925 | miRNA | 134 |
| miR-193b-star | −1.99 | 3.54373E−09 | 0.925 | miRNA | 77 |
| miR-145 | −2.87 | 3.67076E−09 | 0.986 | miRNA | 135 |
| miR-1207-5p | 0.91 | 3.82606E−09 | 0.936 | miRNA | 133 |
| miR-23a | −0.62 | 4.38608E−09 | 0.950 | miRNA | 137 |
| 14qII-3 | −1.37 | 5.04275E−09 | 0.938 | CDBox | 95 |
| U56 | 0.82 | 5.34057E−09 | 0.910 | CDBox | 135 |
| miR-320a | −0.50 | 5.87182E−09 | 0.917 | miRNA | 135 |

TABLE 7-continued miRNAs significantly expressed between nevi and normal skin

| Probe Name | Log2-FC | P value | AUC | ProbeType | #Sample Detected |
|---|---|---|---|---|---|
| HBII-289 | −0.82 | 6.53343E−09 | 0.975 | CDBox | 135 |
| mgU6-53B | 1.17 | 6.66322E−09 | 0.946 | CDBox | 99 |
| miR-222 | −1.42 | 6.66965E−09 | 1.000 | miRNA | 135 |
| miR-135a-star | 1.78 | 6.83122E−09 | 0.914 | miRNA | 44 |
| HBII-142 | 0.50 | 6.91032E−09 | 0.911 | CDBox | 135 |
| 14qII-12 | −1.90 | 7.3584E−09 | 0.896 | CDBox | 58 |
| ACA23 | −1.07 | 9.00722E−09 | 0.922 | HAcaBox | 113 |
| miR-1224-5p | 2.00 | 9.14764E−09 | 0.902 | miRNA | 78 |
| U17b_x | −0.78 | 9.16941E−09 | 0.917 | HAcaBox | 135 |
| U41 | −0.89 | 1.0052E−08 | 0.928 | CDBox | 135 |
| U55 | −1.40 | 1.07645E−08 | 0.988 | CDBox | 135 |
| U101 | 1.01 | 1.22325E−08 | 0.911 | CDBox | 134 |
| miR-193a-5p | −2.09 | 1.43928E−08 | 0.954 | miRNA | 121 |
| miR-720 | 0.87 | 1.45059E−08 | 0.918 | miRNA | 137 |
| miR-205 | −1.04 | 1.53388E−08 | 0.956 | miRNA | 135 |
| mgh28S-2411 | −0.86 | 1.81685E−08 | 0.965 | CDBox | 135 |
| miR-1300 | 1.84 | 1.83075E−08 | 0.911 | miRNA | 32 |
| miR-22 | −2.31 | 1.87992E−08 | 0.943 | miRNA | 120 |
| ACA40_x | −1.14 | 1.89306E−08 | 0.935 | HAcaBox | 134 |
| miR-92a | −1.48 | 1.96388E−08 | 1.000 | miRNA | 136 |
| 14qII-28_x | −1.20 | 2.08991E−08 | 0.911 | CDBox | 51 |
| U23 | −0.93 | 2.35134E−08 | 0.913 | HAcaBox | 127 |
| snR38C | 0.62 | 2.69211E−08 | 0.902 | CDBox | 134 |
| miR-939 | 1.33 | 2.8172E−08 | 0.947 | miRNA | 57 |
| miR-214 | −0.88 | 2.85157E−08 | 0.921 | miRNA | 135 |
| U94 | 1.03 | 3.14773E−08 | 0.898 | CDBox | 109 |
| miR-510 | 2.20 | 3.61106E−08 | 0.899 | miRNA | 82 |
| miR-181b | −1.85 | 5.28195E−08 | 0.961 | miRNA | 130 |
| U15B | −1.06 | 5.57521E−08 | 0.898 | CDBox | 129 |
| gi555853_copy5 | −0.51 | 7.13438E−08 | 0.910 | 5.8s rRNA | 137 |
| miR-432 | −1.83 | 7.49361E−08 | 0.902 | miRNA | 51 |
| HBII-142_x | 0.47 | 8.53374E−08 | 0.886 | CDBox | 135 |
| snR38B | 1.11 | 8.92959E−08 | 0.899 | CDBox | 126 |
| ACA36_x | 1.12 | 9.60154E−08 | 0.885 | HAcaBox | 88 |
| miR-320d | −1.66 | 1.03365E−07 | 0.997 | miRNA | 134 |
| hsa-let-7i | 1.72 | 1.07923E−07 | 0.947 | miRNA | 135 |
| miR-125b-2-star | −1.66 | 1.09644E−07 | 0.881 | miRNA | 58 |
| miR-572 | 1.35 | 1.13617E−07 | 0.906 | miRNA | 116 |
| U102 | 0.87 | 1.2385E−07 | 0.874 | CDBox | 124 |
| gi555853_copy8 | −0.51 | 1.25699E−07 | 0.903 | 5.8s rRNA | 137 |
| miR-371-5p | 1.93 | 1.26302E−07 | 0.886 | miRNA | 64 |
| miR-125b | −0.97 | 1.35947E−07 | 0.988 | miRNA | 135 |
| ENSG00000201619 | 1.40 | 1.4629E−07 | 0.892 | snoRNA | 62 |
| U78_x | 1.11 | 1.62568E−07 | 0.921 | CDBox | 134 |
| ENSG00000212397 | 0.90 | 1.65415E−07 | 0.898 | snoRNA | 134 |
| ENSG00000212182 | 1.09 | 1.80486E−07 | 0.884 | snoRNA | 59 |
| hsa-let-7f | 1.99 | 2.0615E−07 | 0.909 | miRNA | 130 |
| HBII-55 | −0.82 | 2.17315E−07 | 0.940 | CDBox | 135 |
| gi555853_copy2 | −0.49 | 2.37022E−07 | 0.893 | 5.8s rRNA | 137 |
| ACA15_s | −1.09 | 2.48572E−07 | 0.875 | HAcaBox | 116 |
| U28_x | −0.90 | 2.5645E−07 | 0.896 | CDBox | 133 |
| gi555853_copy0 | −0.50 | 2.65495E−07 | 0.889 | 5.8s rRNA | 137 |
| gi555853_copy4 | −0.48 | 2.85254E−07 | 0.898 | 5.8s rRNA | 137 |
| ENSG00000201816 | 0.83 | 3.19058E−07 | 0.878 | snoRNA | 49 |
| gi555853_copy1 | −0.48 | 3.26181E−07 | 0.886 | 5.8s rRNA | 137 |
| U60 | −0.97 | 3.26261E−07 | 0.871 | CDBox | 103 |
| gi555853_copy6 | −0.47 | 3.40126E−07 | 0.900 | 5.8s rRNA | 137 |
| miR-132 | −1.77 | 3.42625E−07 | 0.870 | miRNA | 96 |
| U68_x | −1.05 | 3.51611E−07 | 0.910 | HAcaBox | 133 |
| gi555853_copy7 | −0.48 | 4.04469E−07 | 0.892 | 5.8s rRNA | 137 |
| ENSG00000201660 | 1.12 | 4.27296E−07 | 0.896 | snoRNA | 132 |
| miR-150-star | 1.63 | 4.51511E−07 | 0.874 | miRNA | 48 |
| miR-665 | 1.55 | 5.14634E−07 | 0.871 | miRNA | 47 |
| miR-150 | −1.60 | 6.5278E−07 | 0.884 | miRNA | 117 |
| miR-210 | −1.24 | 6.58793E−07 | 0.911 | miRNA | 130 |
| miR-664-star | 1.38 | 6.79224E−07 | 0.864 | miRNA | 96 |
| U49A_x | 1.03 | 7.09035E−07 | 0.911 | CDBox | 135 |
| miR-30c | −1.75 | 7.10279E−07 | 0.911 | miRNA | 125 |
| ENSG00000212458 | 0.92 | 7.71477E−07 | 0.871 | snoRNA | 95 |
| ENSG00000200879 | −1.08 | 7.74449E−07 | 0.868 | snoRNA | 120 |
| hsa-let-7d | 0.39 | 8.11829E−07 | 0.886 | miRNA | 135 |
| 14qII-1_x | −1.24 | 9.36723E−07 | 0.899 | CDBox | 131 |
| 14qII-26 | −1.14 | 1.46915E−06 | 0.827 | CDBox | 32 |
| hsa-let-7a | 0.51 | 1.65358E−06 | 0.841 | miRNA | 136 |
| U28 | −0.75 | 1.71566E−06 | 0.874 | CDBox | 135 |

TABLE 7-continued miRNAs significantly expressed between nevi and normal skin

| Probe Name | Log2-FC | P value | AUC | ProbeType | #Sample Detected |
|---|---|---|---|---|---|
| U68 | −0.88 | 1.83186E−06 | 0.892 | HAcaBox | 130 |
| HBII-180C_x | −0.95 | 2.06263E−06 | 0.882 | CDBox | 131 |
| gi555853_copy3 | −0.45 | 2.14632E−06 | 0.863 | 5.8s rRNA | 137 |
| miR-200b-star | −1.70 | 2.20935E−06 | 0.861 | miRNA | 74 |
| miR-1234 | 1.03 | 2.2168E−06 | 0.861 | miRNA | 68 |
| U95 | −0.36 | 2.37891E−06 | 0.852 | CDBox | 135 |
| U46_x | −0.98 | 2.42909E−06 | 0.873 | CDBox | 131 |
| spike_in-control-21 | 0.74 | 2.57369E−06 | 0.827 | Oligonucleotide spike-in controls | 42 |
| miR-1248 | 1.03 | 3.51695E−06 | 0.874 | miRNA | 39 |
| U36A | −0.61 | 3.61256E−06 | 0.882 | CDBox | 132 |
| U13 | 0.50 | 4.36581E−06 | 0.834 | CDBox | 135 |
| miR-92a-2-star | 1.02 | 4.99387E−06 | 0.859 | miRNA | 46 |
| miR-663 | 0.77 | 5.24563E−06 | 0.859 | miRNA | 134 |
| miR-409-3p | −1.42 | 5.63777E−06 | 0.837 | miRNA | 92 |
| U34 | −0.68 | 5.88695E−06 | 0.852 | CDBox | 137 |
| U25 | −0.71 | 6.25404E−06 | 0.896 | CDBox | 135 |
| U32A_x | −0.75 | 6.51615E−06 | 0.882 | CDBox | 136 |
| U96a_x | 0.68 | 6.70342E−06 | 0.849 | CDBox | 134 |
| gi555853_copy9 | −0.42 | 7.0704E−06 | 0.863 | 5.8s rRNA | 137 |
| ENSG00000199411_x | 0.77 | 7.82781E−06 | 0.846 | snoRNA | 132 |
| spike_in-control-7 | 1.00 | 7.92241E−06 | 0.848 | Oligonucleotide spike-in controls | 54 |
| miR-198 | 1.24 | 8.11341E−06 | 0.846 | miRNA | 31 |
| 14qI-9_x | −0.81 | 8.29164E−06 | 0.820 | CDBox | 34 |
| miR-425 | −1.72 | 8.48515E−06 | 0.846 | miRNA | 114 |
| HBII-82 | 0.77 | 8.59528E−06 | 0.839 | CDBox | 90 |
| miR-1180 | −1.22 | 9.75327E−06 | 0.828 | miRNA | 37 |
| ENSG00000206637_x | 0.74 | 1.15035E−05 | 0.850 | snoRNA | 59 |
| miR-502-3p | −1.41 | 1.18784E−05 | 0.831 | miRNA | 110 |
| 14qII-22_x | −0.97 | 1.49319E−05 | 0.792 | CDBox | 50 |
| ACA18_x | −0.72 | 1.77602E−05 | 0.837 | HAcaBox | 135 |
| miR-1274b | 1.66 | 1.82625E−05 | 0.813 | miRNA | 112 |
| HBII-99 | −0.94 | 1.84996E−05 | 0.837 | CDBox | 122 |
| U35B | 0.78 | 1.93006E−05 | 0.837 | CDBox | 128 |
| ACA20_x | −0.84 | 2.02452E−05 | 0.882 | HAcaBox | 134 |
| miR-143 | −2.21 | 2.0661E−05 | 0.864 | miRNA | 126 |
| ENSG00000200652 | 0.81 | 2.09666E−05 | 0.824 | snoRNA | 40 |
| HBII-202 | −0.59 | 2.32067E−05 | 0.886 | CDBox | 135 |
| miR-708 | −1.81 | 2.34758E−05 | 0.816 | miRNA | 102 |
| miR-182 | −1.64 | 2.56273E−05 | 0.791 | miRNA | 113 |
| miR-345 | −1.28 | 3.1705E−05 | 0.816 | miRNA | 75 |
| ACA62 | 0.82 | 3.35475E−05 | 0.817 | HAcaBox | 88 |
| miR-1273 | 1.12 | 3.38999E−05 | 0.827 | miRNA | 47 |
| ACA24_s | −1.10 | 3.44078E−05 | 0.823 | HAcaBox | 128 |
| miR-1272 | 0.97 | 3.51756E−05 | 0.820 | miRNA | 67 |
| 14qI-4_x | −1.11 | 3.64993E−05 | 0.796 | CDBox | 51 |
| 14qII-9_x | −0.89 | 3.72476E−05 | 0.820 | CDBox | 36 |
| U106 | −0.62 | 3.79813E−05 | 0.817 | CDBox | 112 |
| miR-1285 | 1.22 | 4.16925E−05 | 0.796 | miRNA | 54 |
| ENSG00000200492 | 0.77 | 4.61258E−05 | 0.838 | snoRNA | 60 |
| ENSG00000202327 | 0.77 | 4.61736E−05 | 0.812 | snoRNA | 54 |
| miR-126 | 1.24 | 4.86215E−05 | 0.845 | miRNA | 133 |
| U49B_x | 0.62 | 4.92521E−05 | 0.795 | CDBox | 122 |
| ENSG00000207016_x | 0.74 | 5.4547E−05 | 0.794 | snoRNA | 48 |
| HBII-52-25_x | 0.68 | 5.50793E−05 | 0.827 | CDBox | 57 |
| U49B_s | 0.90 | 5.94839E−05 | 0.848 | CDBox | 129 |
| U53 | −0.97 | 6.07982E−05 | 0.809 | CDBox | 126 |
| miR-1246 | 1.19 | 7.10577E−05 | 0.799 | miRNA | 131 |
| ENSG00000212615_x | −0.67 | 7.76933E−05 | 0.798 | snoRNA | 102 |
| miR-575 | 1.09 | 8.31223E−05 | 0.794 | miRNA | 41 |
| snR38A | 0.69 | 8.40239E−05 | 0.807 | CDBox | 130 |
| 14qI-7 | −0.78 | 8.70579E−05 | 0.825 | CDBox | 51 |
| miR-29b-2-star | 0.86 | 8.9139E−05 | 0.802 | miRNA | 126 |
| U80 | −0.60 | 9.75089E−05 | 0.825 | CDBox | 132 |
| miR-1225-5p | 1.04 | 9.99249E−05 | 0.830 | miRNA | 90 |
| miR-92b-star | 0.94 | 0.000102055 | 0.809 | miRNA | 111 |
| ACA53 | −0.61 | 0.000103826 | 0.814 | HAcaBox | 105 |
| ACA55 | 0.79 | 0.000105025 | 0.805 | HAcaBox | 85 |
| U51 | 0.58 | 0.000112048 | 0.802 | CDBox | 134 |
| U108_x | 0.55 | 0.000112181 | 0.798 | HAcaBox | 87 |
| U48 | −1.07 | 0.000118819 | 0.875 | CDBox | 129 |
| miR-221 | −1.06 | 0.00013613 | 0.911 | miRNA | 135 |

TABLE 7-continued miRNAs significantly expressed between nevi and normal skin

| Probe Name | Log2-FC | P value | AUC | ProbeType | #Sample Detected |
|---|---|---|---|---|---|
| HBII-13 | 0.74 | 0.000139215 | 0.798 | CDBox | 52 |
| miR-19b | 1.53 | 0.0001409 | 0.795 | miRNA | 124 |
| ACA3-2 | −0.76 | 0.000143105 | 0.819 | HAcaBox | 135 |
| HBII-85-23_x | −0.73 | 0.000143482 | 0.787 | CDBox | 58 |
| 14qI-8 | −0.75 | 0.000167587 | 0.802 | CDBox | 61 |
| miR-138-1-star | 0.88 | 0.000190948 | 0.798 | miRNA | 91 |
| spike_in-control-28 | 0.63 | 0.000200982 | 0.802 | Oligonucleotide spike-in controls | 76 |
| miR-500-star | −1.36 | 0.000204792 | 0.803 | miRNA | 97 |
| ENSG00000212423_x | 0.75 | 0.000232739 | 0.789 | snoRNA | 115 |
| ENSG00000201348 | 0.50 | 0.000243216 | 0.778 | snoRNA | 94 |
| miR-1275 | 1.09 | 0.000244874 | 0.821 | miRNA | 127 |
| miR-30a-star | −1.14 | 0.000247652 | 0.758 | miRNA | 64 |
| miR-93-star | −1.16 | 0.000248272 | 0.777 | miRNA | 48 |
| ACA25 | −0.64 | 0.000248534 | 0.802 | HAcaBox | 73 |
| U50 | −0.73 | 0.000255129 | 0.853 | CDBox | 134 |
| 14qII-1 | −1.00 | 0.000255606 | 0.807 | CDBox | 128 |
| U14B_x | −0.79 | 0.000258746 | 0.788 | CDBox | 53 |
| miR-638 | 0.35 | 0.000261809 | 0.823 | miRNA | 135 |
| U51_x | 0.57 | 0.000299812 | 0.820 | CDBox | 130 |
| miR-99a | −0.87 | 0.000321188 | 0.832 | miRNA | 135 |
| miR-491-5p | 1.04 | 0.000341416 | 0.756 | miRNA | 92 |
| miR-508-3p | 1.23 | 0.000350578 | 0.778 | miRNA | 74 |
| miR-508-5p | 1.02 | 0.000377448 | 0.783 | miRNA | 92 |
| miR-641 | 0.88 | 0.000391728 | 0.774 | miRNA | 39 |
| miR-885-5p | −1.23 | 0.00039874 | 0.801 | miRNA | 100 |
| miR-497 | −1.48 | 0.00041742 | 0.780 | miRNA | 104 |
| U31_x | −0.65 | 0.000420569 | 0.795 | CDBox | 135 |
| miR-498 | 0.85 | 0.000424439 | 0.787 | miRNA | 56 |
| miR-20a | 1.21 | 0.000429079 | 0.807 | miRNA | 134 |
| miR-509-5p | 1.35 | 0.000476275 | 0.776 | miRNA | 81 |
| miR-331-3p | −1.11 | 0.000481237 | 0.777 | miRNA | 64 |
| HBII-295 | 0.53 | 0.000526137 | 0.785 | CDBox | 128 |
| ACA27_x | −0.45 | 0.000528795 | 0.778 | HAcaBox | 130 |
| miR-155 | −1.29 | 0.000530869 | 0.751 | miRNA | 123 |
| miR-652 | −1.30 | 0.000593692 | 0.774 | miRNA | 119 |
| ENSG00000208308_x | −0.58 | 0.000595144 | 0.758 | snoRNA | 129 |
| miR-1281 | 0.98 | 0.000606821 | 0.766 | miRNA | 137 |
| E3_x | −0.53 | 0.000619964 | 0.819 | HAcaBox | 135 |
| miR-27a-star | −0.88 | 0.000656179 | 0.773 | miRNA | 40 |
| miR-92b | −0.90 | 0.0006705 | 0.773 | miRNA | 91 |
| miR-570 | 0.93 | 0.000670846 | 0.776 | miRNA | 88 |
| miR-181a-2-star | −1.19 | 0.000676824 | 0.753 | miRNA | 99 |
| miR-1185 | 0.76 | 0.000680122 | 0.752 | miRNA | 42 |
| ACA33 | 0.57 | 0.000718022 | 0.780 | HAcaBox | 133 |
| ENSG00000212401 | 0.57 | 0.000773614 | 0.799 | snoRNA | 41 |
| U20 | −0.51 | 0.000816772 | 0.758 | CDBox | 117 |
| U19 | 0.84 | 0.00082895 | 0.759 | HAcaBox | 118 |
| miR-203 | 0.69 | 0.000839225 | 0.878 | miRNA | 132 |
| ENSG00000212508 | 0.83 | 0.000873066 | 0.801 | snoRNA | 122 |
| ACA54 | −0.54 | 0.000880465 | 0.817 | HAcaBox | 133 |
| ACA9_x | −0.68 | 0.001025389 | 0.752 | HAcaBox | 77 |
| 14qI-1 | 0.61 | 0.001136212 | 0.729 | CDBox | 70 |
| miR-940 | 0.87 | 0.001164857 | 0.737 | miRNA | 53 |
| U14B | −0.69 | 0.001178164 | 0.738 | CDBox | 51 |
| mgU6-77 | −0.62 | 0.001238112 | 0.760 | CDBox | 129 |
| spike_in-control-30 | 0.54 | 0.001290622 | 0.753 | Oligonucleotide spike-in controls | 53 |
| miR-629-star | −0.92 | 0.00138462 | 0.756 | miRNA | 46 |
| ACA49 | 0.56 | 0.001394857 | 0.791 | HAcaBox | 127 |
| miR-483-5p | 0.96 | 0.001461794 | 0.738 | miRNA | 48 |
| ENSG00000212214_x | 0.51 | 0.001505107 | 0.748 | snoRNA | 88 |
| miR-574-5p | −0.99 | 0.00156768 | 0.766 | miRNA | 103 |
| miR-28-3p | −1.29 | 0.001658961 | 0.747 | miRNA | 94 |
| U36C | 0.34 | 0.001694833 | 0.849 | CDBox | 135 |
| miR-1288 | 0.73 | 0.001697813 | 0.738 | miRNA | 43 |
| ACA37_x | −0.59 | 0.001721183 | 0.742 | HAcaBox | 84 |
| miR-1280 | −0.72 | 0.001869035 | 0.777 | miRNA | 134 |
| miR-487b | −0.96 | 0.001988497 | 0.731 | miRNA | 58 |
| miR-532-3p | −0.80 | 0.00199381 | 0.766 | miRNA | 95 |
| miR-346 | −0.91 | 0.0020172 | 0.749 | miRNA | 55 |
| miR-27b-star | −1.04 | 0.00209985 | 0.742 | miRNA | 51 |
| ACA32 | 0.34 | 0.002161552 | 0.785 | HAcaBox | 135 |

TABLE 7-continued miRNAs significantly expressed between nevi and normal skin

| Probe Name | Log2-FC | P value | AUC | ProbeType | #Sample Detected |
|---|---|---|---|---|---|
| ENSG00000212206_x | 0.58 | 0.002337296 | 0.740 | snoRNA | 74 |
| ACA51_x | 0.43 | 0.002449336 | 0.742 | HAcaBox | 135 |
| ENSG00000201847_x | −0.53 | 0.002461896 | 0.729 | snoRNA | 48 |
| miR-513c | 1.13 | 0.002510473 | 0.749 | miRNA | 73 |
| miR-455-3p | −0.62 | 0.00258213 | 0.785 | miRNA | 136 |
| miR-188-5p | −0.90 | 0.002825937 | 0.730 | miRNA | 51 |
| ENSG00000207027 | 0.48 | 0.002903474 | 0.704 | snoRNA | 36 |
| ENSG00000202498_x | 0.56 | 0.002908782 | 0.735 | snoRNA | 137 |
| HBII-85-26 | 0.66 | 0.003001767 | 0.741 | CDBox | 136 |
| miR-337-3p | 0.80 | 0.003015225 | 0.740 | miRNA | 94 |
| U35A | −0.47 | 0.003204612 | 0.723 | CDBox | 135 |
| miR-106b-star | −1.10 | 0.003210131 | 0.717 | miRNA | 72 |
| ENSG00000202216 | 0.55 | 0.003292357 | 0.758 | snoRNA | 53 |
| HBII-316 | 0.63 | 0.003333247 | 0.705 | CDBox | 130 |
| miR-31 | −1.63 | 0.003410838 | 0.720 | miRNA | 103 |
| U22 | 0.43 | 0.003510102 | 0.699 | CDBox | 135 |
| miR-34a-star | 0.77 | 0.003765001 | 0.715 | miRNA | 39 |
| HBII-85-6_x | 0.62 | 0.003870576 | 0.735 | CDBox | 137 |
| ACA15_x | −0.50 | 0.003952375 | 0.734 | HAcaBox | 124 |
| ENSG00000200706_x | 0.48 | 0.00407636 | 0.762 | snoRNA | 43 |
| ENSG00000212627 | 0.41 | 0.00409948 | 0.726 | snoRNA | 69 |
| 14qII-7 | 0.59 | 0.004220389 | 0.719 | CDBox | 77 |
| ENSG00000212432_s | 0.52 | 0.004352612 | 0.745 | snoRNA | 75 |
| miR-214-star | −0.82 | 0.004514439 | 0.708 | miRNA | 47 |
| miR-106a | 0.58 | 0.004682448 | 0.724 | miRNA | 135 |
| ACA42 | −0.54 | 0.004759271 | 0.720 | HAcaBox | 117 |
| mgU6-53B_x | 0.46 | 0.0048197 | 0.720 | CDBox | 121 |
| ACA19 | 0.38 | 0.005153495 | 0.733 | HAcaBox | 118 |
| ACA50 | −0.53 | 0.005300761 | 0.738 | HAcaBox | 88 |
| miR-138 | 1.07 | 0.005618175 | 0.716 | miRNA | 82 |
| U47 | −0.47 | 0.005755719 | 0.729 | CDBox | 74 |
| ENSG00000212551 | 0.48 | 0.005885716 | 0.740 | snoRNA | 73 |
| miR-769-5p | −0.93 | 0.005951319 | 0.687 | miRNA | 56 |
| miR-1228 | 0.82 | 0.006114287 | 0.724 | miRNA | 114 |
| miR-30b | 0.87 | 0.00634299 | 0.748 | miRNA | 128 |
| ENSG00000212315 | 0.54 | 0.006470787 | 0.752 | snoRNA | 117 |
| ENSG00000212538 | 0.48 | 0.006558925 | 0.735 | snoRNA | 35 |
| ACA2b | 0.39 | 0.007073038 | 0.756 | HAcaBox | 47 |
| ENSG00000212523_x | 0.59 | 0.007115341 | 0.716 | snoRNA | 135 |
| miR-196a | 1.04 | 0.007138032 | 0.705 | miRNA | 77 |
| HBII-429 | 0.22 | 0.007262326 | 0.720 | CDBox | 137 |
| miR-16 | 0.46 | 0.007360456 | 0.749 | miRNA | 135 |
| mgh28S-2409 | 0.27 | 0.007642791 | 0.741 | CDBox | 135 |
| ENSG00000200307_x | 0.54 | 0.007656242 | 0.695 | snoRNA | 50 |
| U76 | −0.27 | 0.008469646 | 0.734 | CDBox | 135 |
| 14qII-17 | −0.54 | 0.008809376 | 0.698 | CDBox | 71 |
| miR-324-3p | −0.67 | 0.009111464 | 0.726 | miRNA | 100 |
| ACA48 | −0.49 | 0.009193835 | 0.798 | HAcaBox | 121 |
| miR-200c | −0.31 | 0.009670586 | 0.625 | miRNA | 134 |
| miR-1260 | −0.78 | 0.010502121 | 0.726 | miRNA | 120 |
| miR-130a | −0.94 | 0.010557093 | 0.687 | miRNA | 122 |
| U17a | −0.52 | 0.010593144 | 0.702 | HAcaBox | 105 |
| ACA52 | −0.45 | 0.010843862 | 0.708 | HAcaBox | 121 |
| miR-197 | −0.79 | 0.011117393 | 0.724 | miRNA | 103 |
| U66 | −0.54 | 0.011246742 | 0.705 | HAcaBox | 119 |
| ENSG00000202252 | −0.30 | 0.011273976 | 0.699 | snoRNA | 135 |
| ACA61 | 0.22 | 0.011490951 | 0.730 | HAcaBox | 135 |
| miR-151-5p | 0.56 | 0.01153084 | 0.830 | miRNA | 135 |
| ACA16_x | −0.47 | 0.011881173 | 0.727 | HAcaBox | 98 |
| U18C_x | −0.45 | 0.012073238 | 0.691 | CDBox | 74 |
| U15A | 0.45 | 0.012634875 | 0.706 | CDBox | 128 |
| miR-1274a | 0.71 | 0.012698242 | 0.684 | miRNA | 48 |
| ACA9 | −0.62 | 0.01271037 | 0.691 | HAcaBox | 82 |
| U91_s | −0.54 | 0.012949986 | 0.733 | scaRna | 132 |
| ENSG00000207002 | −0.52 | 0.013212929 | 0.702 | snoRNA | 35 |
| miR-129-3p | −0.54 | 0.013303701 | 0.705 | miRNA | 59 |
| spike_in-cortrol-17 | 0.48 | 0.013556785 | 0.705 | Oligonucleotide spike-in controls | 33 |
| spike_in-control-2 | 0.19 | 0.014699249 | 0.684 | Oligonucleotide spike-in controls | 137 |
| ENSG00000212206 | 0.49 | 0.014866744 | 0.670 | snoRNA | 46 |
| miR-107 | −0.39 | 0.015131674 | 0.669 | miRNA | 135 |
| ACA63 | 0.42 | 0.01519582 | 0.695 | HAcaBox | 66 |

TABLE 7-continued miRNAs significantly expressed between nevi and normal skin

| Probe Name | Log2-FC | P value | AUC | ProbeType | #Sample Detected |
|---|---|---|---|---|---|
| ENSG00000212553_x | 0.45 | 0.015776333 | 0.684 | snoRNA | 60 |
| U50B | −0.37 | 0.016500241 | 0.704 | CDBox | 135 |
| ENSG00000207100_x | 0.36 | 0.016825837 | 0.666 | snoRNA | 72 |
| U78_s | −0.55 | 0.016840855 | 0.702 | CDBox | 135 |
| miR-551b-star | −0.65 | 0.016907402 | 0.686 | miRNA | 61 |
| ACA47 | 0.45 | 0.017340107 | 0.666 | scaRna | 77 |
| U92 | 0.45 | 0.017435918 | 0.760 | scaRna | 129 |
| miR-342-5p | −0.78 | 0.01779742 | 0.695 | miRNA | 98 |
| miR-128 | −0.56 | 0.017820912 | 0.699 | miRNA | 44 |
| U17a_x | −0.46 | 0.018370462 | 0.720 | HAcaBox | 115 |
| ENSG00000206909_x | 0.44 | 0.018373221 | 0.706 | snoRNA | 47 |
| U30 | −0.35 | 0.018607695 | 0.729 | CDBox | 135 |
| miR-98 | −0.57 | 0.019510485 | 0.677 | miRNA | 47 |
| miR-21-star | 0.62 | 0.019769732 | 0.686 | miRNA | 64 |
| miR-135b-star | 0.57 | 0.0198019 | 0.704 | miRNA | 38 |
| ACA2a | −0.42 | 0.019986353 | 0.677 | HAcaBox | 55 |
| U88 | 0.44 | 0.020351208 | 0.672 | scaRna | 69 |
| HBII-85-29_x | 0.39 | 0.020664805 | 0.666 | CDBox | 85 |
| 14qII-19 | 0.47 | 0.02089152 | 0.695 | CDBox | 43 |
| U83B | 0.19 | 0.020956657 | 0.677 | CDBox | 135 |
| miR-134 | −0.86 | 0.020986754 | 0.681 | miRNA | 61 |
| U83A | −0.40 | 0.021328386 | 0.698 | CDBox | 127 |
| ENSG00000202370 | 0.53 | 0.02172281 | 0.651 | snoRNA | 88 |
| U72_x | −0.35 | 0.021862862 | 0.697 | HAcaBox | 103 |
| ACA38 | −0.38 | 0.023364662 | 0.688 | HAcaBox | 42 |
| ENSG00000200394_x | 0.42 | 0.023498919 | 0.661 | snoRNA | 115 |
| miR-1324 | 0.50 | 0.023518344 | 0.684 | miRNA | 57 |
| miR-106b | 0.85 | 0.023747964 | 0.670 | miRNA | 127 |
| miR-589-star | 0.56 | 0.023792146 | 0.675 | miRNA | 43 |
| ACA6 | −0.36 | 0.024014637 | 0.673 | HAcaBox | 126 |
| ACA28 | 0.36 | 0.02403059 | 0.687 | HAcaBox | 120 |
| ACA57 | 0.36 | 0.024679323 | 0.748 | scaRna | 135 |
| HBII-85-4_x | 0.36 | 0.024717662 | 0.711 | CDBox | 125 |
| ENSG00000200897 | −0.41 | 0.024775335 | 0.662 | snoRNA | 38 |
| U16 | 0.42 | 0.024969966 | 0.712 | CDBox | 131 |
| ENSG00000200418 | −0.41 | 0.025790882 | 0.668 | snoRNA | 31 |
| U105 | −0.31 | 0.026442326 | 0.673 | CDBox | 126 |
| spike_in-control-34 | 0.44 | 0.026481739 | 0.665 | Oligonucleotide spike-in controls | 58 |
| spike_in-control-23 | 0.24 | 0.027477358 | 0.645 | Oligonucleotide spike-in controls | 137 |
| miR-196a-star | 0.61 | 0.028243677 | 0.677 | miRNA | 37 |
| HBII-296A | 0.33 | 0.02845867 | 0.659 | CDBox | 78 |
| U82 | 0.43 | 0.028925335 | 0.681 | CDBox | 131 |
| ENSG00000212558_x | −0.35 | 0.029963606 | 0.662 | snoRNA | 31 |
| miR-21 | 0.67 | 0.030060673 | 0.668 | miRNA | 79 |
| ACA31 | 0.37 | 0.030929941 | 0.702 | HAcaBox | 123 |
| miR-1257 | 0.55 | 0.031016296 | 0.676 | miRNA | 31 |
| ACA14b_x | −0.37 | 0.031018594 | 0.688 | HAcaBox | 105 |
| ACA33_x | 0.38 | 0.033957171 | 0.687 | HAcaBox | 129 |
| miR-199b-3p | 0.64 | 0.034530062 | 0.737 | miRNA | 134 |
| miR-100 | −0.61 | 0.034553062 | 0.681 | miRNA | 133 |
| U64 | −0.38 | 0.034971581 | 0.633 | HAcaBox | 101 |
| miR-10a | −0.67 | 0.037624151 | 0.666 | miRNA | 69 |
| miR-30e | 0.56 | 0.037770496 | 0.683 | miRNA | 57 |
| miR-199a-3p | 0.62 | 0.038490813 | 0.704 | miRNA | 134 |
| HBII-85-11 | −0.37 | 0.038507691 | 0.687 | CDBox | 31 |
| miR-505-star | −0.62 | 0.039242017 | 0.647 | miRNA | 58 |
| hsa-let-7f-1-star | 0.44 | 0.042251211 | 0.658 | miRNA | 64 |
| spike_in-control-29 | −0.19 | 0.043064083 | 0.684 | Oligonucleotide spike-in controls | 137 |
| miR-20b | 0.64 | 0.043397678 | 0.655 | miRNA | 99 |
| ACA5 | −0.40 | 0.044405124 | 0.693 | HAcaBox | 85 |
| miR-628-3p | 0.57 | 0.044447799 | 0.652 | miRNA | 38 |
| HBII-85-8_x | 0.40 | 0.045108021 | 0.681 | CDBox | 135 |
| HBII-85-27_x | 0.29 | 0.045678744 | 0.651 | CDBox | 56 |
| miR-99b-star | 0.49 | 0.049531821 | 0.651 | miRNA | 74 |

TABLE 8

50 miRNAs most significantly expressed between nevi and normal skin

| Probe Name | Log2-FC | P value | AUC | ProbeType | #SampleDetected |
|---|---|---|---|---|---|
| 14qII-14 | −3.87 | 3.6592E−27 | 1.000 | CDBox | 56 |
| 14qII-14_x | −3.21 | 3.815E−24 | 1.000 | CDBox | 56 |
| U74_x | 1.46 | 3.89068E−23 | 1.000 | CDBox | 135 |
| miR-509-3p | 5.78 | 1.67661E−22 | 0.997 | miRNA | 116 |
| miR-768-5p | −1.46 | 5.23441E−22 | 1.000 | miRNA | 135 |
| ENSG00000199411_s | 1.36 | 1.56796E−21 | 1.000 | snoRNA | 135 |
| Z17B | −1.94 | 2.89347E−20 | 0.997 | CDBox | 117 |
| miR-149 | −3.46 | 1.55425E−19 | 1.000 | miRNA | 100 |
| miR-125a-5p | −3.44 | 1.86526E−19 | 1.000 | miRNA | 128 |
| U43 | −1.19 | 3.32514E−19 | 1.000 | CDBox | 135 |
| miR-1308 | 1.55 | 8.1184E−19 | 0.964 | miRNA | 135 |
| U59A | 1.13 | 9.99768E−18 | 0.993 | CDBox | 135 |
| miR-146a | 4.44 | 3.16232E−17 | 0.975 | miRNA | 129 |
| miR-513a-5p | 3.77 | 1.05679E−16 | 0.972 | miRNA | 105 |
| ACA20 | −1.74 | 1.56297E−16 | 0.993 | HAcaBox | 131 |
| U43_x | −1.05 | 1.04459E−15 | 1.000 | CDBox | 135 |
| U44_x | −1.37 | 5.54123E−15 | 0.994 | CDBox | 135 |
| miR-127-3p | −3.56 | 7.53549E−15 | 0.988 | miRNA | 89 |
| miR-193b | −2.57 | 7.81928E−15 | 1.000 | miRNA | 130 |
| U83 | −1.25 | 9.30493E−15 | 0.993 | CDBox | 135 |
| miR-768-3p | 0.98 | 2.39925E−14 | 0.972 | miRNA | 137 |
| U33 | −1.02 | 2.44194E−14 | 0.997 | CDBox | 137 |
| miR-574-3p | −3.05 | 3.0433E−14 | 0.974 | miRNA | 122 |
| ACA16 | −1.86 | 3.35128E−14 | 0.968 | HAcaBox | 47 |
| 14qI-4 | −2.43 | 3.96317E−14 | 0.979 | CDBox | 80 |
| hsa-let-7c | −1.01 | 4.99111E−14 | 0.986 | miRNA | 135 |
| miR-342-3p | −2.06 | 1.67074E−13 | 0.996 | miRNA | 136 |
| hsa-let-7b | −1.01 | 2.25904E−13 | 0.964 | miRNA | 136 |
| miR-423-3p | −2.52 | 2.97967E−13 | 1.000 | miRNA | 107 |
| HBII-239 | −1.41 | 3.2162E−13 | 0.975 | CDBox | 135 |
| U38B_x | 1.52 | 3.80613E−13 | 0.968 | CDBox | 133 |
| miR-320b | −0.63 | 6.31909E−13 | 0.971 | miRNA | 135 |
| miR-923 | 0.93 | 6.48332E−13 | 0.990 | miRNA | 135 |
| U54 | −1.06 | 1.17197E−12 | 0.975 | CDBox | 135 |
| U38B | 1.80 | 1.18885E−12 | 0.976 | CDBox | 134 |
| U44 | −1.07 | 1.28887E−12 | 0.981 | CDBox | 134 |
| miR-139-5p | −2.70 | 2.74261E−12 | 0.940 | miRNA | 80 |
| miR-1826 | −0.71 | 2.83317E−12 | 0.958 | miRNA | 137 |
| ENSG00000199435 | 1.38 | 2.88249E−12 | 0.954 | snoRNA | 63 |
| miR-26a | 0.89 | 2.88328E−12 | 0.960 | miRNA | 136 |
| U58B_x | −1.47 | 3.60008E−12 | 0.940 | CDBox | 132 |
| HBII-180A_x | −1.43 | 4.25614E−12 | 0.992 | CDBox | 123 |
| 14qII-12_x | −2.09 | 4.30741E−12 | 0.949 | CDBox | 85 |
| miR-509-3-5p | 3.46 | 5.53398E−12 | 0.953 | miRNA | 107 |
| U55_x | −1.35 | 6.7836E−12 | 0.996 | CDBox | 135 |
| miR-149-star | 0.93 | 9.6022E−12 | 0.940 | miRNA | 135 |
| HBII-276 | −1.41 | 1.19464E−11 | 0.964 | CDBox | 132 |
| miR-23b | −0.75 | 1.72105E−11 | 0.968 | miRNA | 137 |
| miR-15b | −2.42 | 1.7823E−11 | 0.968 | miRNA | 125 |
| miR-921 | 1.73 | 1.93285E−11 | 0.954 | miRNA | 49 |

Example 4

The data from Example 3 was further analyzed to identify the combination of markers best able to distinguish (A) melanoma from normal skin and (B) melanoma from nevi. Each miRNA ("analyte") was examined by svm, random forest, boosting, lasso, baggin, cart, matt, logistic regression, and etree analyses. The use of multiple statistical method demonstrates that the best combination of markers identified by one statistical method is validated by every other method, making the choice of marker combinations less subject to the specific weaknesses of any one statistical algorithm.

FIGS. 1-10 show, respectively, the best 2-10 miRNA combinations for differentiating melanoma (MM) from normal skin ("NS") and the relevant error rates, as determined by different statistical algorithms.

FIGS. 11-23 show, respectively, the best 2-14 miRNA combinations for differentiating melanoma (MM) from nevi (NV), and the relevant error rates, as determined by different statistical algorithms.

Figure 24:
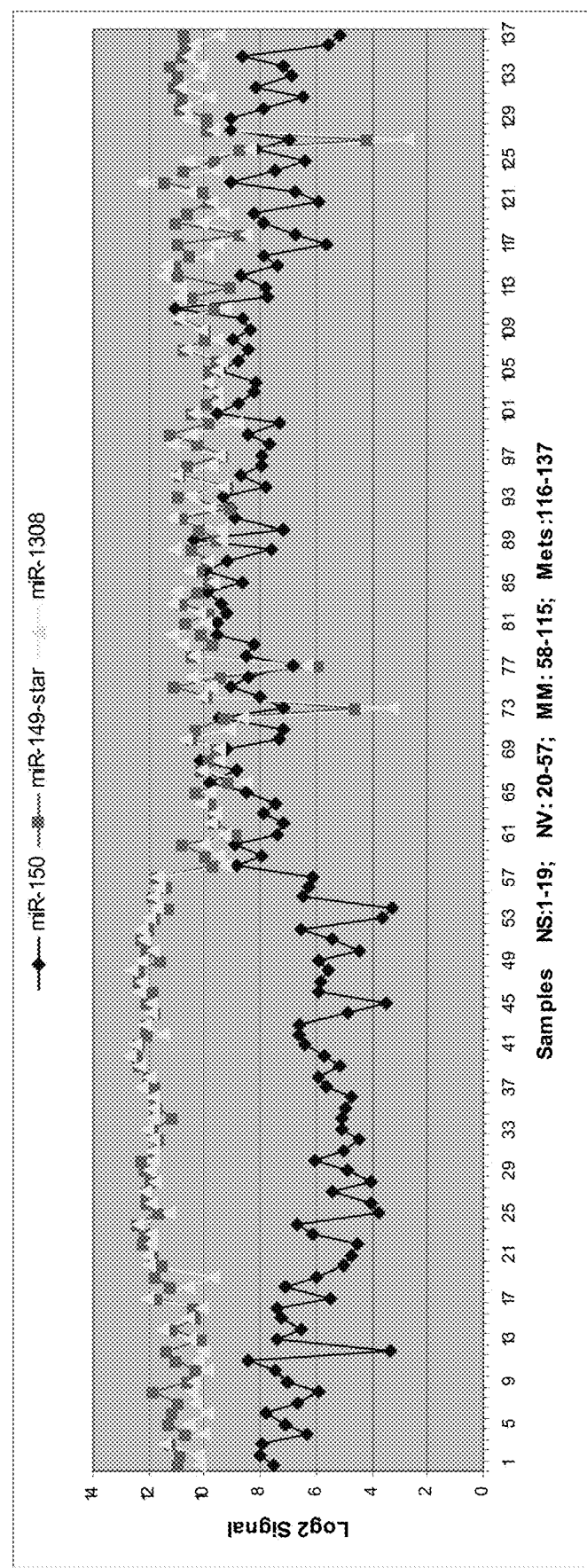
FIG. 24 shows the log 2 signal for three miRNA: miR-150 (miR-150), miR-149-star (miR-149-star), and hsa-miR-1308 (miR-1308) across 137 samples. Samples 1-19 are normal skin (NS), 20-57 nevi (NV), 58-115 melanoma (MM) and 116-137 metastatic melanoma (Mets). As can be appreciated, miR-150, miR-149-star and miR-1308 distinguish normal skin and nevi from melanoma and metastatic.
Figure 25:
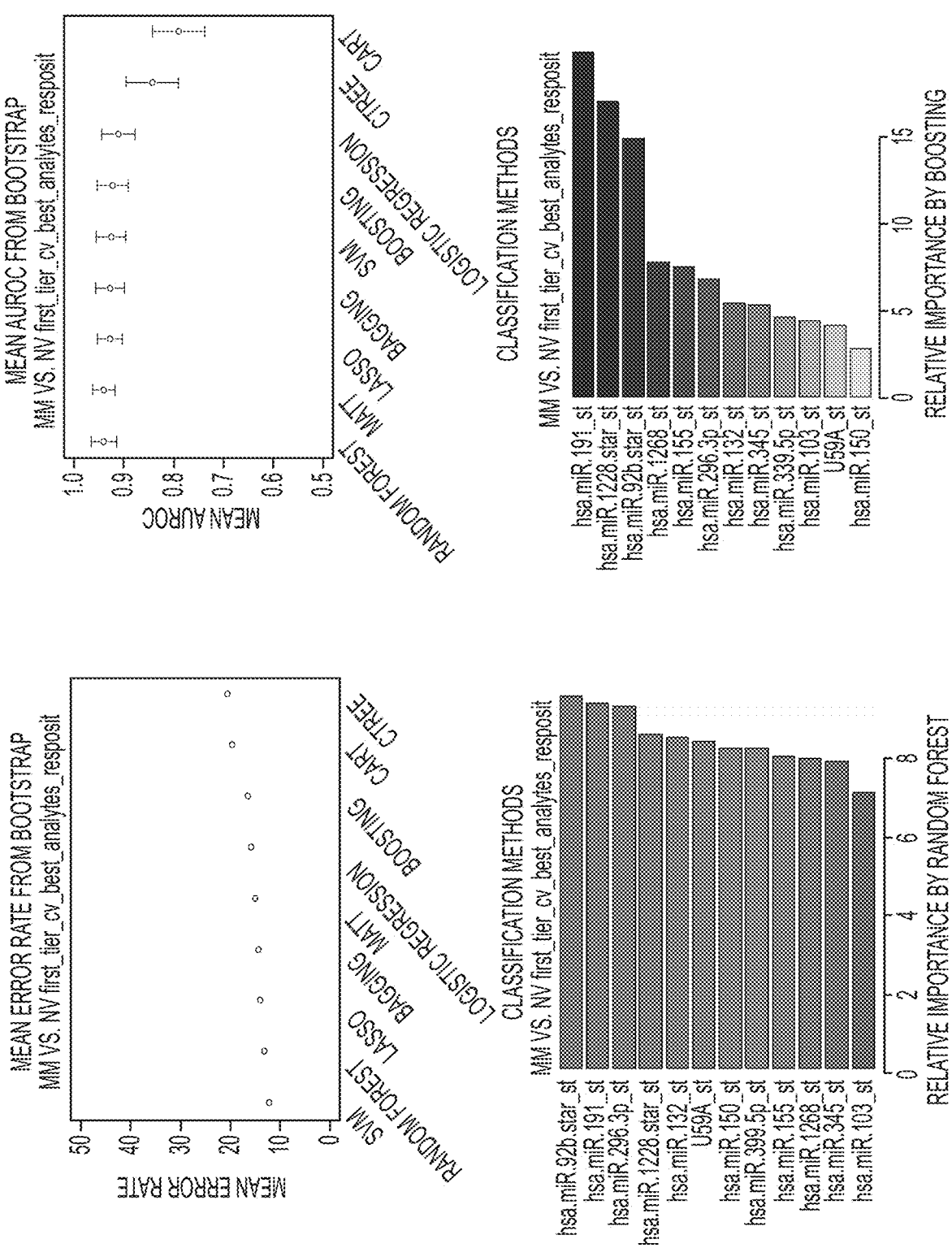
FIG. 25 shows an example of error rate and AUC from 9 programs analyzing the ability of groups of miRNA analytes to differentiate between melanoma and nevi.

FIG. 24 shows the log 2 signal for three miRNA: miR-150 (miR-150), miR-149-star (miR-149-star), and hsa-miR-1308 (miR-1308) across 137 samples. Samples 1-19 are normal skin (NS), 20-57 nevi (NV), 58-115 melanoma (MM) and 116-137 metastatic melanoma (Mets). As can be appreciated, miR-150, miR-149-star and miR-1308 distinguish normal skin and nevi from melanoma and metastatic melanoma In a follow up study, a total of 78 melanoma and 98 nevi (Intradermal-20, Compound-18, Junctional-20, Blue-20, Spitz-20) were studied on microarray. The candidate microRNAs were chosen based on AUC, p value, log 2 fold change, and 9 analysis programs, as before. A example of error rate and AUC from 9 programs is set forth in FIG. 25. The candidate microRNAs identified from 2 programs (random forest and boosting) are listed in Table 9, below.

TABLE 9

MicroRNA candidates from 78 melanoma and 98 nevi

| microrna | adj. P. Val (FDR) | AUC | Log2FC | Order in program |
|---|---|---|---|---|
| miR-1268 | 1.45E-19 | 0.89 | -1.80 | 5 |
| miR-1228-star | 2.87E-19 | 0.91 | -1.77 | 2 |
| miR-92b-star | 4.62E-18 | 0.88 | -1.73 | 3 |
| miR-155 | 5.56E-18 | 0.86 | 2.85 | 4 |
| miR-345 | 1.19E-16 | 0.85 | 1.83 | 7 |
| miR-425 | 5.11E-16 | 0.85 | 1.80 | |
| miR-132 | 5.24E-16 | 0.85 | 1.75 | 10 |
| miR-1207-5p | 1.18E-15 | 0.86 | -1.40 | |
| miR-1301 | 2.17E-15 | 0.83 | 1.70 | |
| miR-663 | 2.26E-15 | 0.85 | -1.43 | |
| miR-339-5p | 2.26E-15 | 0.85 | 1.60 | 9 |
| miR-149-star | 5.28E-15 | 0.85 | -1.32 | |
| miR-150 | 5.25E-14 | 0.82 | 2.10 | 6 |
| miR-18a | 5.80E-13 | 0.8 | 0.84 | |
| miR-103 | 1.52E-11 | 0.86 | 0.93 | 8 |
| miR-191 | 7.32E-13 | 0.9 | 0.85 | 1 |
| miR-296-3p | 1.05E-09 | 0.79 | -0.85 | 11 |
| miR-31 | 1.39E-12 | 0.79 | 2.46 | |
| miR-107* | 3.27E-10 | 0.85 | 0.86 | |
| miR-93* | 1.05E-09 | 0.85 | 1.14 | |
| miR-1275* | 4.59E-11 | 0.8 | -1.16 | |
| miR-181B* | 3.69E-12 | 0.83 | 1.69 | |
| miR-921* | 7.21E-12 | 0.81 | -0.89 | |
| miR-1225-5p | 7.63E-10 | 0.78 | -1.3 | |
| miR-1202 | 1.08E-09 | 0.76 | -1.34 | |
| miR-342-3p | 1.55E-10 | 0.78 | 1.29 | |
| Internal control candidates | | | | |
| miR-27b | 0.72 | 0.07 | 0.501 | |
| miR-195 | 0.95 | 0.01 | 0.506 | |
| miR-199b-3p | 0.78 | 0.05 | 0.509 | |
| miR-199a-3p | 0.86 | 0.03 | 0.511 | |

REFERENCES

1. Leidinger P, Keller A, Borries A, Reichrath J, Rass K, Jager S U, Lenhof H P, Meese E. High-throughput miRNA profiling of human melanoma blood samples. BMC Cancer. 2010 Jun. 7; 10:262.
2. Demetra Philippidou, Martina Schmitt, Dirk Moser, Christiane Margue, Petr V Nazarov, Arnaud Muller, Laurent Vallar, Dorothee Nashan, Iris Behrmann and Stephanie Kreis Signatures of MicroRNAs and Selected MicroRNA Target Genes in Human Melanoma. Cancer Res 2010 May 70(10); 4163-4173
3. Segura F, Ilana Belitskaya-Lévy I, Rose A, Zakrzewski J, Gaziel A. Melanoma MicroRNA Signature Predicts Post-Recurrence Survival Clinical Cancer Research 2020 Mar. 16(5): 1577-1586

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for distinguishing melanoma cells from normal and dysplastic nevi cells in a skin lesion sample from a subject, comprising:
    (a) amplifying nucleic acids from the skin lesion sample;
    (b) assaying the expression level of one or more miRNAs in the skin lesion sample, wherein the one or more miRNAs comprise miR-339-5p, miR-15b, miR-572, miR-425, miR-1202, HBII-382_s, miR-1225-5p, miR-30c, miR-106b-star, miR-125a-5p, mgU6-53B, miR-25, miR-939, miR-92b-star, miR-500-star, miR-22, HBII-142_x, miR-181b, HBII-142, miR-663, miR-1224-5p, HBII-85-6_x, miR-1301, miR-345, miR-30a-star, ENSG00000202327, miR-92a, miR-127-3p, HBII-85-26, miR-31, miR-921, miR-146b-5p, miR-768-3p, miR-708, miR-139-5p, ACA24_x, miR-501-3p, or miR-502-3p;
    (c) quantitatively comparing the levels of the one or more miRNAs in the skin sample as assayed in (a) to the levels of corresponding miRNA(s) in a normal skin or nevus reference sample; and
    (d) identifying the skin lesion sample as containing:
        (i) melanoma cells if the levels of the one or more miRNAs in the skin lesion sample differ from the normal skin or nevus reference sample, wherein the level of miR-339-5p, miR-15b, miR-425, miR-30c, miR-106b-star, miR-125a-5p, miR-25, miR-500-star, miR-22, miR-1301, miR-345, miR-30a-star, miR-181b, miR-92a, miR-127-3p, miR-31, miR-146b-5p, miR-708, miR-139-5p, ACA24_x, miR-501-3p, miR-502-3p are increased and the level of miR-572, miR-1202, HBII-382_s, miR-1225-5p, mgU6-53B, miR-939, miR-92b-star, HBII-142_x, HBII-142, miR-663, miR-1224-5p, HBII-85-6_x, ENSG00000202327, HBII-85-26, miR-921, miR-768-3p are decreased relative to the normal skin or nevus reference sample, or (ii) not melanoma cells if the levels of the one or more miRNAs in the skin lesion sample do not differ from the normal skin or nevus reference sample.

2. The method of claim 1, wherein the assaying comprises detecting amplified nucleic acids from the skin lesion sample.

3. The method of claim 2, wherein nucleic acids from the skin lesion sample are amplified by performing reverse transcriptase polymerase chain reaction (RT-PCR) to generate the amplified nucleic acids.

4. The method of claim 3, further comprising isolating the nucleic acids from the skin lesion sample.

5. The method of claim 1, wherein the skin lesion sample is suspected of containing melanoma cells.

6. The method of claim 1, wherein the skin lesion sample is a formalin fixed paraffin-embedded skin lesion sample.

7. The method of claim 1, further comprising histopathological assessment of the skin lesion sample.

8. The method of claim 1, further comprising:

(a) scoring (i) clinical observations of the subject (ii) histopathological assessment of the skin sample and (iii) expression levels of the miRNAs; and (b) combining (i), (ii) and (iii) to obtain a diagnostic score, that indicates the likelihood of melanoma in the subject.

9. A kit for distinguishing melanoma cells from normal and dysplastic nevi cells in a skin lesion sample from a subject, comprising one or more primer pairs that can be used for amplifying miRNA in the skin lesion sample, wherein the miRNAs comprise miR-339-5p, miR-15b, miR-572, miR-425, miR-1202, HBII-382_s, miR-1225-5p, miR-30c, miR-106b-star, miR-125a-5p, mgU6-53B, miR-25, miR-939, miR-92b-star, miR-500-star, miR-22, HBII-142_x, miR-181b, HBII-142, miR-663, miR-1224-5p, HBII-85-6-x, miR-1301, miR-345, miR-30a-star, ENSG00000202327, miR-92a, miR-127-3p, HBII-85-26, miR-31, miR-921, miR-146b-5p, miR-768-3p, miR-708, miR-139-5p, ACA24_x, miR-501-3p, or miR-502-3p; and wherein at least one primer pair is detectably labeled.

10. The kit of claim 9, wherein the detectable label is a fluorescent marker or a radioactive isotope.

11. The kit of claim 9, wherein the skin lesion sample is obtained from a skin lesion.

12. The kit of claim 9, wherein the skin lesion sample is a formalin fixed paraffin-embedded skin lesion sample.

\* \* \* \* \*